(12) United States Patent
Peer et al.

(10) Patent No.: US 9,925,143 B2
(45) Date of Patent: Mar. 27, 2018

(54) LIPIDATED GLYCOSAMINOGLYCAN PARTICLES FOR THE DELIVERY OF NUCLEIC ACIDS

(71) Applicants: RAMOT AT TEL-AVIV UNIVERSITY LTD., Tel Aviv (IL); QUIET THERAPEUTICS LTD., Ness Zion (IL)

(72) Inventors: Dan Peer, Kiryat Ono (IL); Evgenia Alpert, Jerusalem (IL)

(73) Assignees: RAMOT AT TEL-AVIV UNIVERSITY LTD., Tel Aviv (IL); QUIET THERAPEUTICS LTD., Ness Ziona (IL)

( * ) Notice: Subject to any disclaimer, the term of this patent is extended or adjusted under 35 U.S.C. 154(b) by 0 days.

(21) Appl. No.: 14/395,198

(22) PCT Filed: Mar. 14, 2013

(86) PCT No.: PCT/IL2013/050238
§ 371 (c)(1),
(2) Date: Oct. 17, 2014

(87) PCT Pub. No.: WO2013/156989
PCT Pub. Date: Oct. 24, 2013

(65) Prior Publication Data
US 2015/0140108 A1 May 21, 2015

Related U.S. Application Data

(60) Provisional application No. 61/625,720, filed on Apr. 18, 2012.

(51) Int. Cl.
| | |
|---|---|
| A61K 9/16 | (2006.01) |
| A61K 48/00 | (2006.01) |
| A61K 47/18 | (2017.01) |
| A61K 47/36 | (2006.01) |
| C12N 15/88 | (2006.01) |
| A61K 9/51 | (2006.01) |
| A61K 31/713 | (2006.01) |
| C12N 15/113 | (2010.01) |
| A61K 9/127 | (2006.01) |
| A61K 47/54 | (2017.01) |
| A61K 47/69 | (2017.01) |

(52) U.S. Cl.
CPC .............. *A61K 9/16* (2013.01); *A61K 9/1272* (2013.01); *A61K 9/1617* (2013.01); *A61K 9/1652* (2013.01); *A61K 9/5123* (2013.01); *A61K 9/5161* (2013.01); *A61K 31/713* (2013.01); *A61K 47/543* (2017.08); *A61K 47/6939* (2017.08); *A61K 47/6941* (2017.08); *C12N 15/113* (2013.01); *C12N 15/88* (2013.01); *A61K 48/00* (2013.01); *C12N 2310/14* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,235,871 A | 11/1980 | Papahadjopoulos et al. |
| 4,666,828 A | 5/1987 | Gusella |
| 4,683,202 A | 7/1987 | Mulls |
| 4,801,531 A | 1/1989 | Frossard |
| 4,879,219 A | 11/1989 | Wands et al. |
| 4,898,735 A | 2/1990 | Barenholz et al. |
| 4,902,512 A | 2/1990 | Ishigami et al. |
| 4,927,637 A | 5/1990 | Marano et al. |
| 5,011,771 A | 4/1991 | Bellet et al. |
| 5,143,713 A | 9/1992 | Phillips et al. |
| 5,192,659 A | 3/1993 | Simons |
| 5,272,057 A | 12/1993 | Smulson et al. |
| 5,281,521 A | 1/1994 | Trojanowski et al. |

(Continued)

FOREIGN PATENT DOCUMENTS

| | | |
|---|---|---|
| JP | H09-511525 A | 11/1997 |
| JP | 2003-528131 A | 9/2003 |

(Continued)

OTHER PUBLICATIONS

Kundu et al., Stability of Lyophilized siRNA Nanosome Formulations. Int J Pharm. Feb. 28, 2012; 423(2): 525-534.*
Choi et al., (Sep. 2009) Self-assembled hyaluronic acid nanoparticles for active tumor targeting. Biomaterials 31(1): 106-14.
Lee et al., (Feb. 2007) Target-specific intracellular delivery of siRNA using degradable hyaluronic acid nanogels. J Control Release 119(2): 245-52.
Manjunath and Dykxhoorn (May 2010) Advances in synthetic siRNA delivery. Discovery Medicine 9(48): 418-430.
Peer (Jul. 2010) Induction of therapeutic gene silencing in leukocyte-implicated diseases by targeted and stabilized nanoparticles: A mini-review. J Controlled Release 148(1): 63-8.

(Continued)

*Primary Examiner* — Scott Long
*Assistant Examiner* — Arthur S Leonard
(74) *Attorney, Agent, or Firm* — Browdy and Neimark, PLLC

(57) ABSTRACT

There are provided compositions comprising lipidated glycosaminoglycan particles, methods for their preparation and uses thereof for the efficient in-vivo and in-vitro delivery of nucleic acids, such as, siRNA molecules.

14 Claims, 37 Drawing Sheets

(56) References Cited

U.S. PATENT DOCUMENTS

| | | |
|---|---|---|
| 5,401,511 A | 3/1995 | Margalit |
| 5,614,506 A | 3/1997 | Falk et al. |
| 5,624,839 A | 4/1997 | Yada et al. |
| 5,637,483 A | 6/1997 | Dranoff et al. |
| 5,639,738 A | 6/1997 | Falk et al. |
| 5,674,857 A | 10/1997 | Falk et al. |
| 5,733,892 A | 3/1998 | Sakurai et al. |
| 5,783,566 A | 7/1998 | Mislick |
| 5,792,753 A | 8/1998 | Falk et al. |
| 5,811,410 A | 9/1998 | Falk et al. |
| 5,817,642 A | 10/1998 | Falk et al. |
| 5,824,658 A | 10/1998 | Falk et al. |
| 5,827,834 A | 10/1998 | Falk et al. |
| 5,830,882 A | 11/1998 | Falk et al. |
| 5,834,444 A | 11/1998 | Falk et al. |
| 5,847,002 A | 12/1998 | Willoughby et al. |
| 5,852,002 A | 12/1998 | Falk et al. |
| 5,910,489 A | 6/1999 | Falk et al. |
| 5,914,314 A | 6/1999 | Falk et al. |
| 5,914,322 A | 6/1999 | Falk et al. |
| 5,922,350 A | 7/1999 | Janoff et al. |
| 5,929,048 A | 7/1999 | Falk et al. |
| 5,932,560 A | 8/1999 | Falk et al. |
| 5,942,498 A | 8/1999 | Falk et al. |
| 5,962,433 A | 10/1999 | Falk et al. |
| 5,972,906 A | 10/1999 | Asculai et al. |
| 5,977,088 A | 11/1999 | Harper et al. |
| 5,985,850 A | 11/1999 | Falk et al. |
| 5,985,851 A | 11/1999 | Falk et al. |
| 5,990,095 A | 11/1999 | Falk et al. |
| 5,990,096 A | 11/1999 | Asculai et al. |
| 6,017,900 A | 1/2000 | Falk et al. |
| 6,022,866 A | 2/2000 | Falk et al. |
| 6,048,844 A | 4/2000 | Falk et al. |
| 6,069,135 A | 5/2000 | Falk et al. |
| 6,087,344 A | 7/2000 | Falk et al. |
| 6,103,704 A | 8/2000 | Falk et al. |
| 6,114,314 A | 9/2000 | Falk et al. |
| 6,136,793 A | 10/2000 | Falk et al. |
| 6,140,312 A | 10/2000 | Falk et al. |
| 6,147,059 A | 11/2000 | Falk et al. |
| 6,194,392 B1 | 2/2001 | Falk et al. |
| 6,207,178 B1 | 3/2001 | Westesen et al. |
| 6,218,373 B1 | 4/2001 | Falk et al. |
| 6,348,185 B1 | 2/2002 | Piwnica-Worms |
| 6,593,308 B2 | 7/2003 | Szoka |
| 6,986,902 B1* | 1/2006 | Chen ............... A61K 9/1273 424/1.21 |
| 7,544,374 B2 | 6/2009 | Margalit |
| 8,277,847 B2 | 10/2012 | Margalit et al. |
| 9,259,474 B2 | 2/2016 | Margalit et al. |
| 9,526,705 B2 | 12/2016 | Margalit et al. |
| 9,574,210 B2 | 2/2017 | Peer et al. |
| 2001/0008772 A1 | 7/2001 | Smith et al. |
| 2001/0031740 A1 | 10/2001 | Unger et al. |
| 2001/0038851 A1 | 11/2001 | Allen et al. |
| 2001/0044528 A1 | 11/2001 | Innis et al. |
| 2002/0012998 A1 | 1/2002 | Gonda et al. |
| 2002/0061849 A1 | 5/2002 | Nielsen et al. |
| 2002/0131995 A1 | 9/2002 | Francis, Jr. |
| 2003/0175733 A1 | 9/2003 | Kirst et al. |
| 2004/0241248 A1 | 12/2004 | Margalit |
| 2006/0019912 A1 | 1/2006 | Burkoth et al. |
| 2009/0155178 A1 | 6/2009 | Margalit et al. |
| 2009/0291131 A1 | 11/2009 | MacLachlan et al. |
| 2012/0129916 A1 | 5/2012 | Peer et al. |
| 2013/0095032 A1 | 4/2013 | Margalit et al. |
| 2015/0216998 A1 | 8/2015 | Feinstein et al. |
| 2016/0113882 A1 | 4/2016 | Margalit et al. |

FOREIGN PATENT DOCUMENTS

| | | |
|---|---|---|
| JP | 2011-507534 A | 3/2011 |
| KR | 10-0806088 B1 | 2/2008 |
| WO | WO 2001/039815 A2 | 6/2001 |
| WO | WO 2003/015755 A1 | 2/2003 |
| WO | WO 2007/127219 A2 | 11/2007 |
| WO | WO 2007/127272 A2 | 11/2007 |
| WO | WO 2009/020270 A1 | 2/2009 |
| WO | WO 2009/026328 A2 | 2/2009 |
| WO | 2011/013130 | 2/2011 |
| WO | WO 2011/075656 A1 | 6/2011 |
| WO | WO 2013/156989 A1 | 10/2013 |
| WO | WO 2015/198326 A1 | 12/2015 |

OTHER PUBLICATIONS

Peer et al., (Feb. 2008) Systemic leukocyte-directed siRNA delivery revealing cyclin D1 as an anti-Inflammation target. Science 319(5863): 627-30.

Taetz et al., (Apr. 2009) Hyaluronic acid-modified DOTAP/DOPE liposomes for the targeted delivery of anti-telomerase siRNA to CD44-expressing lung cancer cells. Oligonucleotides 19(2): 103-16.

Weinstein and Peer (May 2010) RNAi nanomedicines: challenges and opportunities within the immune system. Nanotechnology 21(23):1-13.

European Application No. 13778205.8, Extended European Search Report, dated Jul. 29, 2015, 5 pages.

European Application No. 02761287.8, Supplementary European Search Report, dated Feb. 8, 2010, 3 pages.

International Search Report for International Application No. PCT/US2002/025178 dated Dec. 20, 2002, 1 page.

International Search Report and Written Opinion for International Application No. PCT/IL2010/000614 dated Jan. 21, 2011, 14 pages.

International Preliminary Report on Patentability for International Application No. PCT/IL2010/000614 dated Jan. 31, 2012, 9 pages.

International Search Report and Written Opinion for International Application No. PCT/IL2013/050238 dated Jun. 20, 2013, 10 pages.

International Preliminary Report on Patentability for International Application No. PCT/IL2013/050238 dated Oct. 21, 2014, 8 pages.

International Search Report and Written Opinion for International Application No. PCT/IL2015/050653 dated Oct. 15, 2015, 13 pages.

International Search Report and Written Opinion for International Application No. PCT/IL2015/050653 dated Dec. 27, 2016, 8 pages.

Aoki et al., "In vivo transfer efficiency of antisense oligonucleotides into the myocardium using HVJ-liposome method." Biochem Biophys Res Commun (1997); 231(3): 540-545.

Barkay, Zahava, et al. "Three-dimensional characterization of drug-encapsulating particles using STEM detector in FEG-SEM." Micron (2009); 40(4): 480-485.

Bhargava et al., "Long double-stranded RNA-mediated RNA interference as a tool to achieve site-specific ilencing of hypothalamic neuropeptides." Brain Res Brain Res Protoc (2004); 13(2): 115-125.

Billy, et al., "Specific interference with gene expression induced by long, double-stranded RNA in mouse embryonal teratocarcinoma cell lines", PNAS (2001); 98(25): 14428-14433.

Britannica Online Encyclopedia, "liposome", downloaded Nov. 14, 2008 http://www.britannica.com/Ebchecked/topic/342910/liposome, 1 page.

Brummelkamp et al., "A system for stable expression of short interfering RNAs in mammalian cells." Science (2002); 296 (5567): 550-553.

Castanotto et al., "Functional siRNA expression from transfected PCR products." RNA (2002); 8(11 ): 1454-1460.

Chekhonin, et al., "Immunoliposomal containers as systems of directed transport of minor interfering RNA into Schwann cells", Bulletin of Experimental Biology and Medicine (2008); 146(4): 451-454.

Chono, et al., "An efficient and low immunostimulatory nanoparticle formulation for systemic siRNA delivery to the tumor", Journal of Controlled Release (2008); 131(1): 64-69.

Diallo et al., "Long endogenous dsRNAs can induce complete gene silencing in mammalian cells and primary cultures." Oligonucleotides (2003); 13(5): 381-392.

Dorland's Illustrated Medical Dictionary, "liposis", 30th edition, Saunders, PA, 2003, p. 1058, 3 pages.

(56) References Cited

OTHER PUBLICATIONS

Firth et al., "Studies on the use of antimitotic drugs entrapped within liposomes and of their action on a human glioma cell line," J Neurol Sci (1984); 63(2): 153-165.
Grishok et al., "Genes and mechanisms related to RNA interference regulate expression of the small temporal RNAs that control C.elegans developmental timing." Cell (2001); 106(1): 23-34.
Guo et al., "MicroRNA directs mRNA cleavage of the transcription factor NAC1 to downregulate auxin signals for *Arabidopsis* lateral root development." Plant Cell (2005); 17(5): 1376-1386.
Hammond et al., "Argonaute2, a link between genetic and biochemical analyses of RNAi." Science (2001); 293(5532): 1146-1150.
Han, et al., "Cationic derivatives of biocompatible hyaluronic acids for delivery of siRNA and antisense oligonucleotides", Journal of Drug Targeting (2009); 17(2): 123-132.
Herringson, et al., "Convenient targeting of stealth siRNA-lipoplexes to cells with chelator lipid-anchored molecules", Journal of Controlled Release (2009); 139(3): 229-238.
https://www.caymanchem.com/app/template/Product.vm/catalog/15084, retrieved from the internet on Apr. 19, 2015, 2 pages.
Huang, Chin-Yi, et al. "Lipitoids—novel cationic lipids for cellular delivery of plasmid DNA in vitro." Chemistry & Biology (1998); 5(6): 345-354.
Hutvágner and Zamore, "A microRNA in a multiple-turnover RNAi enzyme complex." Science (2002); 297(5589): 2056-2060.
Hutvágner et al., "A cellular function for the RNA-interference enzyme Dicer in the maturation of the let-7 small temporal RNA." Science (2001); 293(5531): 834-838.
Jiang, et al., "Hyaluronic acid-polyethyleneimine conjugate for target specific intracellular delivery of siRNA", Biopolymers (2008); 89(7): 635-642.
Jiang, et al., "Target Specific Intracellular Delivery of siRNA/PEI-HA Complex by Receptor Mediated Endocytosis", Molecular Pharmaceutics (2009); 6(3): 727-737.
Kelling et al., "Dicer functions in RNA interference and in synthesis of small RNA involved in developmental timing in C.elegans." Genes Dev (2001); 15(20): 2654-2659.
Kronenwett et al., "Oligodeoxyribonucleotide uptake in primary human hematopoietic cells is enhanced by cationic lipids and depends on the hematopoietic cell subset." Blood (1998); 91(3): 852-862.
Landesman-Milo, D and Peer, D., "Toxicity profiling of several common RNAi-based nanomedicines: a comparative study." Drug Deliv. and Transl.Res. (2013); 4(1): 96-103 (published online May 29, 2013) DOI 10.1007/s13346-013-0158-7).
Lasic, Danilo D. "Liposomes", Liposomes in gene delivery, CRC press, 1997, Ch. 6, pp. 67-68.
Lavigne and Thierry, "Enhanced antisense inhibition of human immunodeficiency virus type 1 in cell cultures by DLS delivery system." Biochem Biophys Res Commun (1997); 237(3): 566-571.
Lee et al., "The C.elegans heterochronic gene lin-4 encodes small RNAs with antisense complementarity to lin-14." Cell (1993); 75(5): 843-854.
Luft, "Making sense out of antisense oligodeoxynucleotide delivery: getting there is half the fun." J Mol Med (Berl) (1998); 76(2): 75-76.
Matveeva et al., "Prediction of antisense oligonucleotide efficacy by in vitro methods." Nat Biotechnol (1998); 16(13): 1374-1375.
Merriam Webster Online Dictionary, "liposome", downloaded Nov. 14, 2008 http://www.merriam-webster.com/dictionary/liposome, 1 page.
Monsigny et al., "Sugar-lectin interactions: how does wheat-germ agglutinin bind sialoglycoconjugates?" Eur J Biochem (1980); 104(1): 147-153.
Mourelatos et al., "miRNPs: a novel class of ribonucleoproteins containing numerous microRNAs." Genes Dev (2002); 16(6): 720-728.
Nakajima, et al., "Mechanism of amide formation by carbodiimide for bioconjugation in aqueous media", Bioconjugate Chem. (1995); 6(1): 123-130.
O'Reilly, et al., "Endostatin: an endogenous inhibitor of angiogenesis and tumor growth", Cell (1997); 2(88): 277-285.
Paddison et al., "Stable suppression of gene expression by RNAi in mammalian cells." Proc Nall Acad Sci U S A (2002); 9(3): 1443-1448.
Parizotto et al., "In vivo investigation of the transcription, processing, endonucleolytic activity, and functional elevance of the spatial distribution of a plant miRNA." Genes Dev (2004); 18(18): 2237-2242 and erratum.
Peer, et al., "Hyaluronan is a key component in cryoprotection and formulation of targeted unilamellar liposomes", Biochimica et Biophysica Acta (2003); 1612(1): 76-82.
Peer, et al., "Selective gene silencing in activated leukocytes by targeting siRNAs to the integrin lymphocyte function-associated antigen-1", PNAS (2007); 104(10): 4095-4100.
Peer, et al., "Physicochemical evaluation of a stability-driven approach to drug entrapment in regular and in surface-modified liposomes", Archives of Biochemistry and Biophysics (2000); 383(2): 185-190.
Peer, D and Shimaoka, M. "Systemic siRNA delivery to leukocyte-implicated diseases." Cell Cycle (2009); 8(6): 853-859.
Pierce 1994 Catalog, 4 pages.
Rajur et al., Covalent protein—Oligonucleotide conjugates for efficient delivery of antisense molecules. Bioconjug Chem (1997); 8(6): 935-940.
Rivkin, Ilia, et al. "Paclitaxel-clusters coated with hyaluronan as selective tumor-targeted nanovectors." Biomaterials (2010); 31(27): 7106-7114.
Romberg, Birgit, et al. "Enzyme-induced shedding of a poly (amino acid)-coating triggers contents release from dioleoyl phosphatidylethanolamine liposomes." International Journal of Pharmaceutics (2008); 355(1): 108-113.
Rose et al., "Functional polarity is introduced by Dicer processing of short substrate RNAs." Nucleic Acids Res (2005); 33(13): 4140-4156.
Ruozi, Barbara, et al. "Immunoliposomal systems targeting primary effusion lymphoma: in vitro study." Nanomedicine (2010); 5(7): 1051-1064.
Saul, Justin M., et al. "Controlled targeting of liposomal doxorubicin via the folate receptor in vitro." Journal of Controlled Release (2003); 92(1): 49-67.
Shinagawa and Ishii, "Generation of Ski-knockdown mice by expressing a long double-strand RNA from an RNA polymerase II promoter." Genes Dev (2003); 17(11): 1340-1345.
Strat et al., "Specific and nontoxic silencing in mammalian cells with expressed long dsRNAs." Nucleic Acids Res (2006); 34(13): 3803-3810.
Surace, et al., "Lipoplexes targeting the CD44 hyaluronic acid receptor for efficient transfection of breast cancer cells", Molecular Pharmaceutics (2009); 6(4): 1062-1073.
Tam, Yuen Yi C., et al. "Advances in lipid nanoparticles for siRNA delivery." Pharmaceutics (2013); 5(3): 498-507.
Thermo Scientific Crosslinking Technical Handbook, Jan. 1, 2012, XP55272448; Retrieved from the Internet: URL: hllps://tools.thermofisher.com/contenl/sfs/brochures/1602163-Crosslinking-Reagents-Handbook.pdf; 56 pages.
Torchilin, Vladimir P. "Recent advances with liposomes as pharmaceutical carriers." Nature Reviews Drug Discovery (2005); 4(2): 145-160.
Tran et al., "Control of specific gene expression in mammalian cells by co-expression of long complementary RNAs." FEBS (2004); Lett 573(1-3): 127-134.
Tuschl, "RNA interference and small interfering RNAs." Chembiochem (2001); 2(4): 239-245.
Walton et al., "Prediction of antisense oligonucleotide binding affinity to a structured RNA target." Biotechnol Bioeng (1999); 65(1): 1-9.
Wightman et al., "Posttranscriptional regulation of the heterochronic gene lin-14 by lin-4 mediates temporal pattern formation in C. elegans." Cell (1993); 75(5): 855-862.

(56) References Cited

OTHER PUBLICATIONS

Williams and Rubin, ARGONAUTE1 is required for efficient RNA interference in *Drosophila* embryos. Proc Natl Acad Sci US A (2002); 99(10): 6889-6894.

Yagi et al., "Interferon-beta endogenously produced by intratumoral injection of cationic liposome-encapsulated gene: cytocidal effect on glioma transplanted into nude mouse brain," Biochem Mol Biol Int (1994); 32(1): 167-171.

Yen et al., "CD44 Mediated Nonviral Gene Delivery into Human Embryonic Stem Cells via Hyaluronic-Acid-Coated Nanoparticles." ACS Biomater Sci Eng (2016); 2(3): 326-335.

Yu, et al., "let-7 regulates self renewal and tumorigenicity of breast cancer cells", Cell (2007); 131(6): 1109-1123.

Zeng et al., "Both natural and designed micro RNAs can inhibit the expression of cognate mRNAs when expressed in human cells." Mol Cell (2002); 9(6): 1327-1333.

\* cited by examiner

Panel A

Panel B

Panel C

| Incubation time (min) | 0 | 30 | 60 | 90 | 120 | 180 | -- | 60 | 0 | 180 |
|---|---|---|---|---|---|---|---|---|---|---|
| GAG siRNA | + | + | + | + | + | + | -- | -- | + | + |
| Human Serum | + | + | + | + | + | + | -- | + | -- | -- |
| siRNA only | -- | -- | -- | -- | -- | -- | + | + | -- | -- |

| Incubation time (min) | - | 60 | 0 | 180 |
|---|---|---|---|---|
| GAG siRNA | - | - | + | + |
| Human Serum | - | + | - | - |
| siRNA only | + | + | - | - |

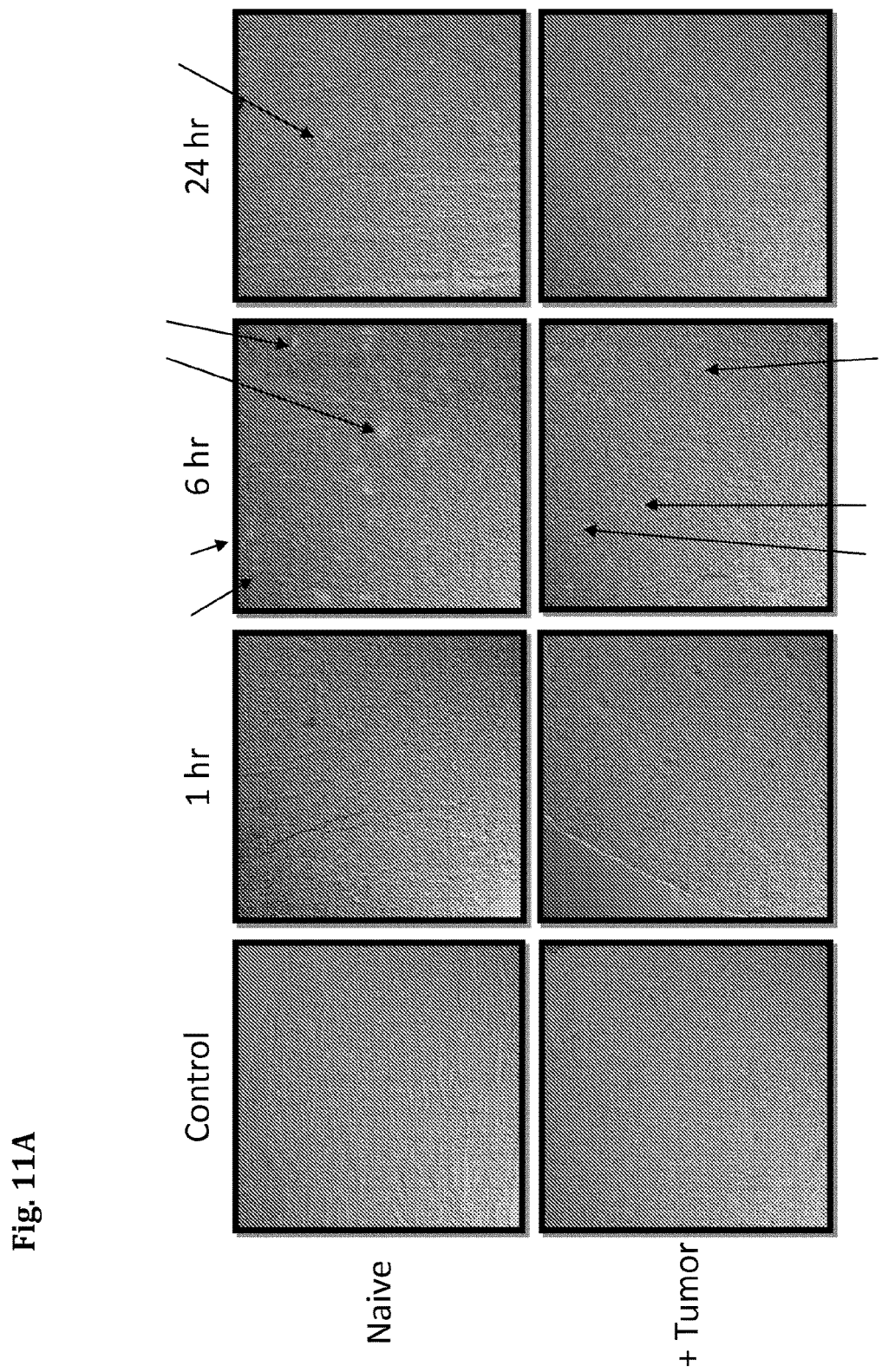

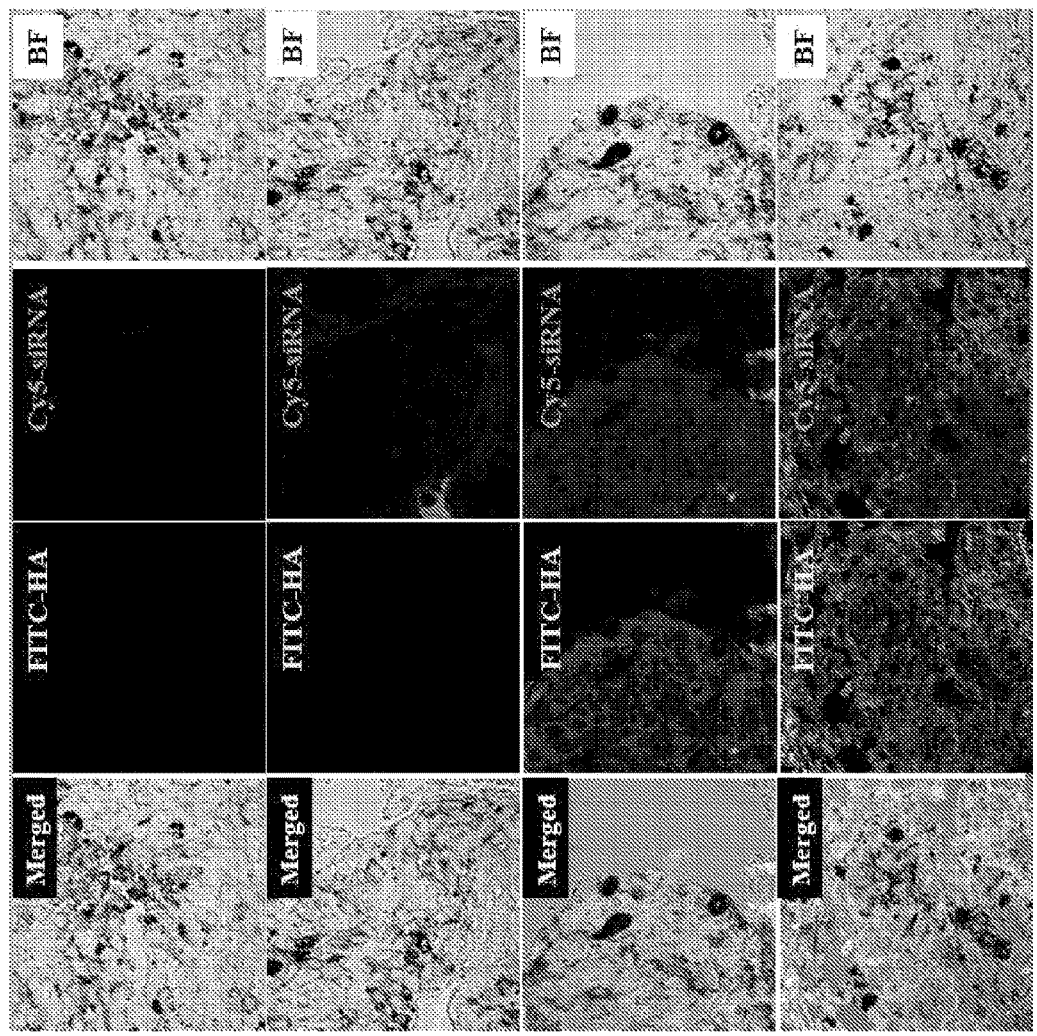
Fig. 19A  Control Mouse №12 4F Magnification x40 Zoom 2
Fig. 19B  1 hour Mouse №2 1F Magnification x40 Zoom 2
Fig. 19C  3 hours Mouse №6 2F Magnification x40 Zoom 2
Fig. 19D  7 hours Mouse №7 3F Magnification x40 Zoom 2

LIPIDATED GLYCOSAMINOGLYCAN PARTICLES FOR THE DELIVERY OF NUCLEIC ACIDS

FIELD OF THE INVENTION

The present invention relates to compositions comprising lipidated glycosaminoglycan particles (also known as gagomers), methods for their preparation and uses thereof for the efficient in-vivo and in-vitro delivery of nucleic acids, such as, siRNA molecules.

BACKGROUND OF THE INVENTION

Efficient delivery of a nucleic acid to a desired target site has been the focus of many intense studies. Once introduced to the target site, the nucleic acid, may exert, directly or indirectly, a biological effect in the target site. In some instances, the delivery of the nucleic acid may take use of carriers that are designed to deliver the nucleic acid to the target site. Exemplary nucleic acids that may be delivered to a target site include deoxyribonucleotides nucleic acid (DNA) and ribonucleotides nucleic acids (RNA), such as, for example, siRNA, miRNA, shRNA, Antisense RNA (AS-RNA), and the like.

RNA interference (RNAi) is an endogenous cellular mechanism of gene silencing. RNAi is carried out by double-stranded RNA (dsRNA) that suppress the expression of specific genes with complementary nucleotide sequences either by degrading specific messenger RNA (mRNA) or by blocking mRNA translation. RNAi can be also activated exogenously by expressing short hairpin RNA (shRNA) with viral vectors, or by incorporating synthetic small interfering RNA (siRNA) directly into the cell cytoplasm. siRNAs are chemically synthesized double stranded RNAs (dsRNAs) of 19-23 base pairs with 2-nucleotides unpaired in the 5'-phosphorylated ends and unphosphorylated 3'-ends. Inside the cell cytoplasm, siRNAs are incorporated into RNA induced silencing complex (RISC), a complex that separates the strands of the RNA duplex and discards the sense strand. The antisense RNA strand then guides RISC to anneal and cleave the target mRNA or block its translation. By recycling the target mRNA, the RISC complex incorporating the anti-sense strand may show a therapeutic effect for up to days in dividing cells and for several weeks in non-dividing cells. Furthermore, repeated administration of siRNAs can result in stable silencing of its target. However, despite this promise, utilizing siRNAs as therapeutics is not a trivial task. For example, due to the large molecular weight (~13 kDa) and the net negative charge, the efficiency with which naked siRNAs molecules cross the plasma membrane and enter the cell cytoplasm is usually very low. When injected intravenously, in addition to rapid renal clearance and susceptibility to degradation by RNAses, unmodified naked siRNAs are recognized by Toll-like receptors (TLRs). This often stimulates the immune system and provokes interferon response, complement activation, cytokine induction, and coagulation cascades (Reviewed by Peer D.). Beside the undesired immune activation, those effects can suppress gene expression globally, generating off-target and misinterpreted outcomes.

For in-vitro or ex-vivo delivery of siRNA to cells, conventional transfection methods are generally used (reviewed by Weinstein and Peer). In-vivo delivery of siRNA can be classified into two groups: localized or systemic. Local delivery of siRNAs has been demonstrated in various animal models and is employed in several ongoing clinical trials. Based on local injections of naked or cationic lipid/polymer-formulated siRNAs, this method of delivery is mainly suitable for mucosal diseases, subcutaneous tissues, intraocular injections to the vitreous body of the eye, and the like. Systemic delivery of siRNAs provides additional complications. Whereas cellular and local delivery deal with the need for internalization, release, and accumulation of the siRNAs in the cell cytoplasm, systemic delivery in an entire animal enforces additional hurdles such as, for example, the siRNAs interaction with blood components (which is a common complication using cationic liposomes due to the electrostatic interaction of the positive charge of the liposome with the generally negative charge of serum proteins), entrapment within capillaries, uptake by the reticuloendothelial cells, degradation by RNAses, anatomical barriers (such as the liver, spleen and filtration by the kidneys), immune stimulation, extravasation from blood vessels to target tissues, permeation within the tissue, and the like.

Various methods and carriers have been suggested over the years for systemic delivery of siRNA molecules. The methods and carriers include passive delivery of the siRNA or targeted delivery of the siRNA. Exemplary carriers described in the art include: Stable nucleic acid-lipid particles (SNALP), neutral liposomes, lipidoid containing liposomes, atelocollagen, cholesterol-siRNA, dynamic polyconjugates, PEI nanoplexs, antibody-protamine fusion proteins, aptamer-siRNAs, targeted cationinc liposomes and cyclodextrin containing polycation (CDP) (reviewed by Manjunath and Dykxhoorn; and Weinstein and Peer.)

Some of the siRNA carriers described in the art make use of hyaluronic acid that may be used as component of the particle and/or as a targeting moiety. For example: A publication by Taetz et. al., is directed to Hyaluronic acid modified DOTAP/DOPE liposomes for the targeted delivery of antitelomerase siRNA to CD44 Expressing Lung cancer cells. A publication by Lee. et. al. is directed to target specific intracellular delivery of siRNA using degradable hyaluronic acid nanogels. A publication by Choi et. al., is directed to self assembled hyaluronic acid nanoparticles for active tumor targeting. A publication by Peer et. al., is directed to Systemic Leukocyte-Directed siRNA Delivery Revealing Cyclin D1 as an Anti-Inflammatory Target. For example, PCT patent application publication no. WO 2011/013130 is directed to cell targeting nanoparticles comprising polynucleotide agents and uses thereof. Additionally, U.S. Pat. No. 7,544,374 is directed to lipidated glycosaminoglycan particles and their use in drug and gene delivery for diagnosis and therapy.

Nevertheless, the carriers described in the art, including carriers making use of hyaluronic acid do not address all the hurdles associated with a successful delivery of siRNA to its target cell, and in particular, in-vivo delivery.

There is thus a need in the art for improved carrier compositions for the efficient and specific delivery of siRNA into a desired target site, wherein the carrier compositions are stable, have a long shelf life, biodegradable, amenable to industrial production processes, have high encapsulating capacity, non toxic, avoid induction of immune responses, provide enhanced protection (stability and integrity) to the siRNA encapsulated therein and are able to efficiently deliver in-vitro and in-vivo, the siRNA to its target site, such that the siRNA is able to efficiently exert a desired effect.

SUMMARY

According to some embodiments, there is provided an improved lipidated glycosaminoglycan composition (Gagomer) which is used as an effective and efficient in-vivo and in-vitro delivery system of nucleic acid molecules, such as, for example, siRNA molecules.

According to some embodiments, the present invention rely at least in part on the surprising and unexpected finding that modifications in the composition of the lipids used for the preparation of the lipidated glycosaminoglycan particles, modifications in methods of their preparation, modification in the ratios between the various components of the Gagomer as well as an association between various components of the Gagomer particles and the nucleic acid molecules (such as for example, siRNA molecules), encapsulated therein, unexpectedly provide enhanced Gagomer composition which is extremely useful as delivery system for nucleic acid molecules in general and siRNA molecules in particular, both for in vitro and in-vivo applications. The enhanced Gagomer composition of the present invention exhibits various improvements over previously described Gagomer compositions. For example, the enhanced Gagomer composition of the present invention exhibits improved stability (shelf life), a defined structure and a uniform size distribution and charge. Furthermore, the enhanced Gagomer composition of the present invention are amenable to industrial production processes which are cost effective and may further be sterilized by conventional sterilization processes. Moreover, the enhanced Gagomer composition of the present invention exhibits high efficiency of encapsulation of nucleic acid molecules as well as high loading capacity (that is, number/amount of nucleic acid that a Gagomer may effectively carry). Additionally, the enhanced Gagomer composition of the present invention is able to provide enhanced protection to the nucleic acid molecules encapsulated within the Gagomer particles. In addition, the enhanced Gagomer composition of the present invention is not immunotoxic to cells nor does it elicit immune response in isolated human peripheral blood mononuclear cells (PBMCs) and upon in-vivo administration. The enhanced properties of the Gagomer compositions of the present invention are critical parameters for an effective, non-toxic and useful delivery system of nucleic acids.

Further, in another unexpected finding, the enhanced Gagomer composition of the present invention exhibit an unexpected weight ratio between the lipid components of the Gagomer particles and the nucleic acid (such as, for example, siRNA) encapsulated therein. For example, a higher lipid to siRNA weight ratio, provides an improved biological effect of the siRNA on its target. Furthermore, as demonstrated herein, there is no direct correlation between the level of the siRNA and the biological effect exerted thereby.

According to some embodiments, there is provided a composition comprising water insoluble lipidated glycosaminoglycan particles comprising a plurality of lipids forming a particulate lipid composition, and a nucleic acid encapsulated within the particles, wherein the weight ratio of the nucleic acid to lipids is less than 1:1.

In some embodiments, the plurality of lipids may be selected from a cationic lipid, and a lipid having a primary amino group. The cationic lipid may be selected from, but not limited to: monocationic lipid N-[1-(2,3-Dioleoyloxy)]-N,N,N-trimethylammonium propane (DOTAP), BCAT (O-(2R-1 2-di-O—(I'Z,9'Z-octadecadienyl)-glycerol)-3-N-(bis-2-aminoethyl)-carbamate), BGSC (Bis-guanidinium-spermidine-cholesterol), BGTC (Bis-guanidinium-tree-cholesterol), CDAN (N'-cholesteryloxycarbony 1-3,7-diazanonane-1,9-diamine), CHDTAEA (Cholesteryl hemidithiodiglycolyl tris(amin(ethyl)amine), DCAT (O-(1, 2-di-O-(9'Z-octadecenyl)-glycerol)-3-N-(bis-2-aminoethyl)-carbamate), DC-Chol (3β-[N—(N',N'-Dimethylainin (ethyl)carbamoyl cholesterol), DLKD (O,O'-Dilauryl N-lysylaspartate), DMKD (O,O'-Dimyristyl N-lysylaspartate), DOG (Diolcylglycerol, DOGS (Dioctadecylamidoglycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethylammonium chloride), DPPES (Di-palmitoyl phosphatidyl ethanolamidosperminc), DDAB and DODAP. Each possibility is a separate embodiment.

The lipid having a primary amino group (Phosphatidylethanolamines) may be selected from, but not limited to: 1,2-dilauroyl-L-phosphatidyl-ethanolamine (DLPE),1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE) Biotin-Phosphatidylethanolamine, 1,2-Dimyristoyl-sn-glycero-3-phosphoethanolamine (DMPE), Dipalmitoylphosphatidylethanolamine (DPPE)). Each possibility is a separate embodiment.

In further embodiments, the plurality of lipids may further include (in addition to the cationic lipid and the lipid having a primary amino group) a membrane stabilizing lipid that may be selected from, but not limited to: cholesterol, phospholipids (such as, for example, phosphatidylcholine, phosphatidylethanolamine, phosphatidylinositol, phosphatidylserine, phosphatidylglycerol, diphosphatidylglycerols), cephalins, sphingolipids (sphingomyelins and glycosphingolipids), and glycoglycerolipids. Each possibility is a separate embodiment.

According to further embodiments, the glycosaminoglycan may be selected from, but not limited to: hyaluronic acid, Chondroitin sulfate, Dermatan sulfate, Keratan sulfate, Heparin, Heparan sulfate, as well as fragments, salts, and mixtures thereof. In some embodiments, the hyaluronic acid may be selected from, but not limited to: high molecular weight hyaluronic acid (for example, in the range of about $MW=3.1\times10^5$-$1.5\times10^6$ Da).

According to some embodiments, the particulate lipid composition may have particle size in the range of about 10-200 nm.

In further embodiments, the nucleic acid may be selected from DNA, RNA, modified forms thereof, and combinations thereof. In some embodiments, the RNA may be selected from siRNA, miRNA, antisense RNA, or combinations thereof.

In additional embodiments, the weight ratio between the plurality of lipids and the nucleic acid is 2:1. In some embodiments, the weight ratio between the plurality of lipids and the nucleic acid is 5:1. In some embodiments, the weight ratio between the plurality of lipids and the nucleic acid is 10:1.

In some embodiments, the cationic lipid is not DOTMA (N'[1-(2,3-Dioleyloxy)propyl]-N,N,N-trimethylammonium chloride).

In some embodiments, the lipidated glycosaminoglycan particles (gagomers) have a particle size in the range of over about 50 nm. In some embodiments, the lipidated glycosaminoglycan particles (gagomers) have a particle size in the range of over about 100 nm. In some embodiments, the lipidated glycosaminoglycan particles (gagomers) have a particle size in the range of over about 200 nm. In some embodiments, the lipidated glycosaminoglycan particles (gagomers) have a particle size in the range of over about 500 nm. In some embodiments, the lipidated glycosaminoglycan particles (gagomers) have a particle size in the range of over about 750 nm. In some embodiments, the lipidated glycosaminoglycan particles (gagomers) have a particle size in the range of over about 1000 nm. In some embodiments, the lipidated glycosaminoglycan particles (gagomers) have a particle size in the range of over about 1500 nm. In some embodiments, the lipidated glycosaminoglycan particles (gagomers) have a particle size in the range of over about 2000 nm. In some embodiments, the lipidated glycosaminoglycan particles (gagomers) have a particle size in the range of over about 2500 nm. In some embodiments, the lipidated glycosaminoglycan particles (gagomers) have a particle size in the range of over about 3000 nm. In some embodiments, the lipidated glycosaminoglycan particles (gagomers) have a particle size in the range of over about 3500 nm. In some embodiments, the lipidated glycosaminoglycan particles (gagomers) have a particle size in the range of over about 4000 nm. In some embodiments, the lipidated glycosaminoglycan particles (gagomers) have a particle size in the range of over about 4500 nm. In some embodiments, the lipidated glycosaminoglycan particles (gagomers) have a particle size in the range of over about 5000 nm. In some embodiments, the lipidated glycosaminoglycan particles (gagomers) have a particle size in the range of over about 500 nm. In some embodiments, the lipidated glycosaminoglycan particles (gagomers) have a particle size in the range of about 50 nm-12 micron. In some embodiments, the lipidated glycosaminoglycan particles (gagomers) have a particle size in the range of about 500 nm-5 micron.

In further embodiments, the composition may further include a targeting moiety.

In additional embodiments, the particles may be adapted to deliver the nucleic acid to a target site. The target site may be selected from a cell, a tissue, an organ, and a microorganism.

According to some embodiments, there is provided a pharmaceutical composition comprising the lipidated glycosaminoglycan particles in a dosage form suitable for administration via a route selected from oral, parenteral and topical.

According to additional embodiments, the composition may be in the form of freeze dried particles.

According to exemplary embodiments, the composition comprises DOTAP, DLPE and cholesterol.

According to some embodiments, there is provided a method for treatment of cancer in a subject in need thereof, the method comprising administering to the subject a composition comprising the water insoluble lipidated glycosaminoglycan particles comprising a plurality of lipids forming a particulate lipid composition, and a nucleic acid encapsulated within the particles, wherein the weight ratio of the nucleic acid to lipids is less than 1:1, or a pharmaceutical composition comprising the same. In some embodiments, the nucleic acid In further embodiments, the nucleic acid may be selected from DNA, RNA, modified forms thereof, and combinations thereof. In some embodiments, the RNA may be selected from siRNA, miRNA, shRNA, antisense RNA, or combinations thereof.

According to some embodiments, there is provided a method for the preparation of a lipidated glycosaminoglycan composition encapsulating a nucleic acid, the method comprising the steps of:

a) forming a particulate lipid composition comprising the steps of:
   i) mixing one or more lipids in an organic solvent at a desired ratio and forming a homogeneous lipid mixture;
   ii) suspending the lipid mixture in an aqueous buffer and obtaining a desired particle size by sequential filtration of the lipid suspension in a heated lipid extruder;
b) activating of a glycosaminoglycan comprising:
   i) dissolving a glycosaminoglycan in an acidic buffer and adding a crosslinker to form an activated glycosaminoglycan; and
c) forming the lipidated glycosaminoglycan composition by the steps of:
   i) incubating the lipid composition of step a) with the nucleic acid; and
   ii) adding the activated glycosaminoglycan of step b) to the mixture.

According to some embodiments, the lipid particles have a particle size of about 50-200 nm.

In further embodiments, in step a) of the method for the preparation of the lipidated glycosaminoglycan composition, the organic solvent may be evaporated from the lipid mixture to form a lipid film.

In additional embodiments, the method for the preparation of the lipidated glycosaminoglycan composition may further include freeze drying the lipid particles.

In some embodiments, the plurality of lipids used in the method for the preparation of the lipidated glycosaminoglycan composition may be selected from a cationic lipid, and a lipid having a primary amino group. The cationic lipid may be selected from, but not limited to: monocationic lipid N-[1-(2,3-Dioleoyloxy)]-N,N,N-trimethylammonium propane (DOTAP), BCAT (O-(2R-1 2-di-O—(I'Z,9'Z-octadecadienyl)-glycerol)-3-N-(bis-2-aminoethyl)-carbamate), BGSC (Bis-guanidinium-spermidine-cholesterol), BGTC (Bis-guanidinium-tree-cholesterol), CDAN (N'-cholesteryloxycarbony 1-3,7-diazanonane-1,9-diamine), CHDTAEA (Cholesteryl hemidithiodiglycolyl tris(amin(ethyl)amine), DCAT (O-(1,2-di-O-(9'Z-octadecenyl)-glycerol)-3-N-(bis-2-aminoethyl)-carbamate), DC-Chol (3β-[N—(N',N'-Dimethylainin(ethyl)carbamoyl cholesterol), DLKD (O,O'-Dilauryl N-lysylaspartate), DMKD (O,O'-Dimyristyl N-lysylaspartate), DOG (Diolcylglycerol), DOGS (Dioctadecylamidoglycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethylammonium chloride), DPPES (Di-palmitoyl phosphatidyl ethanolamidosperminc), DDAB, DODAP and combinations thereof. Each possibility is a separate embodiment.

In some embodiments, the cationic lipid is not DOTMA (N'[1-(2,3-Dioleyloxy)propyl]-N,N,N-trimethylammonium chloride).

In some embodiments, the lipid having a primary amino group (Phosphatidylethanolamine) may be selected from, but not limited to: 1,2-dilauroyl-L-phosphatidyl-ethanolamine (DLPE),1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE) Biotin- Phosphatidylethanolamine, 1,2-Dimyristoyl-sn-glycero-3-phosphoethanolamine (DMPE), Dipalmitoylphosphatidylethanolamine (DPPE)), and combinations thereof. Each possibility is a separate embodiment.

In further embodiments, the lipids used in the method for the preparation of the lipidated glycosaminoglycan composition may further include (in addition to the cationic lipid and the lipid having a primary amino group), membrane stabilizing lipids that may be selected from, but not limited to: cholesterol, phospholipids (such as, for example, phosphatidylcholine, phosphatidylethanolamine, phosphatidylinositol, phosphatidylserine, phosphatidylglycerol, diphosphatidylglycerols), cephalins, sphingolipids (sphingomyelins and glycosphingolipids), glycoglycerolipids and combinations thereof. Each possibility is a separate embodiment.

According to further embodiments, the glycosaminoglycan used in the method may be selected from, but not limited to: hyaluronic acid, Chondroitin sulfate, Dermatan sulfate, Keratan sulfate, Heparin, Heparan sulfate, as well as fragments, salts, and mixtures thereof. The hyaluronic acid may be selected from, but not limited to: high molecular weight hyaluronic acid (for example, in the range of about MW=$3.1 \times 10^5$-$1.5 \times 10^6$ Da).

In further embodiments, the nucleic acid encapsulated within the lipidated glycosaminoglycan composition may be selected from DNA, RNA, modified forms thereof, and combinations thereof. In some embodiments, the RNA may be selected from siRNA, miRNA, shRNA, antisense RNA, or combinations thereof.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 4 a pictogram demonstrating stability of siRNA encapsulated within an improved Gagomer composition.

FIG. 7A—relative Aha 1 expression; FIG. 7B—relative Kif11 expression; FIG. 7C—relative Aha1 gene expression;

FIG. 8A—mice melanoma B16-F10 cell line. FIG. 8B—human LLC-D122 cell line;

FIG. 9A—concentration of IL-6, FIG. 9B—concentration of IL-10; FIG. 9C—concentration of INFγ; FIG. 9D—concentration of TNFα;

FIG. 10A—concentration of IL-6 (pg/mL); FIG. 10B—concentration of TNF-α (pg/mL); FIG. 10C—concentration of INFγ (pg/mL);

FIGS. 11A-11H—microscopic pictograms of cryosection preparations of various tissues obtained from naïve or tumor bearing mice injected with Cy5 labeled siRNA encapsulated within the improved Gagomer composition. FIGS. 11A-B: Liver; FIG. 11C-D: Spleen; FIGS. 11E-F: Kidney; FIGS. 11G-H: Lungs;

FIG. 12A—confocal microscope images; FIG. 12B—H&E histological staining; FIG. 12C—high resolution spectral fluorescent microscopic images;

FIG. 14A—levels of SGOT/AST (IU/L). FIG. 14B—levels of SGPT/AST (IU/L). FIG. 14C—Cholesterol (mg/dL). FIG. 14D—levels of triglycerides (mg/dL);

FIG. 15A—concentration of IL-6 (pg/ml). FIG. 15B—concentration of IL-10 (pg/ml). FIG. 15C—IFNγ (pg/ml). FIG. 15D—concentration of TNFα (pg/ml); FIG. 16A-Lungs; FIG. 16B—Liver; FIG. 16C—Kidney; FIG. 16D—Spleen.

FIG. 17A: Bar graphs showing the relative expression level of Aha1 mRNA in Liver, Lung and tumor tissues, treated with the indicated Gagomer-siRNA compositions (0.4 mg/kg), or not treated. FIG. 17B: bar graphs showing dose and time effect of the Gagomer-siRNA compositions on the relative expression of the Aha1 mRNA in tumor extracts. Time points tested were 24 hours and 48 hours after administration of the Gagomer-siRNA compositions. Doses of Gagomer-siRNA compositions tested were 0.4 mg/kg and 2.0 mg/kg.

FIG. 18A shows macroscopic pictogram of a ventral view of the retrieved lungs; FIG. 18B shows macroscopic pictogram of a dorsal view. Arrows indicate identified metastatic colonization (identified as black dots). FIG. 18C shows a pictogram of histological preparation of the lungs from a sacrificed animal, 10 days post B16-F10 cell inoculation, which demonstrates signs of subpleural aggregation with accompanying parenchymal invasion.

FIGS. 19A-D—microscopic pictograms of cryosection preparations of lung metastases obtained from C57BL mice administered (IV) with B16-F10 cells, which induce lung metastatic. The mice were injected with Cy5 labeled siRNA encapsulated within the improved Gagomer composition, having an HA moiety labeled with FITC. The mice were sacrificed at various time points after administration of the Gagomer-siRNA composition, and cryosections of the lung metastasis were fluorescently labeled with Cy5 label (originally shown as red) and FITC (originally shown as green). FIG. 19A—lung metastases cryosection from control mouse (not administered with Gagomer-siRNA composition). FIG. 19B—lung metastases cryosection from mice sacrificed one hour after administration with the Gagomer-siRNA composition. FIG. 19C—lung metastases cryosection from mice sacrificed three hours after administration with the Gagomer-siRNA composition. FIG. 19D—lung metastases cryosection from mice sacrificed seven hours after administration with the Gagomer-siRNA composition. For all figures—right hand panel (BF)—bright field image, second to right panel (Cy5-siRNA)—Cy5 label (Originally red), second to left panel (FITC-HA)—FITC labeling (originally green), left hand panel (Merged)—image showing merged images of Cy5 and FITC labeling (originally yellow).

DETAILED DESCRIPTION

Definitions

Figure 1:
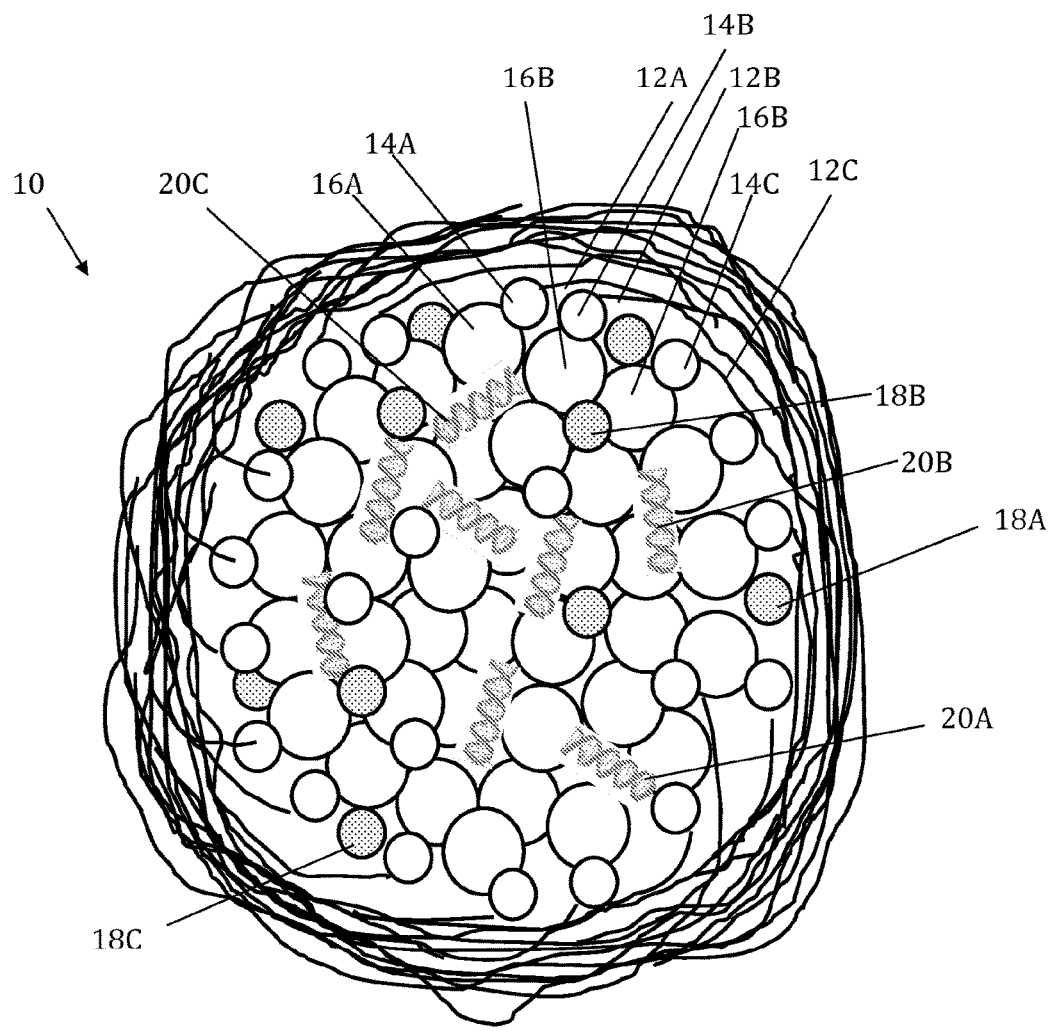
FIG. 1—a schematic illustration of a Gagomer structure, according to some embodiments.

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "nucleic acid", "nucleic acid molecules" "oligonucleotide", "polynucleotide", and "nucleotide" may interchangeably be used herein. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, Antisense RNA, and the like. Each possibility is a separate embodiment. The terms further include oligonucleotides composed of naturally occurring bases, sugars, and covalent internucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "plurality" as used herein is directed to include more than one component.

The terms "Glycosaminoglycans" (GAGs) or "mucopolysaccharides" are directed to long unbranched polysaccharides consisting of a repeating disaccharide unit. The repeating unit may include a hexose (six-carbon sugar) or a hexuronic acid, linked to a hexosamine. Members of the glycosaminoglycan family may vary in the type of hexosamine, hexose or hexuronic acid unit they contain (for example, glucuronic acid, iduronic acid, galactose, galactosamine, glucosamine) and in the geometry of the glycosidic linkage. The term Glycosaminoglycan includes natural, synthetic, or semisynthetic Glycosaminoglycan molecules. Exemplary Glycosaminoglycans include such Glycosaminoglycans as, but not limited to: Chondroitin sulfate, Dermatan sulfate, Keratan sulfate, Heparin, Heparan sulfate, Hyaluronan (also known as hyaluronic acid, hyaluronate, HA) and fragments, salts, and mixtures thereof. The term Glycosaminoglycan further includes Glycosaminoglycans that have been chemically modified by modifications such as, but not limited to: esterification, sulfation, polysulfation, and methylation. The glycosaminoglycans, except hyaluronic acid, are naturally in the form of a protein moiety bound covalently to a poly-saccharide moiety. Methods for hydrolyzing the protein-sugar bond are well known to those skilled in the art, both chemically and enzymatically.

The terms "HA" and "Hyaluronan" refer to Hyaluronic acid that can be in a free form, and in an attached form, such as an extracellular matrix component. The Term HA further relates to any of its hyaluronate salts, including, for example, sodium hyaluronate, potassium hyaluronate, magnesium hyaluronate, and calcium hyaluronate. HA polysaccharide consists of alternating N-acetyl-D-glucosamine and D glucuronic acid residues joined by alternating beta-1,3-glucuronidic and beta-1,4-glucosaminidic bonds. The HA may be of low molecular weight (for example, in the range of MW=$10^4$-$7.2\times10^4$) and/or of High molecular weight (for example, in the range of about MW=$3.1\times10^5$-$1.5\times10^6$ Da). The HA may be of varying chain length. Hyaluronic acid has a high affinity for the extracellular matrix and to a variety of tumors, including those of the breast, brain, lung, skin, and other organs and tissues. HA have high affinity of CD44 cellular receptors.

The term "Gagomer(s)" and "Gagomer composition" may interchangeably be used and are directed to particles of lipidated Glycosaminoglycan. In general, the Gagomers are bioadhesive biopolymers produced by cross-linking a lipid to a carboxylic acid-containing glycosaminoglycan. The terms "improved Gagomer", "enhanced Gagomer", "improved Gagomer composition" and "enhanced Gagomer composition" may interchangeably be used and are directed to include the Gagomer compositions of the present invention, as disclosed herein.

The terms "siRNA-Gagomer" and "Gagomer-siRNA" may interchangeably be used and are directed to the improved Gagomer of the present invention encapsulating siRNA molecules. The siRNA molecules may include, for example, but not limited to: short double stranded siRNA (for example in the length of 18-25 nucleotides). The siRNA molecules may be modified or non-modified. In some embodiments, all the siRNA molecules in the Gagomer are identical.

The term "construct", as used herein, refers to an artificially assembled or isolated nucleic acid molecule which may include one or more nucleic acid sequences, wherein the nucleic acid sequences may include coding sequences (that is, sequence which encodes an end product), regulatory sequences, non-coding sequences, or any combination thereof. The term construct includes, for example, vector but should not be seen as being limited thereto.

"Expression vector" refers to constructs that have the ability to incorporate and express heterologous nucleic acid fragments (such as, for example, DNA), in a foreign cell. In other words, an expression vector comprises nucleic acid sequences/fragments (such as DNA, mRNA, tRNA, rRNA), capable of being transcribed. Many prokaryotic and eukaryotic expression vectors are known and/or commercially available. Selection of appropriate expression vectors is within the knowledge of those having skill in the art. In some exemplary embodiments, the expression vector may encode for a double stranded RNA molecule in the target site.

The term "expression", as used herein, refers to the production of a desired end-product molecule in a target cell. The end-product molecule may include, for example an RNA molecule; a peptide or a protein; and the like; or combinations thereof.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, virus cell, and the like. The cells may be selected from isolated cells, tissue cultured cells, cell lines, cells present within an organism body, and the like.

As referred to herein, the term "target site" refers to the location in which the nucleic acid is directed to and/or the site in which the nucleic acid is to exert its biological effect. In some exemplary embodiments, the target site is a cell that may be selected from, but not limited to: a culture cell (primary cell or cell-line derived cell), and a cell within an organism body; a tissue, an organ, a microorganism (such as, for example, virus, bacteria, parasite), and the like. The organism may be any organism, such as, but not limited to: a mammal, such as human or an animal, an animal which is not a mammal (such as, for example, avian, Fish, and the like), and the like. In some exemplary embodiments, the target site is a subcellular location or cellular organelle (such as, for example, nucleus, cytoplasm, and the like).

The term "treating" and "treatment" as used herein refers to abrogating, inhibiting, slowing or reversing the progression of a disease or condition, ameliorating clinical symptoms of a disease or condition or preventing the appearance of clinical symptoms of a disease or condition. The term "preventing" is defined herein as barring a subject from acquiring a disorder or disease or condition.

The term "treatment of cancer" is directed to include one or more of the following: a decrease in the rate of growth of the cancer (i.e. the cancer still grows but at a slower rate); cessation of growth of the cancerous growth, i.e., stasis of the tumor growth, and, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like.

As used herein, the term "about" refers to +/−10%.

According to some embodiments of the present invention, there is provided an improved Gagomer composition comprising an activated glycosaminoglycan and a combination of lipids linked thereto, wherein the Gagomer particle encapsulates nucleic acid molecules and wherein the Gagomer particle is used as a delivery system to deliver the nucleic acid molecules to a desired target site. The target site may include any target site, such as, but not limited to: a cell, a tissue, an organ, a microorganism, and the like. The target site may be an in-vivo or in-vitro target site.

According to some exemplary embodiments, the improved Gagomer composition comprises a combination of one or more lipids. The plurality of lipids in the composition may be of natural or synthetic source and may be selected from, but not limited to: cationic lipids, lipids having a primary amino group and membrane stabilizing lipids (membrane stabilizers). For example, the cationic lipids may be selected from, but not limited to: The cationic lipid may be selected from, but not limited to: monocationic lipid N-[1-(2,3-Dioleoyloxy)]-N,N,N-trimethylammonium propane (DOTAP), BCAT (O-(2R-1 2-di-O—(I'Z,9'Z-octadecadienyl)-glycerol)-3-N-(bis-2-aminoethyl)-carbamate), BGSC (Bis-guanidinium-spermidine-cholesterol), BGTC (Bis-guanidinium-tree-cholesterol), CDAN (N'-cholesteryloxycarbony 1-3,7-diazanonane-1,9-diamine), CHDTAEA (Cholesteryl hemidithiodiglycolyl tris(amin(ethyl)amine), DCAT (O-(1,2-di-O-(9'Z-octadccenyl)-glycerol)-3-N-(bis-2-aminoethyl)-carbamate), DC-Chol (3β-[N—(N',N'-Dimethylainin(ethyl)carbamoyl cholesterol), DLKD (O,O'-Dilauryl N-lysylaspartate), DMKD (O,O'-Dimyristyl N-lysylaspartate), DOG (Diolcylglycerol, DOGS (Dioctadecylamidoglycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethylammonium chloride), DPPES (Di-palmitoyl phosphatidyl ethanolamidospermine), DDAB (Dimethyldioctadecylammonium bromide) and DODAP (1,2-dioleoyl-3-dimethylammonium-propane) and any salts thereof and any combinations thereof. For example, The lipid having a primary amino group (Phosphatidylethanolamines) may be selected from, but not limited to: 1,2-dilauroyl-L-phosphatidyl-ethanolamine (DLPE), 1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine (DMPE), Dipalmitoylphosphatidylethanolamine (DPPE) and combinations thereof. For example, the membrane stabilizing lipids may be selected from, but not limited to: cholesterol, phospholipids (such as, for example, phosphatidylcholine, phosphatidylethanolamine, phosphatidylinositol, phosphatidylserine, phosphatidylglycerol, diphosphatidylglycerols), cephalins, sphingolipids (sphingomyelins and glycosphingolipids), glycoglycerolipids, and combinations thereof. Each possibility is a separate embodiment.

In some embodiments, the lipid is not DOTMA (N'[1-(2, 3-Dioleyloxy)propyl]-N,N,N-trimethylammonium chloride).

According to some embodiments, the ratio between the various lipids in the lipids combination (particulate lipid composition) of the Gagomer may vary. In some embodiments, the ratio is a molar ratio. In some embodiments, the ratio is a weight ratio. In some embodiments, each of the lipid groups may be at molar ratio/a weight ratio of about 1%-99%.

According to some exemplary embodiments, the ratio between the various lipids may be determined such that it provides maximal effectiveness with respect to the nucleic acids encapsulated within the Gagomer. Maximal effectiveness may include such exemplary parameters as, but not limited to: stability of the Gagomer, protection of the nucleic acid encapsulated within the Gagomer, targeted delivery of the nucleic acid to a desired target site, maximal biological effect exerted by the nucleic acid in the target site; highest effective loading capacity of the nucleic acid in the Gagomer, and the like, and combinations thereof.

According to some exemplary embodiments, when the lipid composition comprises cationic lipids, membrane stabilizing lipids and/or lipids having a primary amino group, each of the lipids group may be at molar ratio or a weight ratio of about 1%-99%. For example, the cationic lipids may be 10-90% of the lipid composition; the lipids having a primary amino group may be 1-50% of the lipid composition; and the membrane stabilizing lipids may be 10-90% of the lipid composition. The following are exemplary lipids compositions: 1. cationic lipids: 30-80%, lipids having a primary amino group: 5-25%, membrane stabilizing lipids: 10-50%; 2. cationic lipids: 50-70%, lipids having a primary amino group: 8-12%, membrane stabilizing lipids: 20-40%; 3. cationic lipids: 55-65%, lipids having a primary amino group: 9-11%, membrane stabilizing lipids: 25-35-50%.

According to some embodiments, the weight ratio between the nucleic acid and the lipid combination of the Gagomer, may also be adjusted so as to achieve maximal biological effect by the nucleic acid on the target site. As exemplified herein, it has been surprisingly and unexpectedly found that with respect to siRNA molecules, a high lipid to siRNA weight ratio provides improved biological effect. It has been unexpectedly found that there is no direct correlation between the level of siRNA and the biological effect. Without wishing to be bound to theory or mechanism, the lack of direct correlation between the level of siRNA and the biological effect may at least in part be attributed to the loading capacity of the target site, that is, overloading of the intracellular RNAi mechanism, which utilize the siRNA to exert the biological effect of inhibiting expression of a target within the target site, may result in diminished activity of the RNAi mechanism. Thus, in order to achieve a maximal response, the amount of siRNA delivered to the target site should overload the RNAi mechanism. Accordingly, the weight ratio of the siRNA to lipids is less than 1:1. For example, the weight ratio between the siRNA and the Lipids composition may be 1:1. For example, the weight ratio between the siRNA and the Lipids composition may be 1:2. For example, the weight ratio between the siRNA and the Lipids composition may be 1:5. For example, the weight ratio between the siRNA and the Lipids composition may be 1:10. For example, the weight ratio between the siRNA and the Lipids composition may be 1:20.

According to some embodiments, the glycosaminoglycan used for the preparation of the improved Gagomer may include any unmodified and/or modified glycosaminoglycan as well as modified glycosaminoglycan. In some embodiments, the glycosaminoglycan may be selected from, but not limited to: HA, Chondroitin sulfate, Dermatan sulfate, Keratan sulfate, Heparin, Heparan sulfate, and salts thereof. The glycosaminoglycan may be of varying lengths. In some exemplary embodiments, the glycosaminoglycan is a high molecular weight (HMW) HA. In some exemplary embodiments, the glycosaminoglycan is a low molecular weight (LMW) HA. In other exemplary embodiments, the glycosaminoglycan is a combination of HA having varying molecular weights. According to some embodiments, the Glycosaminoglycan may be activated prior to being reacted with other components of the Gagomer. For example, activation may include, but not limited to, acidifying the glycosaminoglycan, adding a crosslinker to the glycosaminoglycan, and the like. In exemplary embodiments, the crosslinker may be a carbodiimide selected from, but not limited to: EDC (EDAC, EDCI, 1-ethyl-3-(3-dimethylaminopropyl)carbodiimide), DCC (N,N'-dicyclohexylcarbodiimide), and DIC (N,N'-diisopropylcarbodiimide).

According to further embodiments, additional molecules/moieties may be attached first to the glycosaminoglycan, prior to being reacted with the lipids composition. The additional molecules may be, for example, antibodies, folate, porphyrins, or lectins, and may be used for targeting of the improved Gagomer to specific target sites. In additional embodiments, the additional molecules/moieties may be attached to the Gagomer.

In some embodiments, the lipidated glycosaminoglycan particles (gagomers) have a particle size in the range of over about 50 nm. In some embodiments, the lipidated glycosaminoglycan particles (gagomers) have a particle size in the range of over about 100 nm. In some embodiments, the lipidated glycosaminoglycan particles (gagomers) have a particle size in the range of over about 200 nm. In some embodiments, the lipidated glycosaminoglycan particles (gagomers) have a particle size in the range of over about 500 nm. In some embodiments, the lipidated glycosaminoglycan particles (gagomers) have a particle size in the range of over about 750 nm. In some embodiments, the lipidated glycosaminoglycan particles (gagomers) have a particle size in the range of over about 1000 nm. In some embodiments, the lipidated glycosaminoglycan particles (gagomers) have a particle size in the range of over about 1500 nm. In some embodiments, the lipidated glycosaminoglycan particles (gagomers) have a particle size in the range of over about 2000 nm. In some embodiments, the lipidated glycosaminoglycan particles (gagomers) have a particle size in the range of over about 2500 nm. In some embodiments, the lipidated glycosaminoglycan particles (gagomers) have a particle size in the range of over about 3000 nm. In some embodiments, the lipidated glycosaminoglycan particles (gagomers) have a particle size in the range of over about 3500 nm. In some embodiments, the lipidated glycosaminoglycan particles (gagomers) have a particle size in the range of over about 4000 nm. In some embodiments, the lipidated glycosaminoglycan particles (gagomers) have a particle size in the range of over about 4500 nm. In some embodiments, the lipidated glycosaminoglycan particles (gagomers) have a particle size in the range of over about 5000 nm. In some embodiments, the lipidated glycosaminoglycan particles (gagomers) have a particle size in the range of over about 500 nm. In some embodiments, the lipidated glycosaminoglycan particles (gagomers) have a particle size in the range of about 50 nm-12 micron. In some embodiments, the lipidated glycosaminoglycan particles (gagomers) have a particle size in the range of about 500 nm-5 micron.

In some embodiments, the improved Gagomer composition does not comprise DOTMA (N'[1-(2,3-Dioleyloxy)propyl]-N,N,N-trimethylammonium chloride). In some embodiments, the improved Gagomer composition is devoid of DOTMA (N'[1-(2,3-Dioleyloxy)propyl]-N,N,N-trimethylammonium chloride).

According to some embodiments, there is provided a method for the preparation of an improved Gagomer composition for the delivery of nucleic acids, the method comprising one or more of the following steps:

a) forming a particulate lipid composition: mixing one or more lipids in an organic solvent at a desired ratio; forming an homogenous lipid composition (for example, in the form a lipid film) by evaporation; dispersing (suspending) the lipid film in an appropriate buffer; obtaining a desired particle size (for example, in the size of 10-200 nm) by sequential lipid dispersion filtration in heated lipid extruder;

b) activation of glycosaminoglycan: dissolving a glycosaminoglycan in acidic buffer; adding a crosslinker to form an activated glycosaminoglycan;

c) Gagomer composition formation: the particulate lipid composition of step a) is incubated at a desired weight ratio with the nucleic acid for a period of time after which the activated glycosaminoglycan is added to form the improved Gagomer composition.

According to some embodiments, the method for the preparation of the improved Gagomer composition may include various modifications to finely adjust the components of the Gagomer, as well as the ratio between the components, so as to obtain the most effective Gagomer composition. The modifications may include, for example, such parameters as, but not limited to: the specific lipids used for the formation of the lipid composition, the ratio between the lipids of the lipid compositions, the identity of the nucleic acid to be encapsulated within the Gagomer, the ratio between the nucleic acid and the lipid composition, the specific glycosaminoglycan used, the ratio between the glycosaminoglycan and the lipid composition, the pH at which reactions are performed, the temperatures at which reactions are performed, the conditions at which the reactions are formed (with/without agitation), the time length of various steps, and the like, or any combination thereof.

According to exemplary embodiments, for the preparation of an improved Gagomer composition encapsulating siRNA molecules, the steps of the method may include at least the following specifically adjusted parameters to provide the most potent Gagomer for the delivery of siRNA: the particulate lipid composition may include 60% cationic lipid (that may include, for example, DOTAP), 30% membrane stabilizing lipid (that may include, for example, cholesterol) and 10% a lipid having a primary amino group (that may include, for example, DLPE); the lipid film may be dissolved at pH 9.0 Borate Buffer; the weight ratio between the siRNA and the lipid composition may be 1:10; the final step of incubation between the lipid composition-siRNA and the activated HA may be performed over night at 37° C., without agitation.

According to some embodiments, the method for the preparation of the improved Gagomers of the present invention may beneficially result in uniformly distributed lipid composition particle size, as further exemplified herein (Example 1).

In additional embodiments, in the formation of the Gagomer structure there is no formation of liposome, rather, the lipids composition is covalently attached to the glycosaminoglycan.

According to some embodiments, the improved Gagomers formed by the methods of the present invention may be lyophilized or dehydrated at various stages of formation. For example, the lipid film may be lyophilized after removing the solvent and prior to adding the nucleic acid. For example, the lipids-nucleic acid composition may be lyophilized and readily dehydrated. For example, the Gagomer (lipidated glycosaminoglycan encapsulating the nucleic acid) may be lyophilized and readily dehydrated.

According to some embodiments, the improved Gagomer compositions of the present invention exhibit high efficiency of encapsulation. In some exemplary embodiments, a single Gagomer may encapsulate about 7500 siRNA molecules, which is higher than the encapsulation capacity of other siRNA carriers known in the art.

Reference is now made to FIG. 1, which is a schematic illustration of a structure of an improved Gagomer encapsulating a nucleic acid molecule, according to some embodiments. As shown in FIG. 1, a Gagomer, such as, for example, Gagomer 10, is comprised of a combination of lipids, such as, for example, cationic lipid (shown, for example, as cationic lipids 16A-C in FIG. 1), lipids having a primary amino group (shown, for example, as lipids 14A-C in FIG. 1) and membrane stabilizing lipids (shown, for example, as membrane stabilizing lipids 18A-C in FIG. 1), which are linked/attached together to form particulate lipid composition, that may further be filter extruded to reduce their size to a desired size. To the particulate lipids composition, nucleic acid molecules (shown, for example, as nucleic acid molecules 20A-C in FIG. 1) are added. The negatively charged nucleic acid molecules may bind the positively charged cationic lipid in the lipids composition. Activated glycosaminoglycan molecules at varying length, having a carboxylic residue (shown, for example, as glycosaminoglycan molecules 12A-C in FIG. 1) are covalently cross linked to the primary amino groups of the lipids having the primary amino group, and wrap the lipid-nucleic acid complex to form a protective outer surface and to form the improved Gagomer structure. In addition to the covalent bonds which form between the activated glycosaminoglycan and the lipid having the primary amino group, electrostatic interactions form between the various constituents of the Gagomer, thereby further stabilize its structure and provide enhanced protection to the nucleic acid encapsulated therein. In some embodiments, the Gagomer structure is globular. The Gagomer structure does not necessarily form a sphere shape.

In some exemplary embodiments, the improved Gagomer presented in FIG. 1 may include the following components: the cationic lipid comprises DOTAP, the lipid having a primary amino group comprises DLPE, the membrane stabilizing lipid comprises Cholesterol, the nucleic acid molecules comprises double stranded siRNA molecules, and the glycosaminoglycan molecules comprises high molecular weight Hyaluronic acid (HA).

According to some embodiments, and without wishing to be bound to theory or mechanism, the formation of the improved Gagomer structure shown in FIG. 1 yields a reproducible and controlled structure which provides protection to the encapsulated nucleic acid from the surrounding environment and provides an effective delivery means to deliver the nucleic acid to the target site, wherein the nucleic acid may be released and exert its biological effect. The structure formed further provides high loading capacity of nucleic acid per each Gagomer. In some exemplary embodiments, a single Gagomer may encapsulate about 7500 siRNA molecules. In addition, as demonstrated below, upon addition of the nucleic acid and glycosaminoglycan to the lipid composition and the formation of the Gagomer, the Gagomer acquires a negative charge. This is particularly important for in-vivo delivery, whereby the Gagomer encapsulating the nucleic acid particle is not perceived by the organism body to be positively charged, thereby conferring a "stealth" modality to the Gagomer particle. Thus, the nucleic acid-Gagomer particle which does not have any exposed cationic lipids provides additional benefits to the particle as it prevents unwanted interactions with, for example, serum proteins which can form aggregates, it does not induce immune response and the outer HA prevents the particle from being identified as foreign particles, and hence, allows the particle to be an improved in-vivo delivery means of nucleic acids. In particular, the improved Gagomer composition prevents the known toxic effect exerted by cationic lipids upon in-vivo administration.

According to some embodiments, the improved Gagomer composition can be used in the treatment of various pathological conditions in an organism in need thereof.

According to some embodiments, the improved Gagomer composition may be administered as is. In some embodiments, the improved Gagomer composition may be administered in a solution. In some embodiments, the Gagomer composition may be formulated to a suitable pharmaceutical composition to be administered by any desired route of administration. Exemplary routes of administration include such routes as, but not limited to: topical, oral or parenteral. Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages. The pharmaceutical compositions may include the improved Gagomer, a pharmaceutical acceptable excipient, and, optionally, may include other medicinal agents, pharmaceutical agents, carriers, adjuvants, and the like. It is preferred that the pharmaceutically acceptable carrier be one which is inert to the nucleic acid encapsulated within the Gagomer and which has no detrimental side effects or toxicity under the conditions of use.

In some embodiments, injectable formulations for parenteral administration can be prepared as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, and the like. Aqueous injection suspensions may also contain substances that increase the viscosity of the suspension, including, for example, sodium carboxymethylcellulose, sorbitol, and/or dextran. Optionally, the suspension may also contain stabilizers. The parenteral formulations can be present in unit dose or multiple dose sealed containers, such as ampules and vials, and can be stored in a freeze-dried (lyophilized) condition requiring only the addition of the sterile liquid carrier, such as, for example, water, for injections immediately prior to use.

In other embodiments, for oral administration, a pharmaceutically acceptable, non-toxic composition may be formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions include solutions, suspensions, tablets, dispersible tablets, pills, capsules, powders, sustained release formulations and the like. Formulations suitable for oral administration can consist of liquid solutions such as effective amounts of the compound(s) dissolved in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, (such as, for example ethanol, benzyl alcohol, and the polyethylene alcohols), either with or without the addition of a pharmaceutically acceptable surfactant, suspending agents, or emulsifying agents.

In determining the dosages of the improved Gagomer composition to be administered, the dosage and frequency of administration is selected in relation to the pharmacological properties of the specific nucleic acid molecules encapsulated within the Gagomer.

In some exemplary embodiments, a Gagomer-siRNA may be used in the treatment of various pathological conditions, depending on the identity of the siRNA, the target site, and the like. Exemplary pathological conditions may be selected from, but not limited to: various types of cancer, various infections (such as, for example, viral infection, bacterial infection, fungal infection, and the like), autoimmune diseases, neurodegenerative diseases, inflammations (for example, inflammatory bowel diseases such as Crohn's disease, colitis, and the like), eye related syndromes and diseases, pulmonary related diseases, gastro-intestinal related syndromes and diseases, and the like.

In some exemplary embodiments, the improved Gagomers, either empty or encapsulating a nucleic acid (such as a Gagomer-siRNA composition) may be used for the treatment of cancer. Cancer is a disorder in which a population of cells has become, in varying degrees, unresponsive to the control mechanisms that normally govern proliferation and differentiation. Cancer refers to various types of malignant neoplasms and tumors, including metastasis to different sites. Non-limiting examples of cancers which can be treated by the improved Gagomers and/or the improved Gagomer-nucleic acid (such as Gagomer-siRNA) compositions are ovarian cancer, prostate cancer, breast cancer, skin cancer, melanoma, colon cancer, lung cancer, pancreatic cancer, gastric cancer, bladder cancer, Ewing's sarcoma, lymphoma, leukemia, multiple myeloma, head and neck cancer, kidney cancer, bone cancer, liver cancer and thyroid cancer. Specific examples of cancers include such types as, but not limited to: adenocarcinoma, adrenal gland tumor, ameloblastoma, anaplastic tumor, anaplastic carcinoma of the thyroid cell, angiofibroma, angioma, angiosarcoma, apudoma, argentaffinoma, arrhenoblastoma, ascites tumor cell, ascitic tumor, astroblastoma, astrocytoma, ataxia-telangiectasia, atrial myxoma, basal cell carcinoma, bone cancer, bone tumor, brainstem glioma, brain tumor, breast cancer, Burkitt's lymphoma, carcinoma, cerebellar astrocytoma, cervical cancer, cherry angioma, cholangiocarcinoma, a cholangioma, chondroblastoma, chondroma, chondrosarcoma, chorioblastoma, choriocarcinoma, colon cancer, common acute lymphoblastic leukemia, craniopharyngioma, cystocarcinoma, cystofibroma, cystoma, cytoma, cutaneous T-cell lymphoma, ductal carcinoma in situ, ductal papilloma, dysgerminoma, encephaloma, endometrial carcinoma, endothelioma, ependymoma, epithelioma, erythroleukaemia, Ewing's sarcoma, extra nodal lymphoma, feline sarcoma, fibroadenoma, fibrosarcoma, follicular cancer of the thyroid, ganglioglioma, gastrinoma, glioblastoma multiforme, glioma, gonadoblastoma, haemangioblastoma, haemangioendothelioblastoma, haemangioendothelioma, haemangiopericytoma, haematolymphangioma, haemocytoblastoma, haemocytoma, hairy cell leukemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angiofibroma, Kaposi sarcoma, kidney tumor, large cell lymphoma, leukemia, chronic leukemia, acute leukemia, lipoma, liver cancer, liver metastases, Lucke carcinoma, lymphadenoma, lymphangioma, lymphocytic leukemia, lymphocytic lymphoma, lymphocytoma, lymphoedema, lymphoma, lung cancer, malignant mesothelioma, malignant teratoma, mastocytoma, medulloblastoma, melanoma, meningioma, mesothelioma, metastatic cancer, Morton's neuroma, multiple myeloma, myeloblastoma, myeloid leukemia, myelolipoma, myeloma, myoblastoma, myxoma, nasopharyngeal carcinoma, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheochromocytoma, plasmacytoma, primary brain tumor, progonoma, prolactinoma, renal cell carcinoma, retinoblastoma, rhabdomyosarcoma, rhabdosarcoma, solid tumor, sarcoma, secondary tumor, seminoma, skin cancer, small cell carcinoma, squamous cell carcinoma, strawberry haemangioma, T-cell lymphoma, teratoma, testicular cancer, thymoma, trophoblastic tumor, tumourigenic, vestibular schwannoma, Wilm's tumor, or a combination thereof.

According to some embodiments, there is thus provided a method for the treatment of cancer, comprising the step of administration to a subject in need thereof a Gagomer or Gagomer-siRNA or a pharmaceutical compositions comprising the same. In some embodiments, there is provided a method for the treatment of cancer in a subject in need thereof, the method comprising administering to the subject the Gagomer-siRNA or a pharmaceutical compositions comprising the Gagomer-siRNA, thereby treating cancer in the subject. In some embodiments, there is provided the use of a Gagomer-siRNA or a pharmaceutical composition comprising the same, for the treatment of cancer.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Preparation of an Improved Gagomer Composition Encapsulating siRNA a) Preparation of the Lipid Composition:

The following lipids (Table 1) are weighted into glass boiling flask with 95% ethanol and dissolved in 65° C. water bath with stirring:

TABLE 1

| | |
|---|---|
| MW first Lipid (DOTAP) | 698.54 |
| % of the first lipid | 60% |
| MW second Lipid (Cholesterol) | 386.54 |
| % of the second lipid | 30% |
| MW third Lipid (DLPE) | 579.8 |
| % of the third lipid | 10% |
| Mole of each lipid | 1.686E−06 |
| Weight for preparation (mg) first lipid | 70.67 |
| Weight for preparation (mg) second lipid | 19.55 |
| Weight for preparation (mg) third lipid | 9.77 |
| Final weight of lipids (mg) | 100 |

Flask with clean suspension is placed in Buchi 210 evaporator and lipid film is formed (full vacuum, 60° C.). To confirm ethanol evaporation the flask was placed under $N_2$ flow for 20-30 seconds. Lipid film is dispersed in 10 ml 100 mM pH 9.0 Borate Buffer, by flask rotation in 60° C. water bath for 15-30 seconds. Then, flask is vortexed for 2 minutes with full turn rotation and incubated for 2 hours in 37° C. on an orbital shaker. Desired lipid particle size (80-200 nm) are obtained by sequential lipid dispersion filtration through various filters (200 nm (×5), 100 (×5), 200 (×1)) in heated (60° C.) lipid extruded (thermobarrel lipid extruded, Northern Lipids).

b) Activation of Hyaluronic Acid

The Hyaluronic Acid is dissolved to a final concentration of 2 mg/ml in buffer acetate (100 mM sodium acetate (MP Biomedicals, Cat#127-09-3), 111 mM NaCl, pH 4.0) for 1 hour at 37° C. with stirring until clear solution is obtained.

The 1-ethyl-3-(3-dimethylaminopropyl)carbodiimide (EDC cross linker) is added at 20×HA (w/w) and incubated for 1 hour at 37° C. with stirring/shaking.

c) Gagomer Composition Formation

2 µl (2.66 pg) of siRNA (stock 100 µM in siRNA buffer, Darmacon) is added into 2.68 µl of OptiMEM (Invitrogen), and incubated with 2.66 µl (26.6 pg) of lipid carrier (10 mg/ml) for 15 minutes at room temperature. 2.66 µl of HA-EDC (5.32 µg HA) is added and incubated over night at 37° C. with no agitation.

Example 2—Size Distribution of the Particulate Lipid Composition of the Gagomer

Figure 2A:
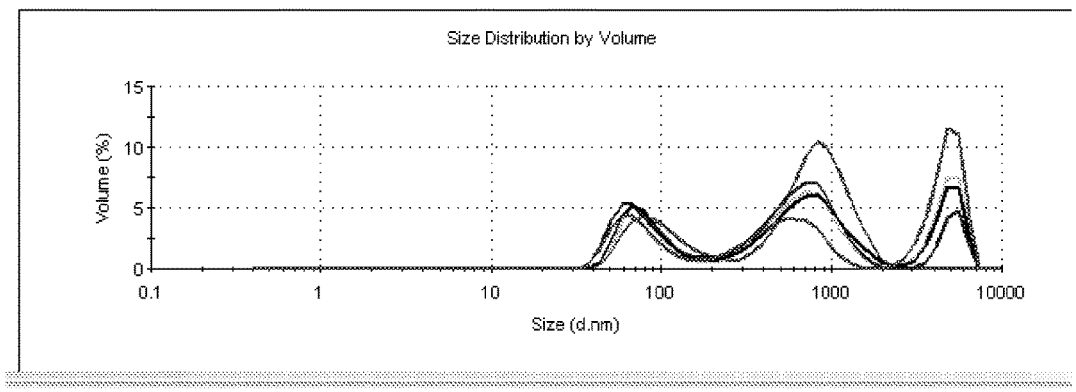
FIGS. 2A-C—Zeta sizer analysis data showing particle size distribution of the particulate lipid composition.
Figure 2B:
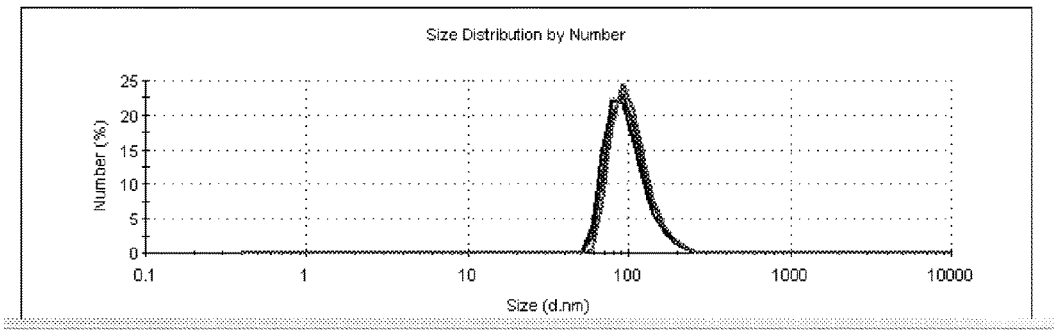
Figure 2C:
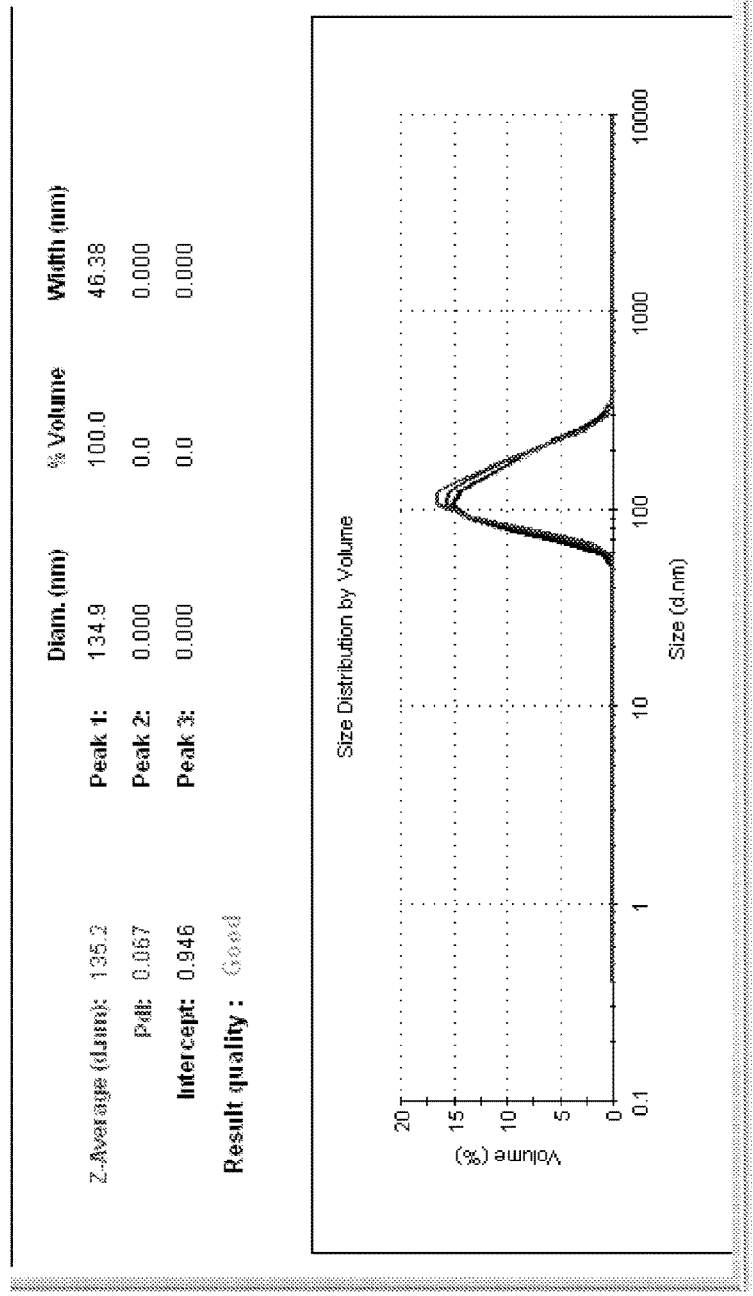

Results shown in FIGS. 2A-C are from analysis using ZetaSizer showing particle size distribution of the lipid composition.

The results shown in FIG. 2A are of particulate lipid composition prepared after extrusion through 400 nm (×4), 200 nm (×4), 100 nm (×4) and 50 nm (×4) nm filters. The results show that the Particle size is not uniform. Main peak (62.7%) is of over 400 nm particle size and only about 30% is of desired 100-150 nm size.

The results shown in FIGS. 2B and 2C are of particulate lipid composition prepared by methods of the present invention (prepared as detailed in Example 1), after extrusion of the lipid composition through 200 nm (×7), and 200 nm (×5), filters. The results demonstrate that a single, unique peak is obtained, at 100% distribution, which is very reproducible at an average size of about 135 nm.

Hence, the results show that the lipid composition of the present invention, prepared in accordance with the methods of the present invention provide uniformly sized particles at a desired nanometric size.

Figure 3:
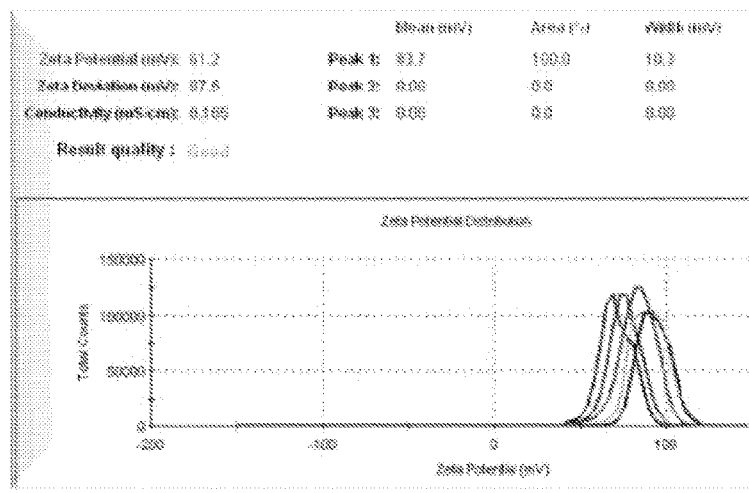
FIG. 3—Graphs showing the changes in Zeta potential of: (A) cationic particulate lipid composition; (B) after addition of siRNA; (C) after addition of activated HA to the cationic lipid composition.
Figure 3:
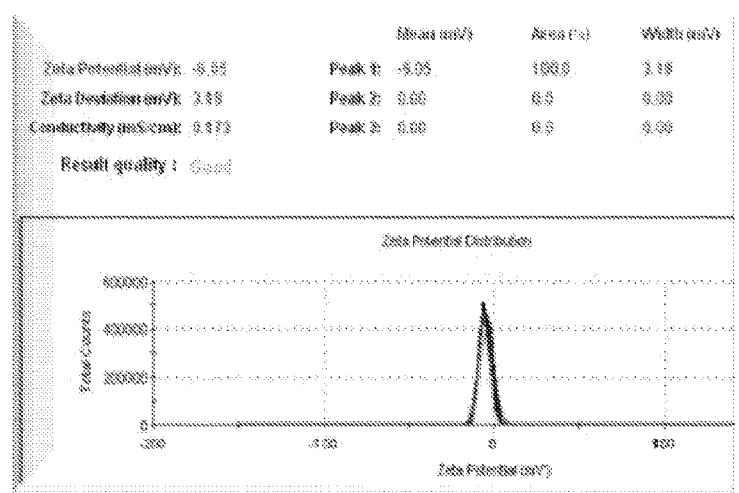
Figure 3:
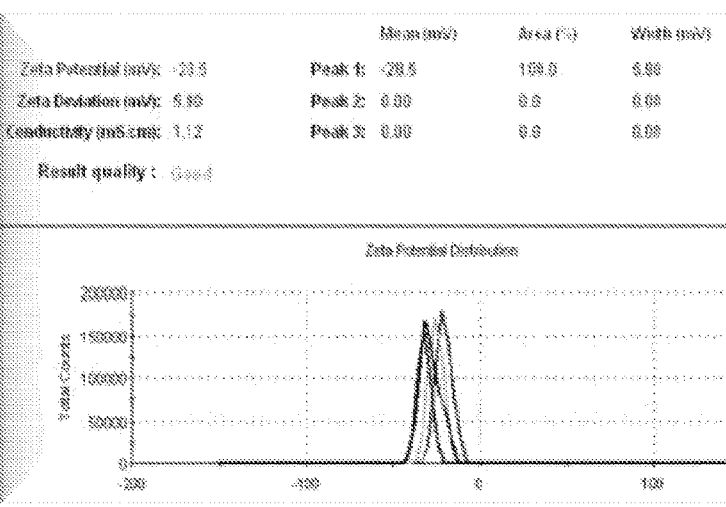

Example 3—Changes in Properties of the Lipid Composition Upon Formation of the siRNA-Gagomer Structure The results shown in FIG. 3, panels A-C, demonstrate the changes of Zeta potential (mV): Panel (A): lipid composition alone (without addition of siRNA or activated HA)—a positive charge of about +61.2 mV. Panel (B): upon addition of siRNA, the charge decreases to −6.05 mV. Panel (C): upon addition of activated HA to the lipid composition-siRNA and formation of the Gagomer composition, the charge changes to a negative charge of an average of about −28.5 mV. Thus, the results demonstrate that the cationic lipid net charge is made negative by addition of activated HA and siRNA. This is particularly important for in-vivo delivery, whereby the particle is not perceived by the body to be positively charged thereby conferring a "stealth" modality to the particles. The finding that the siRNA-Gagomer particle does not have any exposed cationic lipids provides additional benefits to the particle as it prevents unwanted interactions with serum proteins which can form aggregates; it does not induce immune response and the outer HA prevents the particle from being identified as foreign.

Figure 4A:
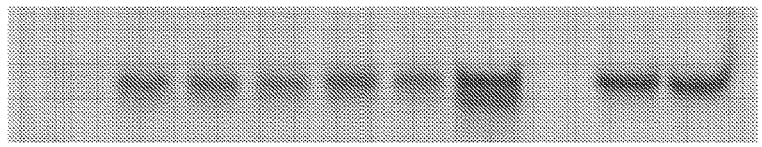
FIGS. 4A-B show an experiment using non-chemically modified siRNA.
Figure 4B:
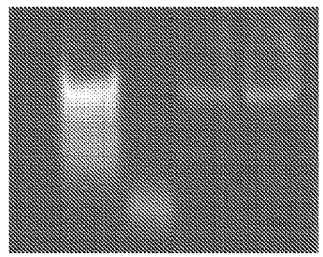

Example 4—the Improved Gagomer Structure Protects the siRNA Encapsulated Therein A non modified siRNA encapsulated within an improved Gagomer, is shown to be stable in human serum for at least 3 hours incubation at 37° C. The results, shown in FIG. 4A demonstrate that the encapsulated siRNA is stable and non-degraded, whereas control, non-encapsulated siRNA is completely degraded after 1 hour incubation. Likewise, in FIG. 4B a control siRNA show degradation products at 60 minutes incubation, whereas the siRNA encapsulated within the Gagomer is protected even after 180 minutes.

Figure 4C:
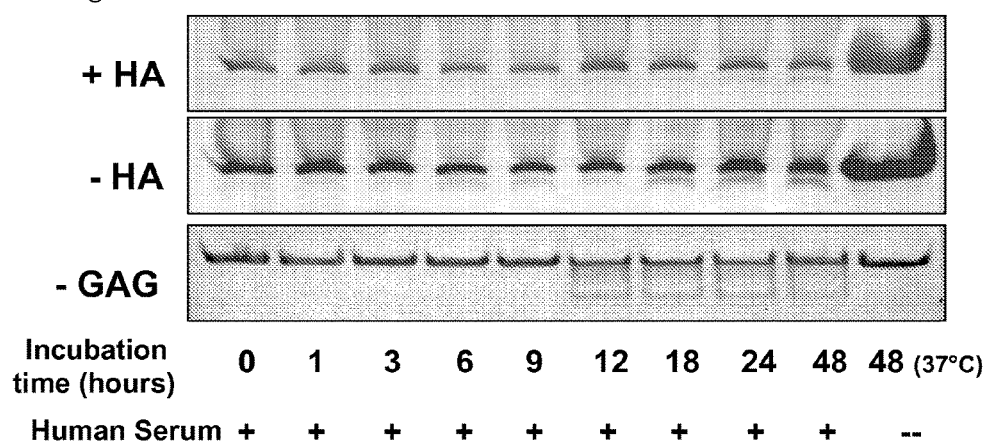
FIG. 4C show an experiment using chemically modified siRNA (using alternating 2-O-methylations)

The results shown in FIG. 4C further demonstrate that siRNA (chemically modified siRNA using alternating 2-O-methylations), encapsulated within a Gagomer is protected in human serum even after 48 hours of incubation. The results further demonstrate that a complete Gagomer particle structure (that is, a Gagomer structure comprising lipid composition and HA) provides the best protection, whereas a particle which comprises only the lipid composition but not HA is not as effective in protecting the siRNA.

Figure 5:
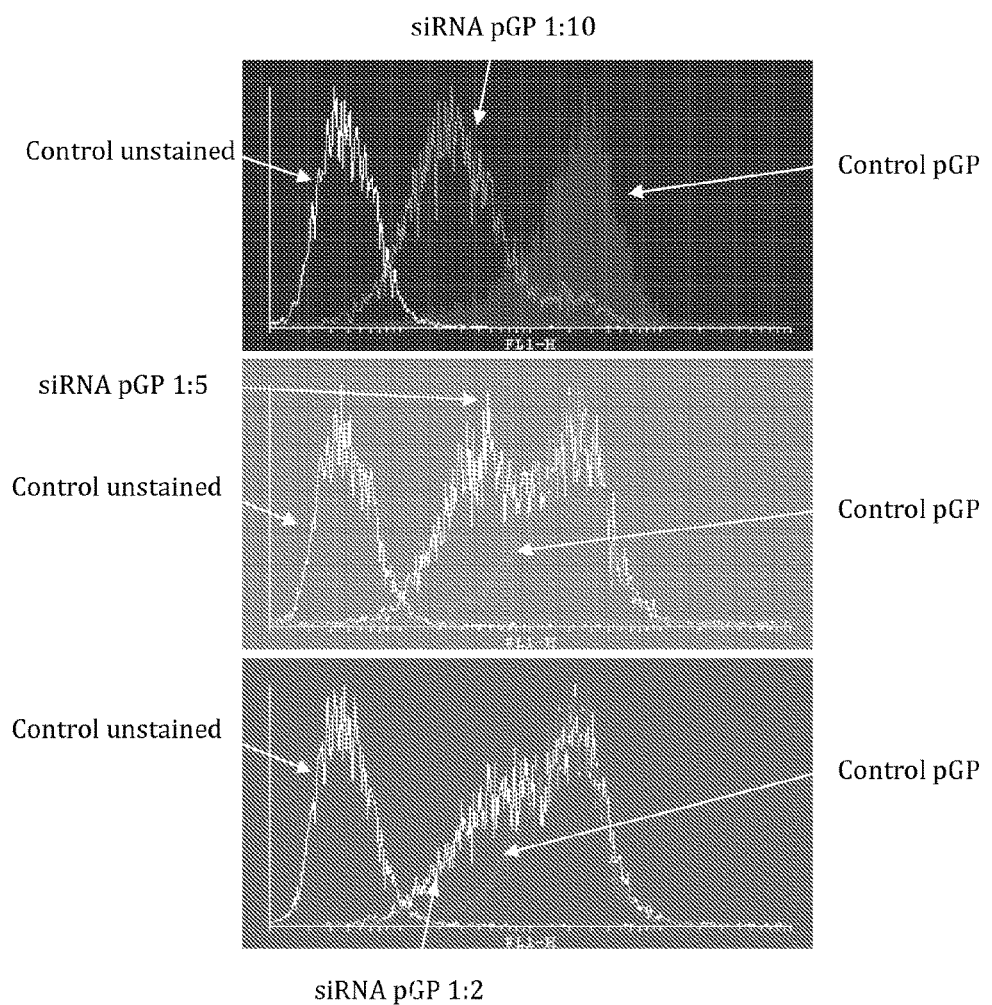
FIG. 5—FACS analysis of the reduction of pGP protein expression after incubation with Gagomer composition comprising siRNA directed against pGP at varying siRNA to lipid ratio. Top Panel—1:10 siRNA to lipid weight ratio, Middle Panel—1:5 siRNA to lipid weight ratio, Bottom Panel—1:2 siRNA to lipid weight ratio.

Example 5—Determining the Weight Ratio of siRNA to Lipids in the Improved Gagomer Composition NCI/ADR-RES cells were introduced with various Gagomer-siRNA compositions and the expression levels of the pGP (MDR1) protein were determined. The results shown in FIG. 5 show a FACS analysis of the cells under various experimental conditions.

Several Gagomer compositions were tested, each having a different lipid to siRNA weight ratio. The surprising results show that at higher lipid to siRNA ratio, an improved effect of the siRNA on the target site is observed. As shown in FIG. 5, the highest reduction of expression of the pGP protein can be seen with a Gagomer composition having an siRNA to Lipid ratio of 1:10 (top Panel), whereas the lowest reduction of expression of the pGP is observed with a Gagomer composition having an siRNA to Lipid ratio of 1:2 (lower Panel).

Figure 6A:
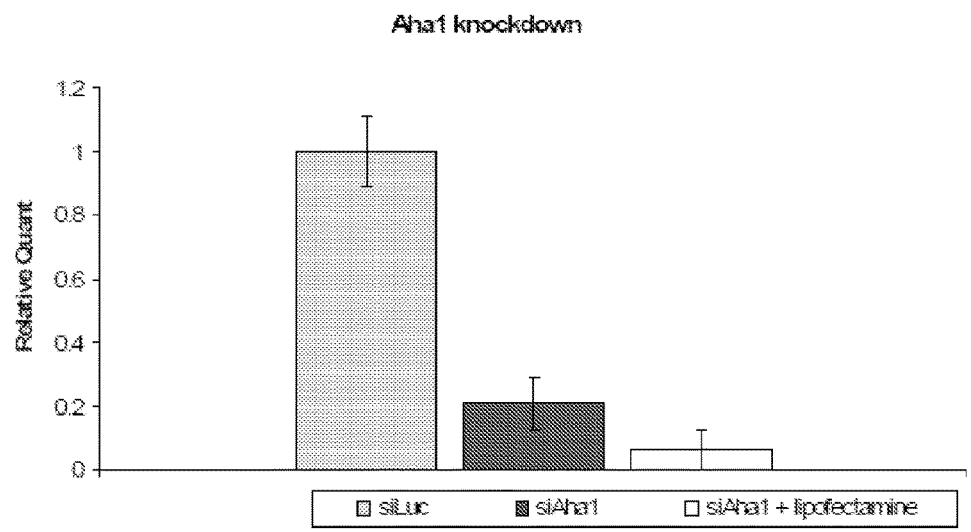
FIGS. 6A-B—Graphs showing the relative reduction of expression of Aha1 and Kif11 (FIGS. 6A and 7B, respectively) in NCI/ADR-RES (NAR) cell line transfected with 100 nm of siRNA encapsulated in an improved Gagomer composition.
Figure 6B:
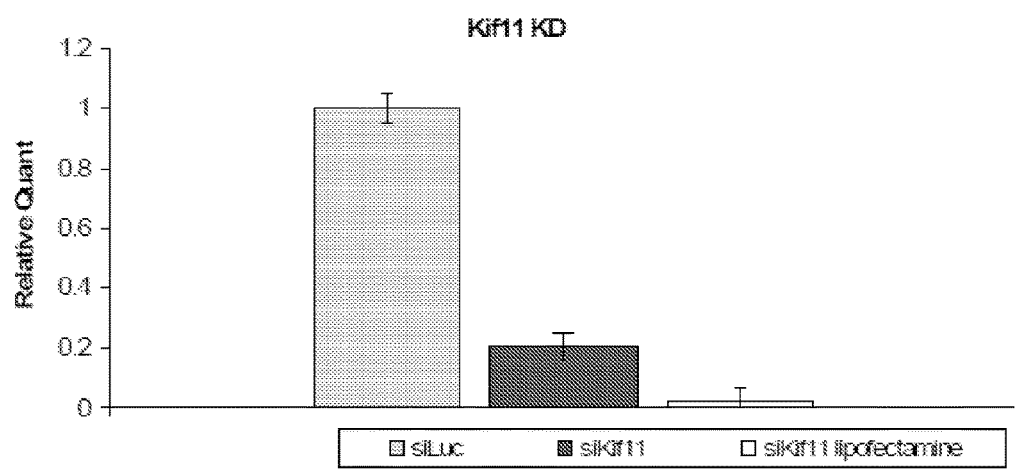

Example 6—Reduction in Expression of Various Genes Mediated by the Improved Gagomer-siRNA Composition NCI/ADR-RES cell line (NAR) were transfected with Gagomer-siRNA compositions, wherein the siRNA molecules are directed against Aha1 or Kif11. 24 hours after transfection with 100 no of the relevant siRNA, cells were harvested and expression levels of Aha1 and Kif11 mRNA were determined by using real time RT-PCR methods. The samples were normalized to PIP (Cyclophilin B) gene expression level. The results which are presented in FIGS. 6A-B are from two independent experiments. The results demonstrate the relative reduction in expression of Aha1 (FIG. 6A) and Kif11 (FIG. 6B) exerted by the Gagomer-siRNA (siAha1 and siKif11, respectively). Negative control is transfection of the cells with a Gagomer encapsulating siRNA directed against the Luciferase gene (siLuc), which is able to target the Luciferase gene, which is only endogenously expressed in firefly cells. As a positive control, in order to show that the tested siRNA is active, a commercially available siRNA transfection agent (Lipofectamine, obtained from Invitrogen) was used to transfect siRNA against Aha1 and Kif11 (Luc+siAha1 and Luc+siKif11, respectively).

Figure 7A:
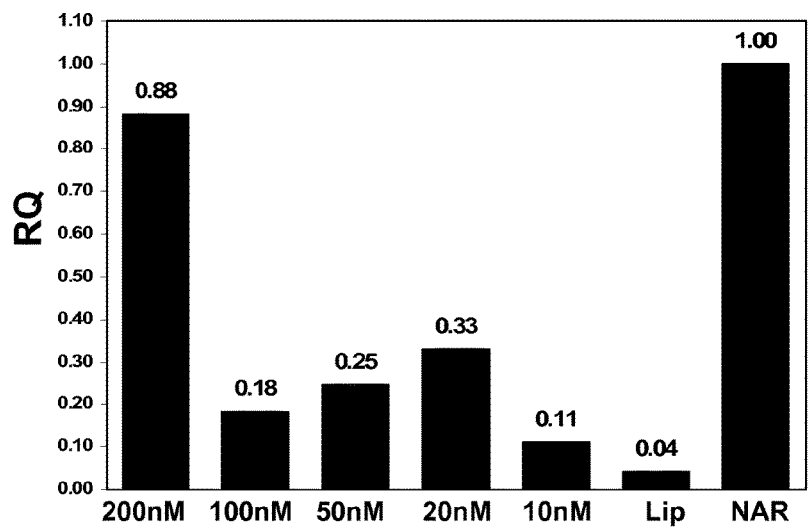
FIGS. 7A-C—Graphs showing a dose response between the amount of siRNA transfected into NAR cells (FIG. 8A-B) or B16F10 cells (FIG. 7C) and the reduction in specific gene expression in the cells after 18 hours of incubation with the improved Gagomer-siRNA composition.
Figure 7B:
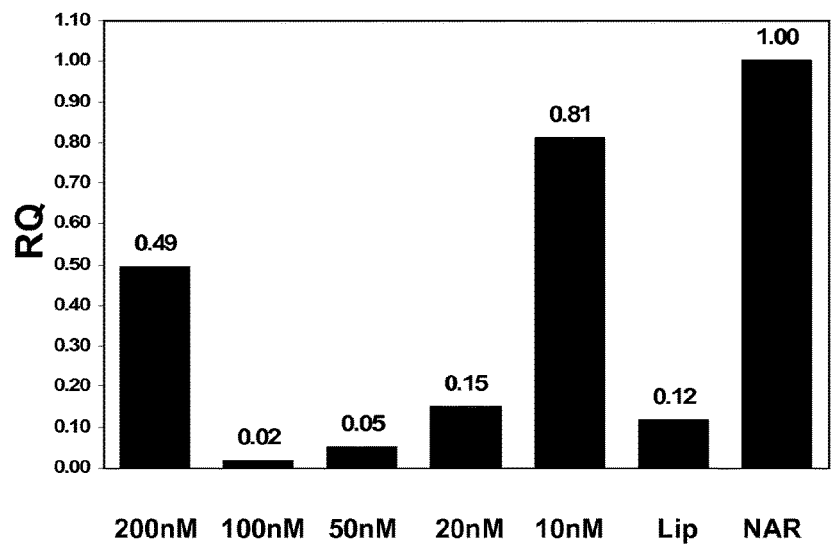
Figure 8A:
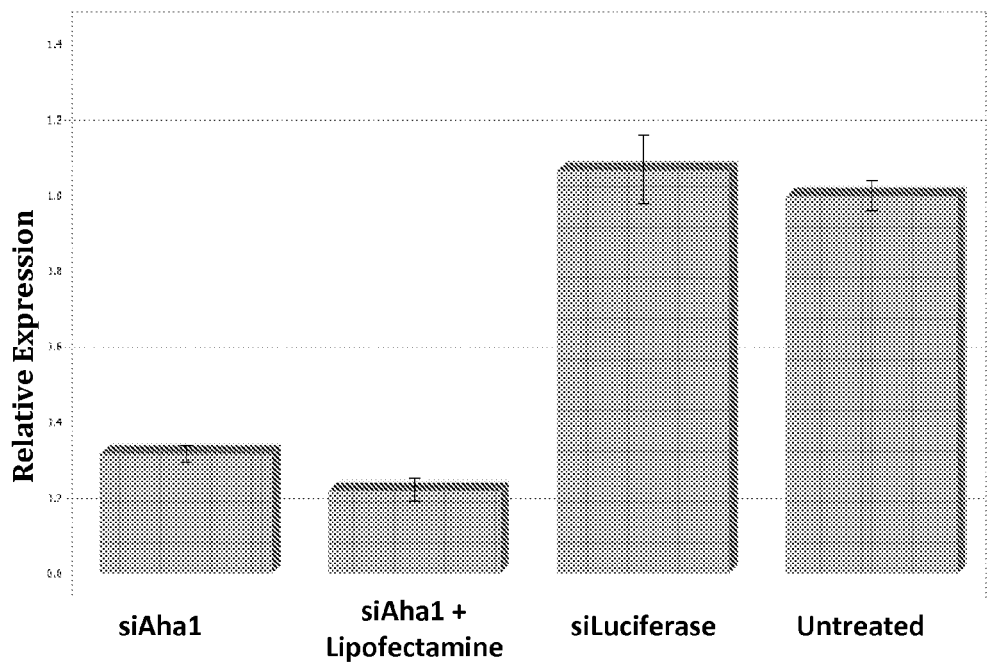
FIGS. 8A-B Graphs showing the relative reduction of expression of Aha1 in various cell lines transfected with 100 nm of siRNA encapsulated in an improved Gagomer composition or by lipofectamine.
Figure 8B:
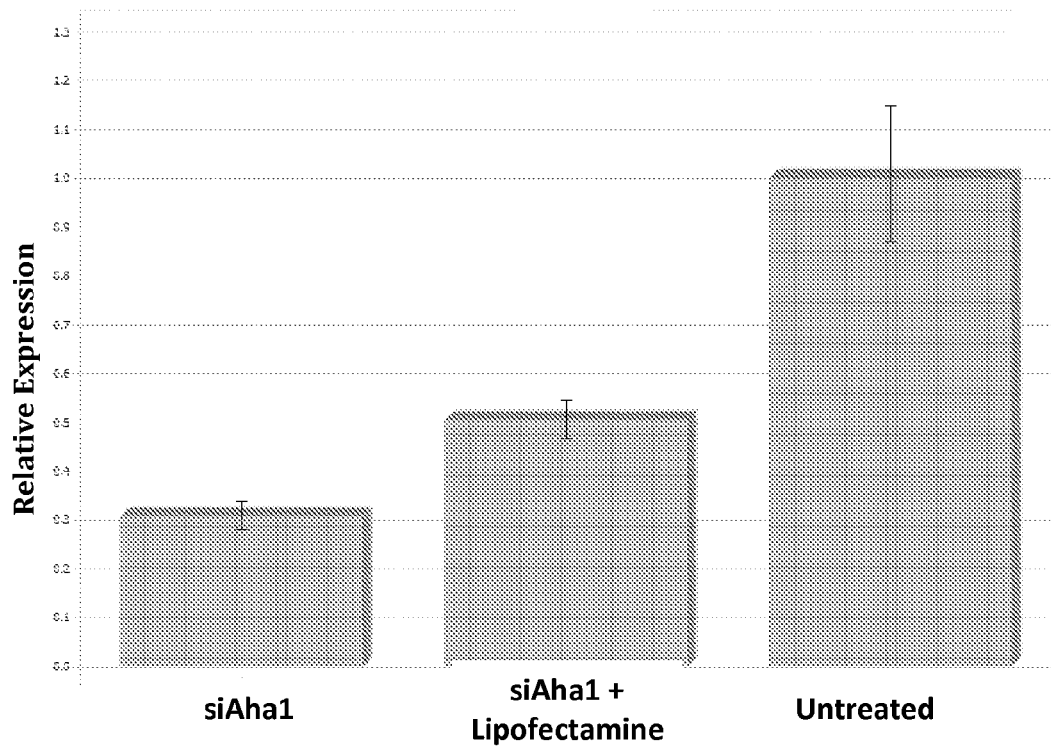

Example 7—Reduction in Expression of Various Genes, which is Mediated by the Improved Gagomer-siRNA Composition—Dose Response Effect of the siRNA Experiments were performed essentially as described in Example 6. Relevant Gagomer-siRNA compositions encapsulating varying amount of the relevant siRNA composition were transfected to the cells and the effect on the reduction of expression of Aha1 (FIG. 8A) and Kif11 (FIG. 8B) were determined. The results, presented in FIGS. 8A-B, show that there is no direct correlation between the amount of siRNA transfected into the cells and the biological effect exerted by the siRNA. As shown in FIG. 7A, transfection of 10 nM of Aha1 siRNA caused the highest reduction in expression of Aha 1, whereas increasing amounts of the same siRNA had a diminished effect on the reduction of expression of Aha1. Interestingly, the highest amount of siRNA (200 nM) exhibited the lowest siRNA effect on expression of Aha1. As shown in FIG. 7B, transfection of 100 nM of Kif 11 siRNA caused the highest reduction in expression of Kif 11, whereas increasing the amount of the same siRNA to 200 nM resulted in a markedly diminished effect of the siRNA on the expression of Kif 1.

Figure 7C:
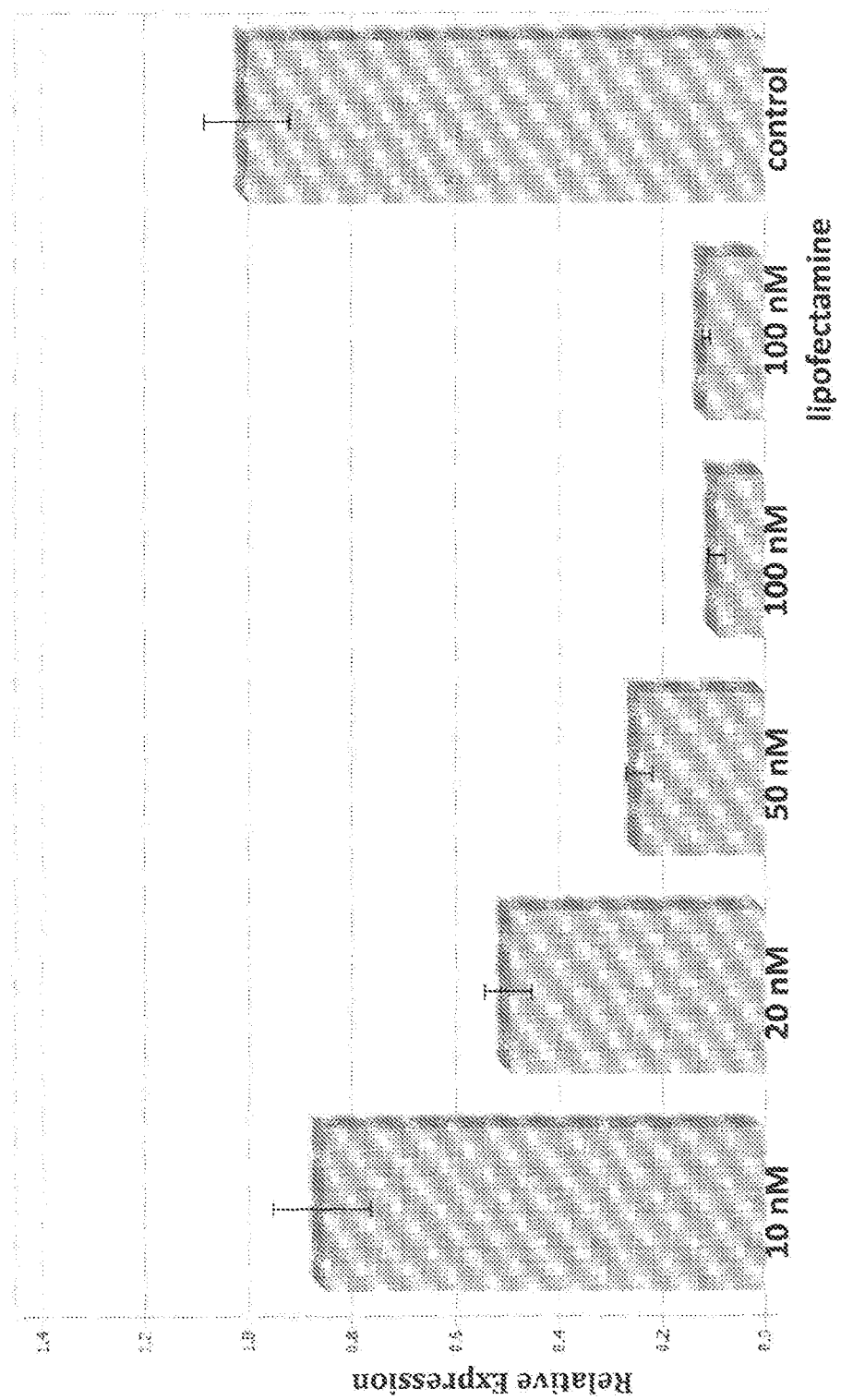

Further shown in FIG. 7C, are dose response effects of Gene A siRNA delivered by the Gagomer composition in B16F10 cells. The results show an effective concentration range of upto 100 nM siRNA.

Example 8—Reduction in Expression of Aha1, Mediated by an Improved Gagomer-Aha1-siRNA Composition in Various Cell Lines Experiments were performed essentially as described in Example 6. B16F10 mouse melanoma cell line were transfected with the following: Gagomer-Aha1 siRNA (siAhasa1), Lipofectamine+Aha1 siRNA (siAhsa1+lipofectamine) and Gagomer-Luc siRNA (siLuciferase). The relative expression of the Aha1 was determined. The results are presented in the bar graphs in FIG. 8A. LLC-D122 human cell line were transfected with the following: Gagomer-Aha1 siRNA (siAhasa1) and Lipofectamine+Aha1 siRNA (siAhsa1+lipofectamine). The relative expression of the Aha1 was determined. The results are presented in the bar graphs in FIG. 8B. The results presented in FIGS. 8A-B demonstrate that the Gagomer-siRNA composition effectively reduces the expression of the relevant mRNA in mouse and human cell lines.

Example 9—Lack of an Immuno-Toxic Effect of the Improved Gagomer-siRNA Composition on Cells PBMC cells were tested to detect an immuno toxic effect of the improved Gagomer-siRNA composition on the cells. As a positive control for an immunotoxic effect, LPS at a concentration of 1 mg/ml was used. PBMC cells were incubated with varying concentrations of Aha1 siRNA-Gagomer compositions and an immune response (as tested by cytokine or interferon response) was measured. The Assay (ELISA based commercial kit 9-PLEX human cytokine kit, Quansys) was repeated using PBMCs isolated from 3 different donors. Blood was obtained for PBMC Ficoll-based isolation from Magen David Adom Blood Bank. The varying concentrations of siRNA-Gagomer used were 10, 100, 500 nM, representative of effective dose (ED) (in-vitro knockdown), ED×10 and ED×50.

Figure 9A:
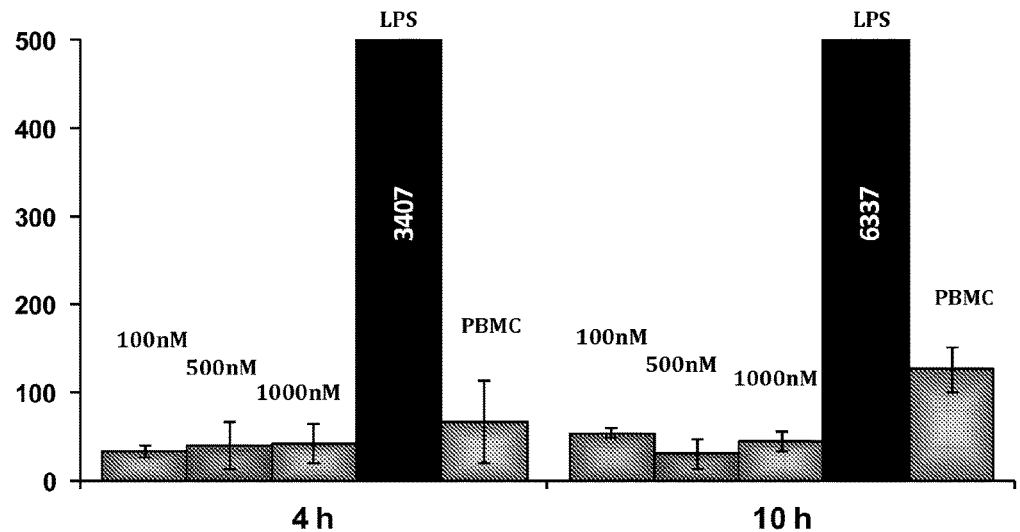
FIGS. 9A-D—Bar graphs showing the changes in expression levels (concentration, pg/mL) over time (hours) of cytokines or interferons after transfection of PBMC cells with the improved Gagomers-siRNA composition. The results show that the improved Gagomers-siRNA composition does not induce any significant immune response.
Figure 9B:
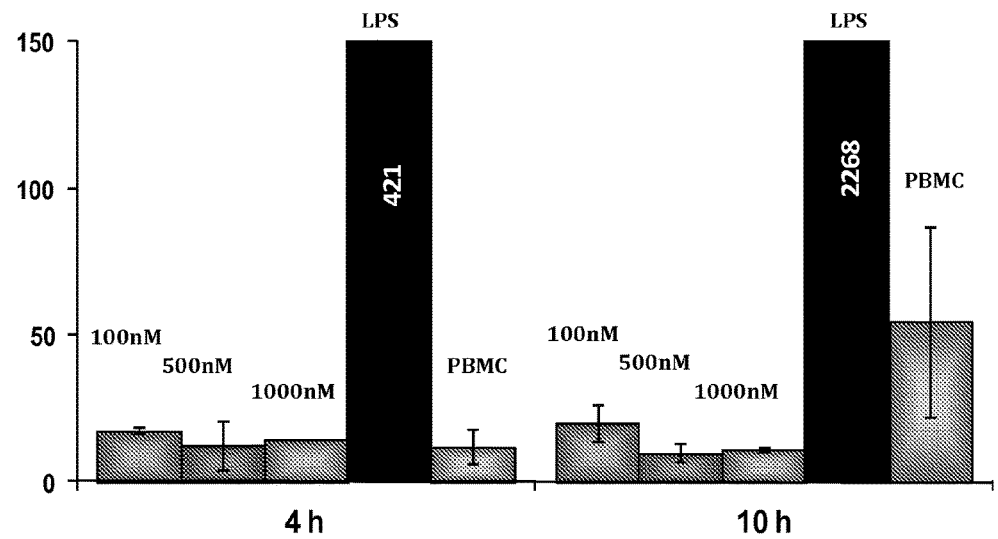
Figure 9C:
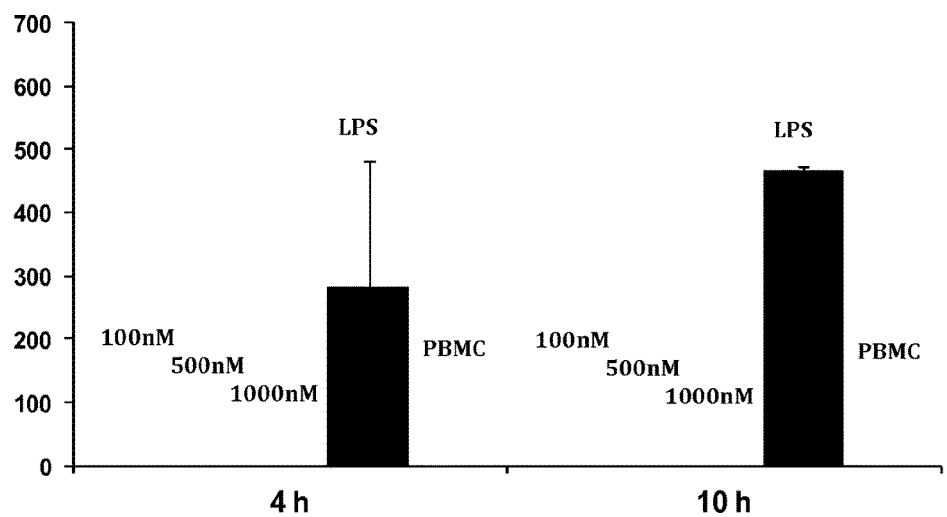
Figure 9D:
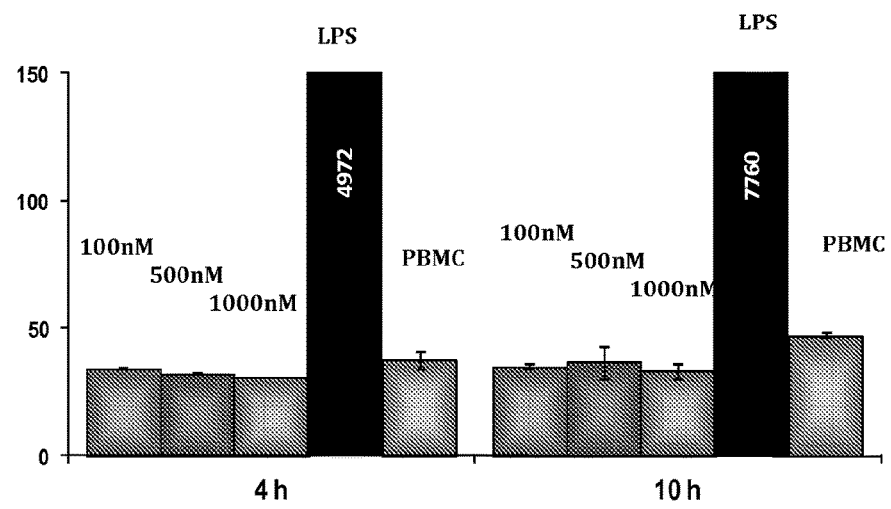

The results, shown as Bar graphs in FIGS. 9A-D demonstrate that in all cases, incubation of PBMCs with siRNA-GAGs did not induce any significant immune response (no cytokine or interferon response was observed). The results show same trend with each donor having a different baseline levels of tested cytokines stemming from inherent variability of human donors. FIG. 9A shows changes in IL 6 expression; FIG. 9B shows changes in IL 10 expression; FIG. 9C shows changes in INFγ expression; and FIG. 9D shows changes in TNFα expression. For each time point, the bar graphs of each of FIGS. 9A-D represent the following treatments (from left to right): 100 nM siRNA-Gagomer, 500 nM siRNA-Gagomer; 1000 nM siRNA-Gagomer; 1 mg/ml LPS; Control, untreated cells (PBMC).

Example 10—Comparison Between Gagomer Particles Comprising DOTAP as Cationic Lipid and Gagomer Particles Comprising DOTMA as Cationic Lipid Cytokine induction in human peripheral mononuclear cells (PBMCs) by either Gagomer particle composition comprising DOTAP as cationic lipid ("DOTAP particles") or with Gagomer particle composition comprising DOTMA as cationic lipid ("DOTMA particles") was tested. Each composition consists of the same amount of lipids (total: 1 uM) and the same amount of siRNAs (100 nM) in a constant ratio of 1:10 siRNA:lipids. The HA coating shell was quantified to be at 60 μg HA/μmole lipid.

PBMCs were isolated from 6 healthy volunteers and the cells (200,000 cells/well in a 24 well plate) were incubated in triplicates. DOTAP particles (100 nM siRNAs, 1 g lipids), DOTMA particles (100 nM siRNAs and 1 g lipids), were added to the cells. Negative control are non-treated PBMCs in culturing media. LPS (1 μg/mL) served as a positive control. At 2 hours and 6 hours post incubation, the cells were subjected to ELISA of IL-6 (global marker of inflammation), TNF-α and IFN-γ. The results are presented in FIGS. 10A-C, respectively.

Figure 10A:
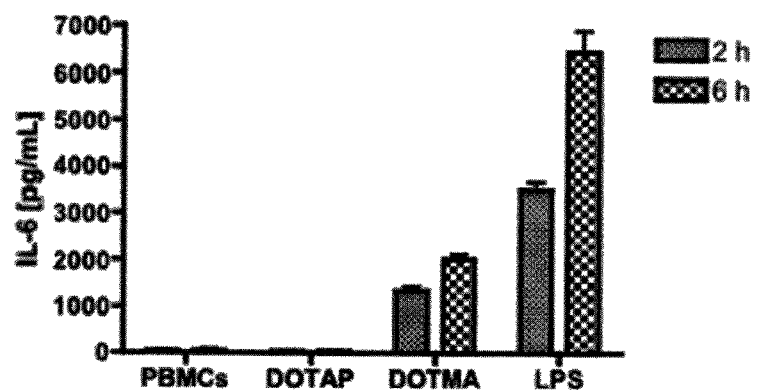
FIGS. 10A-C—Bar graphs showing the changes in expression level (concentration, pg/mL) over time (hours) of cytokines or interferons after transfection of PBMC cells with Gagomer particles comprising as a cationic lipid DOTAP ("DOTAP") or Gagomer particles comprising as a cationic lipid DOTMA ("DOTMA"). The results show that, surprisingly, whereas the Gagomers comprising DOTAP do not induce any significant immune response, the Gagomers comprising DOTMA, induce a robust and acute increase in concentration of various inflammation markers (IL-6, TNF-α and IFN-γ).

As shown in FIG. 10A, a robust IL-6 induction as early as 2 h post incubation with the DOTMA particles can be identified. Further increase in IL-6 concentration was observed 4 h later. In contrast, incubation with the DOTAP particles did not induce any such induction in IL-6 expression (concentration).

Figure 10B:
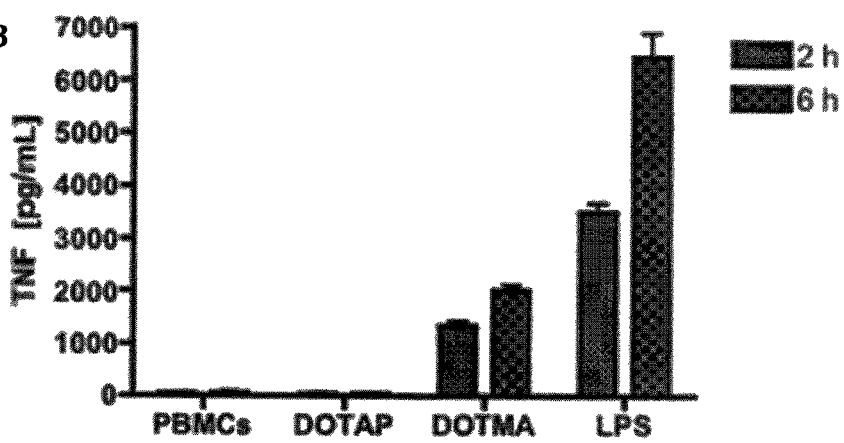
Figure 10C:
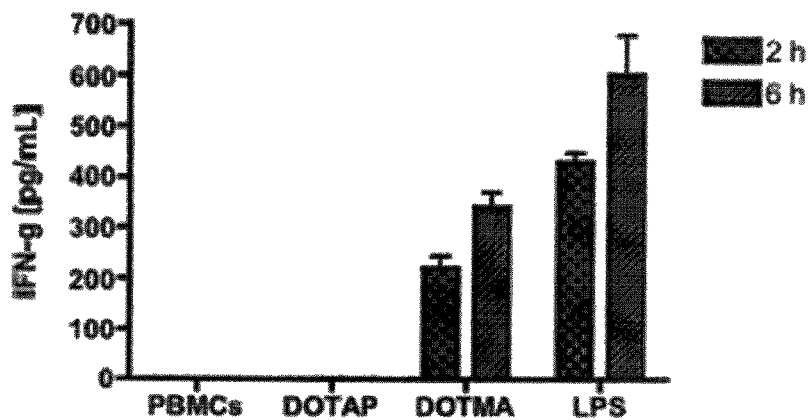

Similarly, as shown in FIG. 10B, treating the cells with DOTMA particles induced high levels of TNF-α even after 2 hours of incubation, whereas treatment with DOTPA particles did no induce such response. As further shown in FIG. 10C, treating the cells with DOTMA particles induced high levels of IFN-γ even after 2 hours, whereas treatment with the DOTAP particles did not induce such response.

Altogether, the results demonstrate that, surprisingly, when DOTMA is used as a cationic lipid in the Gagomer particle composition, it induces an immune toxicity, whereas the cationic lipid DOTAP does not induce such response.

Example 11—In-Vivo, Time Dependent Bio-Distribution of Improved Gagomer Composition Carrying siRNA To test the time dependent biodistribution study of siRNA-Gagomer in naïve and melanoma bearing mice, Cy5-fluorescently labeled siRNA was used. Cy5 labeled siRNA encapsulated within the improved Gagomer composition was injected into naïve and tumor-bearing mice and organs (liver, kidney, spleen, lungs and tumors in relevant groups) were harvested at different time points of 1, 6, 24, 48 and 72 hours later. Fluorescence was observed using Confocal microscopy on cryosectioned preparations.

Model induction (subcutaneous B16F10 inoculation): Mice were subcutaneously injected (clipping at approximately 48 hrs prior to injection) with $10^5$ cells/mouse of B16F10 cells into the right flank, 0.2 ml/mouse (using 0.3 ml insulin syringe with 29G needle).

IV injection: The siRNA Gagomer complex (102.5 µl/25 g mouse) was injected IV via the tail vein according to standard procedures. Briefly, mice were placed under heating lamps for 5 minutes, placed in restrainer and using a 1 ml insulin syringe with G30 needle the gagomers were slowly injected into the tail vein.

Fluorescent microscopy assessment of harvested organs: Harvested organs (tumor, liver, lung, spleen and kidneys) were post-fixed in 10% neutral buffered formalin overnight at room temperature, then cryoprotected in 30% sucrose (ICN Biomedicals, Inc., Cat.N 190271) at 4° C. overnight. The organs were then transferred to O.C.T. Compound (Tissue-Tek, Cat.N 4583) for embedding overnight at 4° C. protected from light. 5 µm-thick frozen tissue sections were cut using Cryostat (Leica CM3050) in fresh OCT, mounted on Superfrost Plus slides (Thermo Scientific, Cat.N J1800AMNZ) with DAPI containing aqueous mounting medium Fluoroshield (Sigma). Sections were evaluated using confocal microscopy (Olympus Fluoview 300 and LSM Zeiss 710) and images were acquired using ZEN2009 software. Tissue fragments were considered positive (i.e., a successful GAG-Cy5 Luc siRNA transfer/intracellular incorporation occurred) only if histological (microscopic) examination showed clear fluorescence signal within specific cells or structures. Background DAPI staining assisted in identification of tissue structure. The Cy5 autofluorescence signal was defined using the control (untreated) tissue and images were normalized using this threshold.

Reference is now made to FIG. 11A, which shows confocal microscopy pictograms of liver sections of naïve or tumor bearing mice, harvested at the indicated time points after administration of the Gagomer encapsulating the Cy5-labeled siRNA. The results shown in FIG. 11A, demonstrate that all observed Cy5-siRNA is found within blood vessels, no fluorescence seen in adjacent cells. Further notable are marked differences in fluorescence levels between naïve and tumor-bearing mice.

Figure 11B:
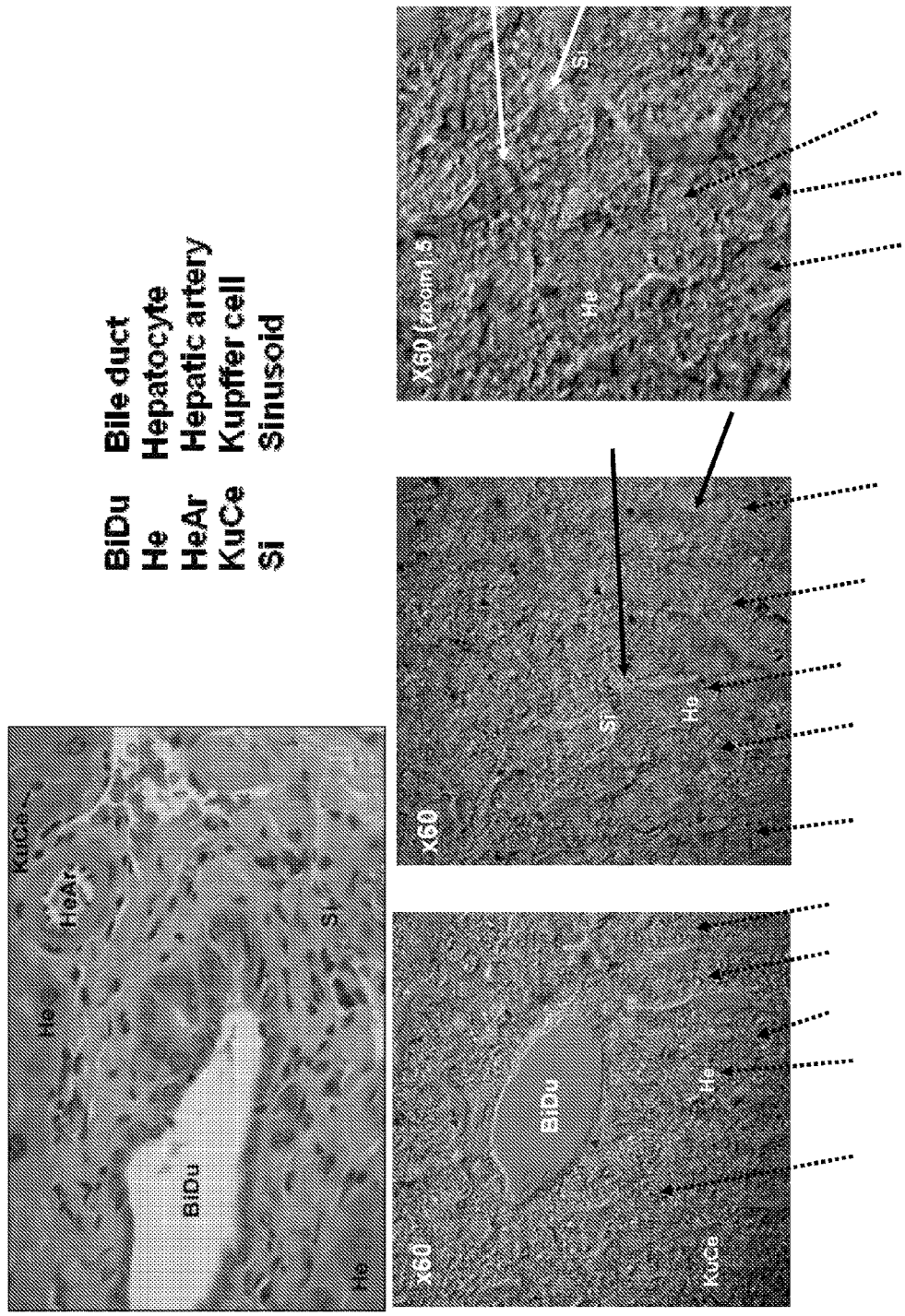

Reference is now made to FIG. 11B, which shows high resolution spectral microscope images of liver sections. The results demonstrate that all observed Cy5-siRNA is found within blood vessels and sinusoids, no fluorescence seen in adjacent cells. Pictures were taken at 6 hours post Cy5-siRNA administration. Top panel represents H&E stained section of liver showing morphologically relevant areas. Lower panel images show cell nuclei (DAPI stained (dashed arrows) and fluorescent siRNA (solid arrows).

Figure 11C:
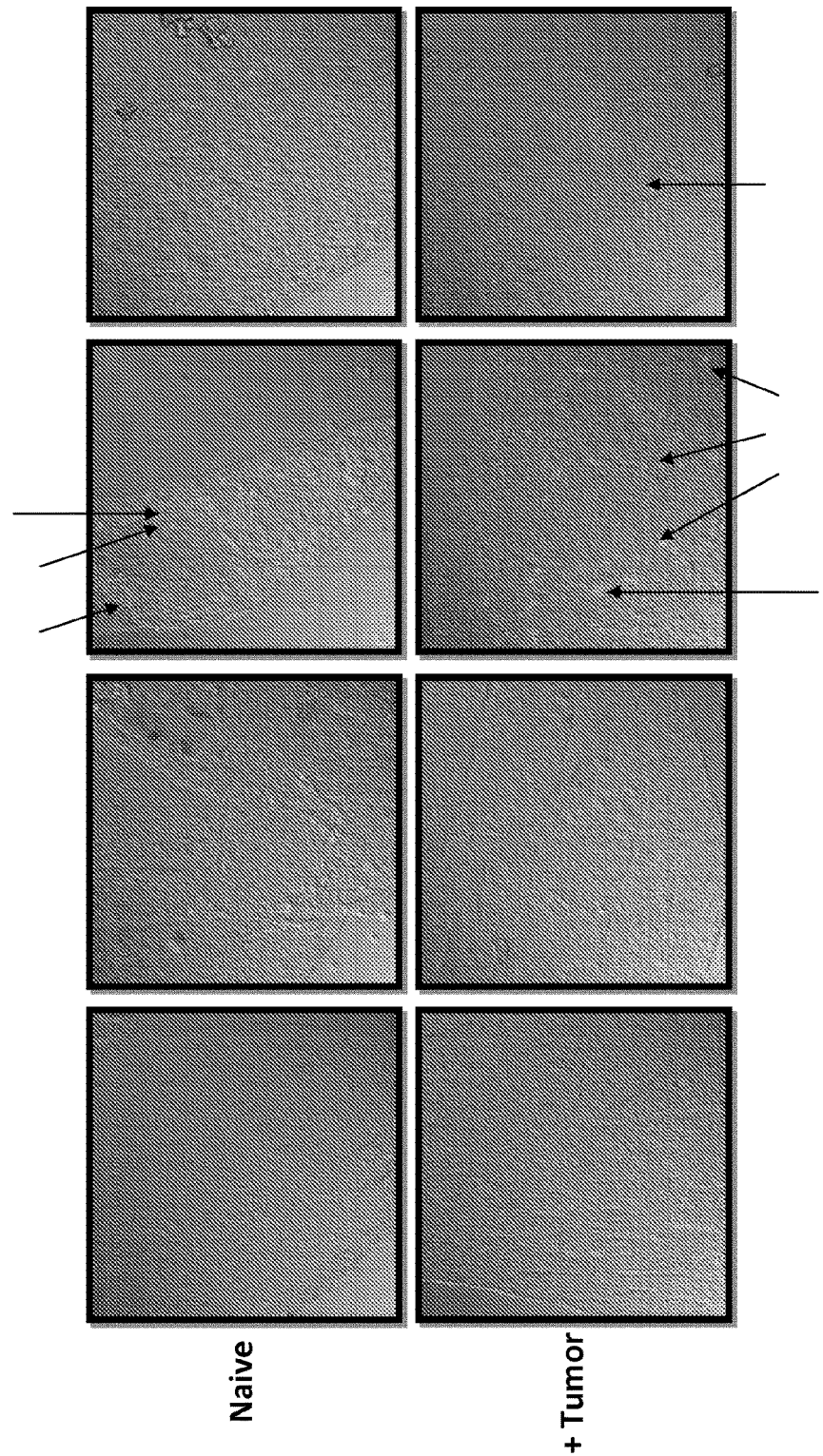

Reference is now made to FIG. 11C, which shows confocal microscopy pictograms of spleen sections of naïve or tumor bearing mice, harvested at the indicated time points after administration of the Gagomer encapsulating the Cy5-labeled siRNA. The results shown in FIG. 11C, demonstrate that all observed Cy5-siRNA is found within blood vessels in red matter, no fluorescence seen in cells or in white matter. Further notable are marked differences in fluorescence levels between naïve and tumor-bearing mice.

Figure 11D:
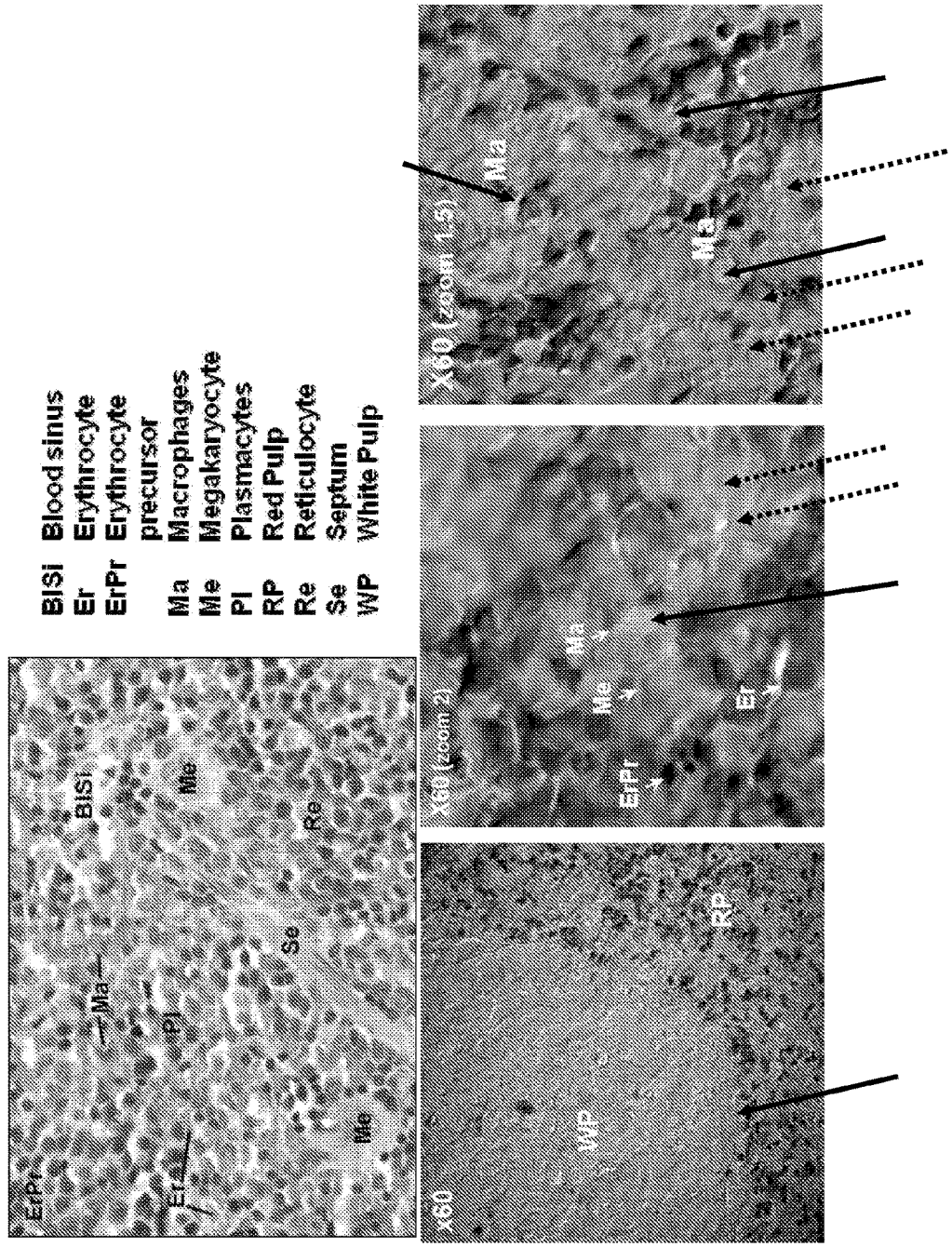

Reference is now made to FIG. 11D, which shows high resolution spectral microscope images of spleen sections. The results demonstrate that all observed Cy5-siRNA is found within red pulp, no fluorescence seen in adjacent cells. Pictures were taken at 6 hours post Cy5-siRNA administration. Top panel represents H&E stained section of spleen showing morphologically relevant areas. Lower panel images show cell nuclei (DAPI stained (dashed arrows) and fluorescent siRNA (solid arrows).

Figure 11E:
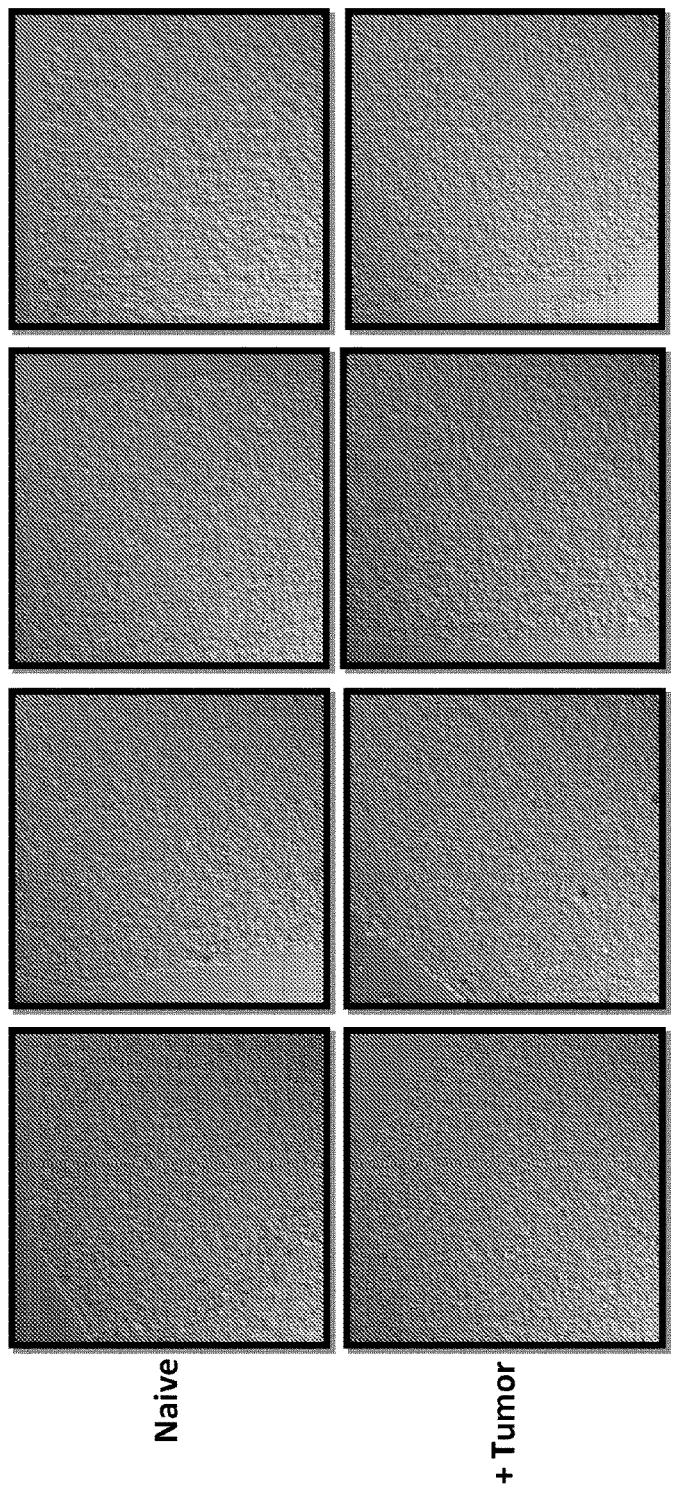

Reference is now made to FIG. 11E, which shows confocal microscopy pictograms of kidney sections of naïve or tumor bearing mice, harvested at the indicated time points after administration of the Gagomer encapsulating the Cy5-labeled siRNA. The results shown in FIG. 11E, demonstrate that no fluorescence is observed.

Figure 11F:
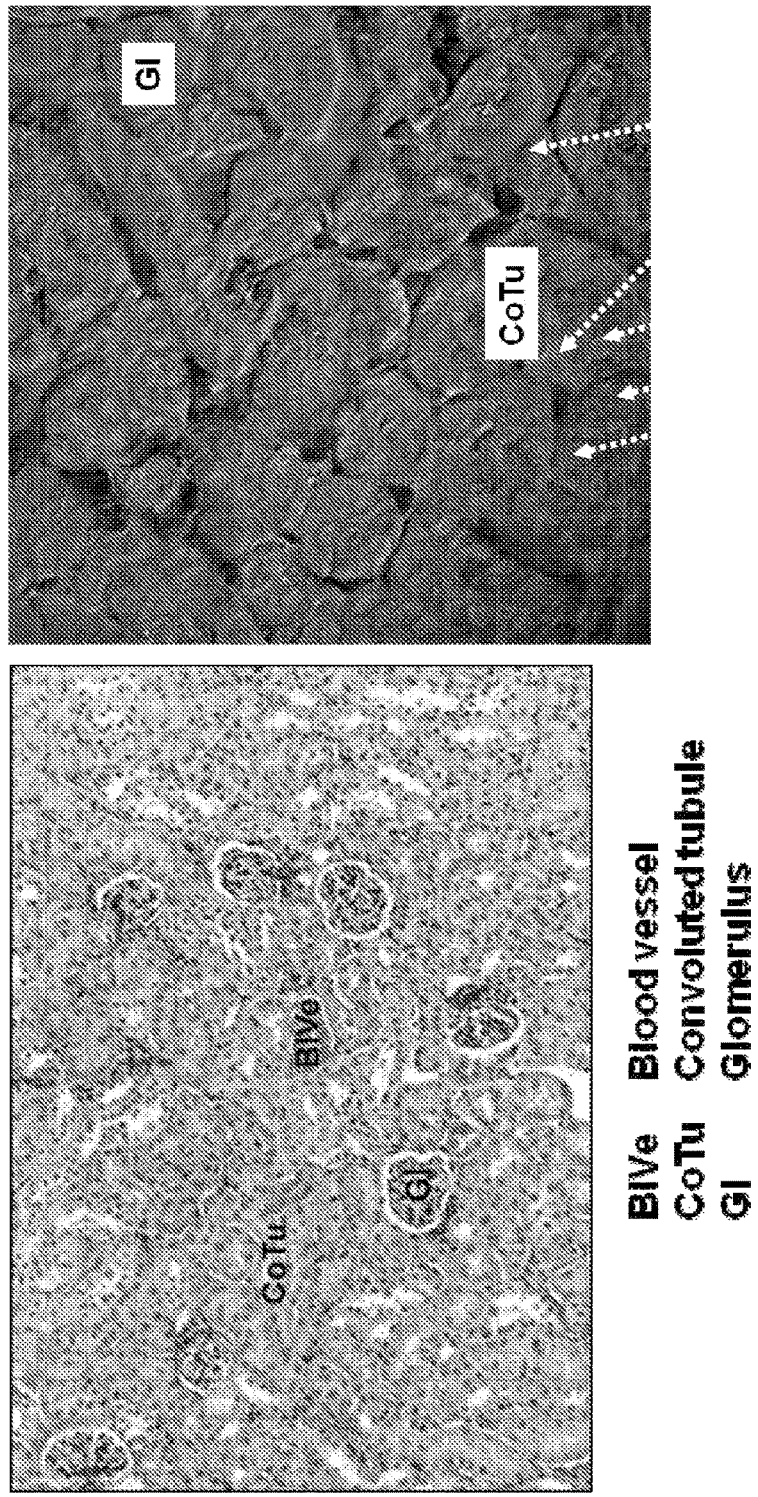

Reference is now made to FIG. 11F, which shows high resolution spectral microscope images of kidney sections. The results demonstrate that no fluorescence is detected. Pictures were taken at 6 hours post Cy5-siRNA administration. Left hand panel represents H&E stained section of kidney showing morphologically relevant areas. Right hand panel images show cell nuclei (DAPI stained (dashed arrows)).

Figure 11G:
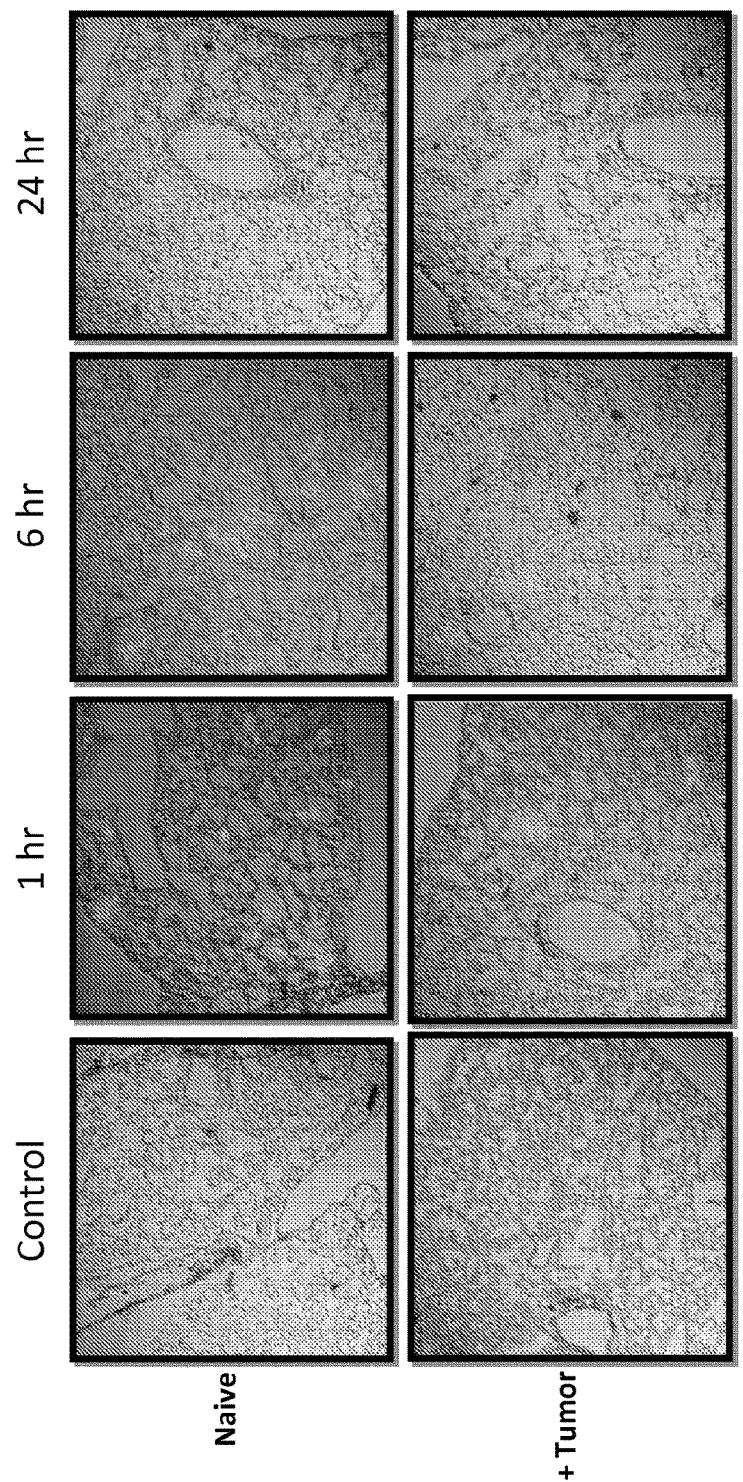

Reference is now made to FIG. 11G, which shows confocal microscopy pictograms of lungs sections of naïve or tumor bearing mice, harvested at the indicated time points after administration of the Gagomer encapsulating the Cy5-labeled siRNA. The results shown in FIG. 11G, demonstrate that all observed Cy5-siRNA is found within blood vessels in red matter, no fluorescence seen in adjacent cells. Further notable are marked differences in fluorescence levels between naïve and tumor-bearing mice.

Figure 11H:
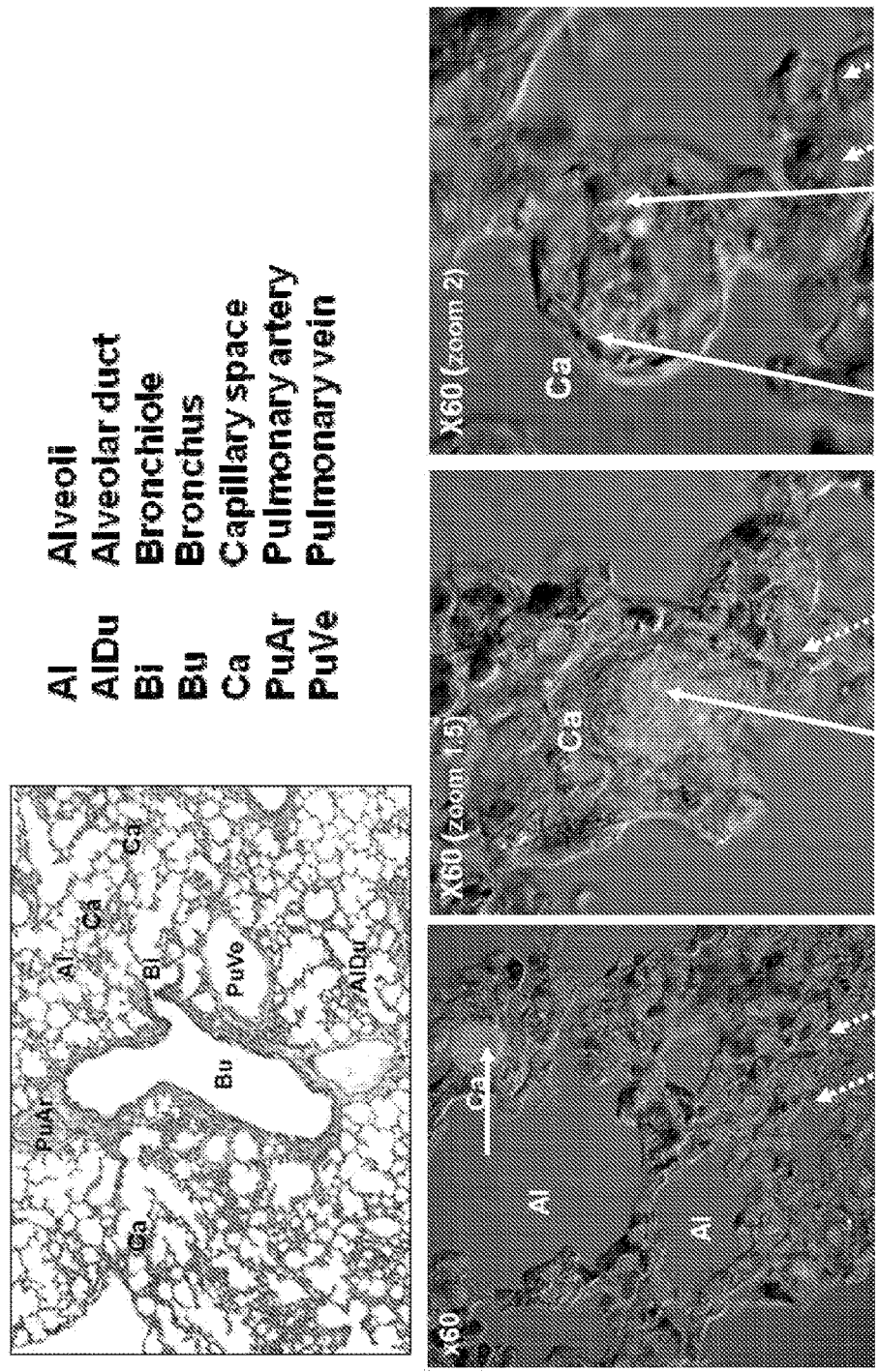

Reference is now made to FIG. 11H, which shows high resolution spectral microscope images of lungs sections. The results demonstrate that all observed Cy5-siRNA is found within blood vessels, no fluorescence seen in adjacent cells. Pictures were taken at 6 hours post Cy5-siRNA administration. Top panel represents H&E stained section of lungs showing morphologically relevant areas. Lower panel images show cell nuclei (DAPI stained (dashed arrows) and fluorescent siRNA (solid arrows).

Figure 12A:
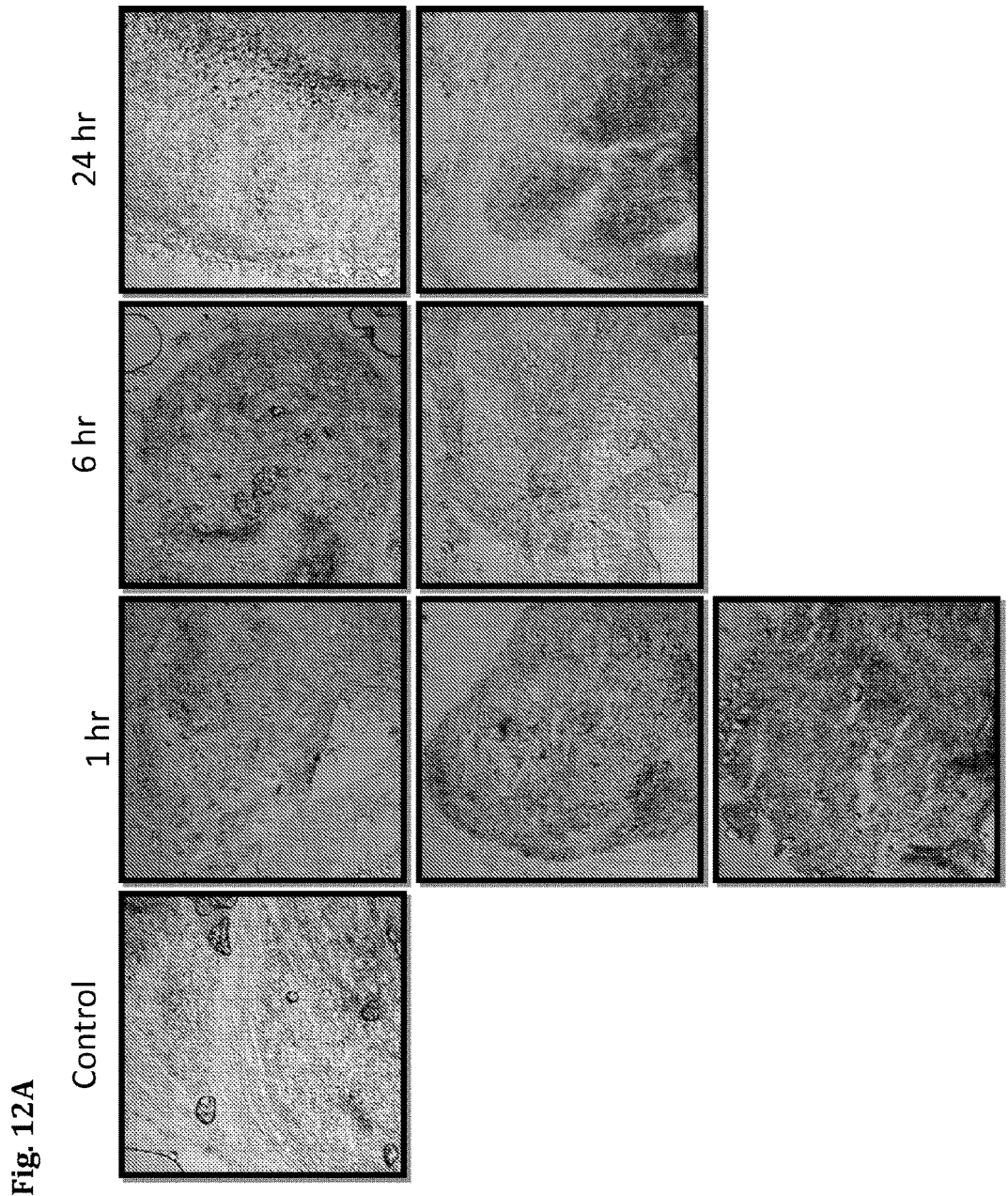
FIGS. 12A-C—images of cryosections of tumors obtained from the tumor bearing mice at different time points.

Reference is now made to FIG. 12A which show confocal microscope images of cryosections of various tumors/tumor regions obtained from the tumor bearing mice at different time points (1 hr, 6 hr, and 24 hr) after injection of Gagomer composition comprising Cy5-labeled siRNA. The results shown in FIG. 12A demonstrate that Cy5-siRNA is found in blood vessels and cells of the tumor, with peak delivery after about 1 hour.

Figure 12B:
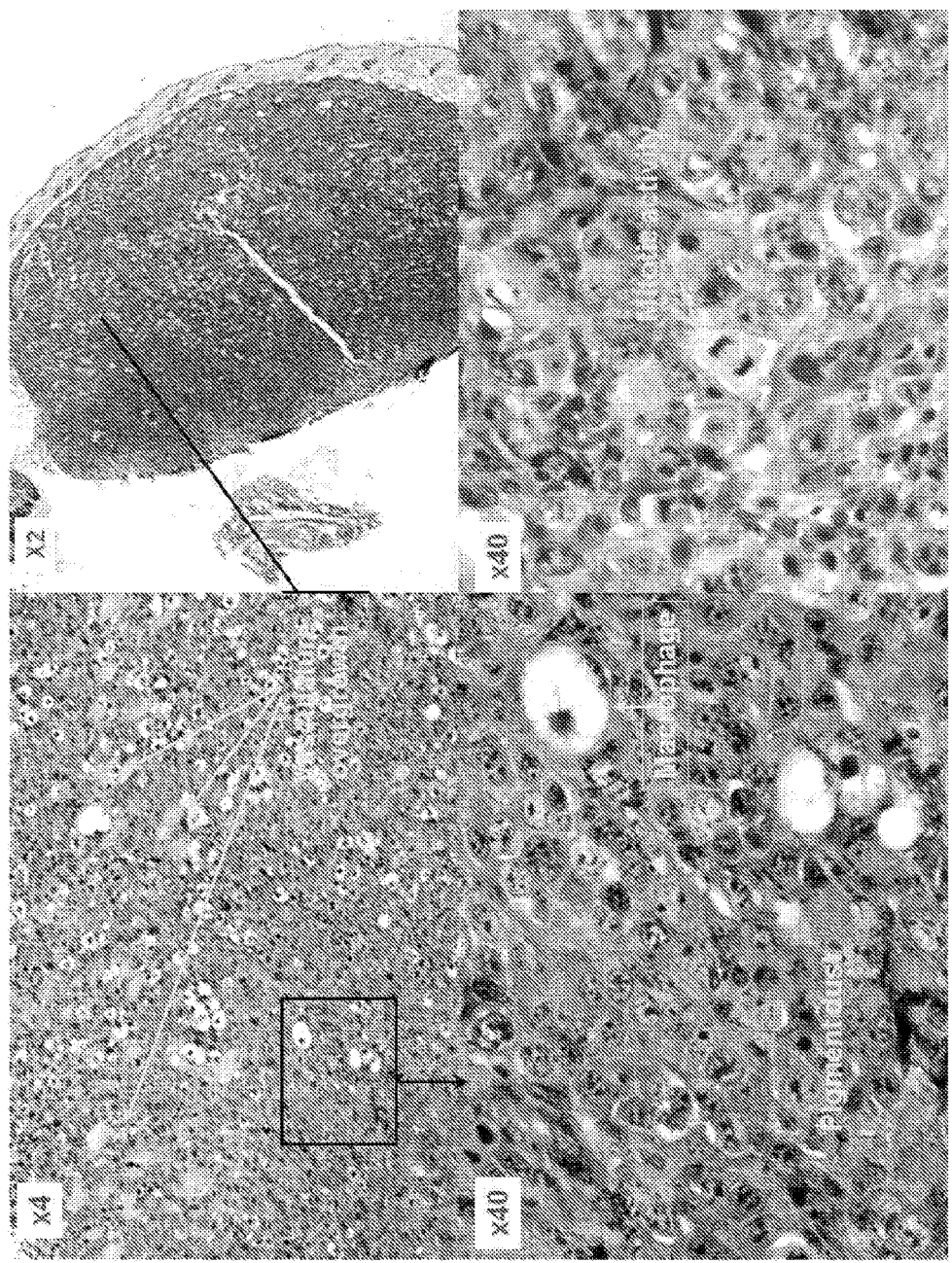

Reference is now made to FIG. 12B which show H&E histological staining of sections of tumors obtained from the tumor bearing mice. Isolated tumors were H&E stained to observe morphologically relevant areas. No sign of necrosis was observed within the tumors thereby minimizing the EPR effect.

Figure 12C:
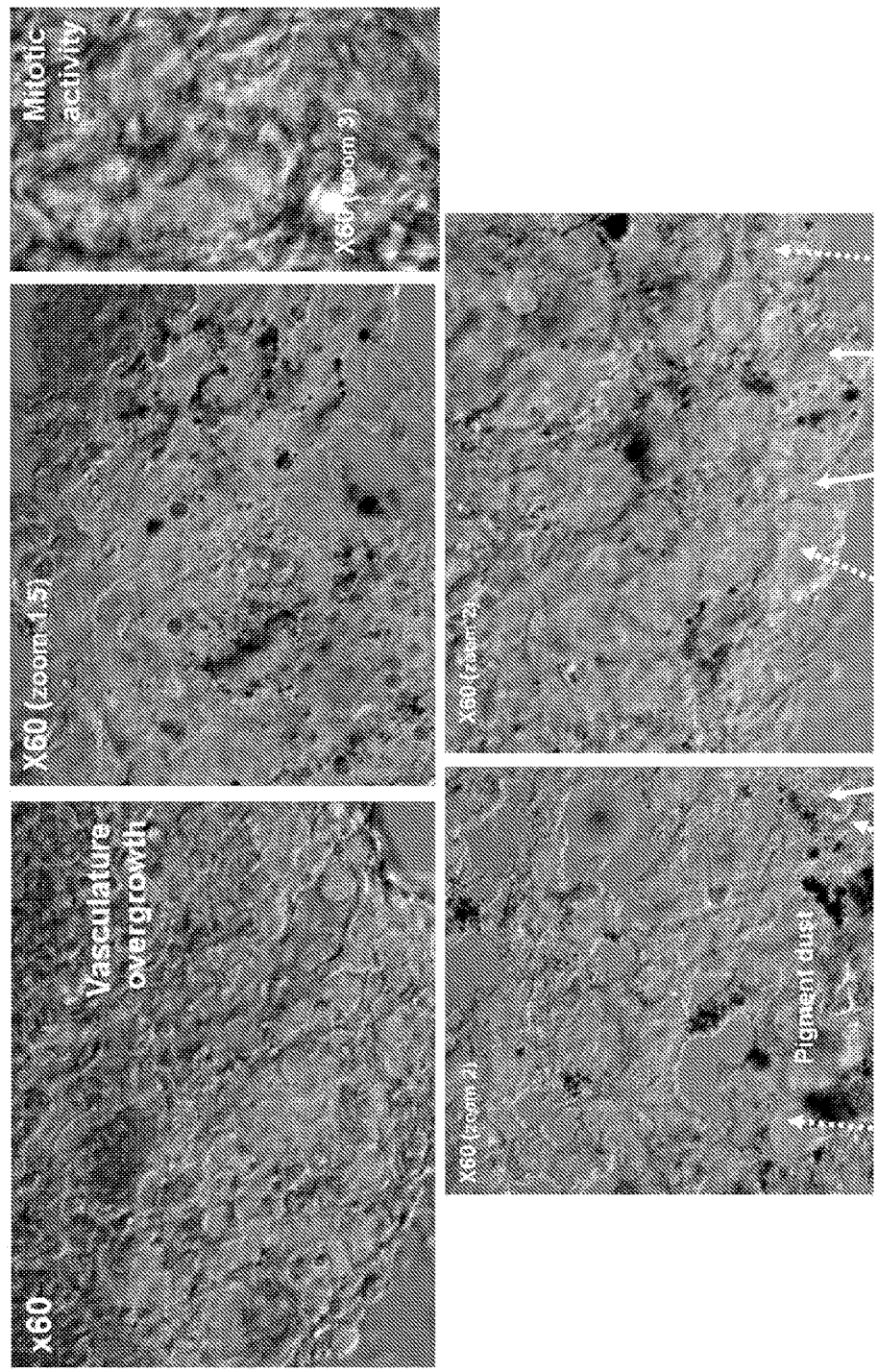

Reference is now made to FIG. 12C which show high resolution spectral fluorescent microscopic images of sections of tumors obtained from the tumor bearing mice. Fluorescence of Cy5-siRNA was observed both within tumor vasculature as well as in adjacent melanocytes, 6 hours post administration. Figures show cell nuclei (DAPI, dashed arrows) and fluorescent siRNA (solid arrows).

Example 12—Determination of Toxic Effects of In Vivo Administration of Improved Gagomer Composition Encapsulating siRNA In order to determine toxic effects of in vivo administration of the improved Gagomer composition encapsulating siRNA molecules (by intravenous (IV) administration), 40 C57BL mice at the age of 8-10 weeks are divided to 6 experimental groups with 5 mice each and one control group with 10 mice, as described in Table 2. Experimental groups I-VI are administered with a single bolus IV injection into the tail vain at day 0. Administration is performed at a constant volume dosage based on individual body weights. Animals from experimental Group VII are used as intact normal control.

Description of the test material: Double-stranded chemically modified siRNA against Aha1. Under sterile conditions, 20 mg of siRNA powder are dissolved in 1 ml of sterile double distilled water, to achieve a clear 20 mg/ml solution. The solution is stored at −80° C. until use. 2.5 µl of the 20 mg/ml siRNA stock solution (50 µg) is mixed with 100 µl lipid composition solution (50 µl (500 µg) from a 10 mg/ml stock; and 50 µl (100 µg) of activated (2 mg EDC) hyaluronic acid, to achieve final concentration 50 µg siRNA in 100 µl WFI.

Parameters tested: Terminal Blood from sacrificed animals was divided into 2 tubes one for Plasma and one for Serum. Plasma was used to test for cytokine level induction using 16-plex cytokine kit (Quansys). Serum was used to detected liver enzyme levels (SGPT/ALT, SGOT/AST), as well as cholesterol, triglyceride and HDL levels. Organs (liver, spleen, lung and kidneys) were collected and subjected to histological analysis after fixation in paraformaldehyde and blocking in paraffin blocks and stained with HE and mounted on slides. Additionally, changes in body weight in treated versus non-treated animals were performed.

TABLE 2

| Group | SiRNA Type | Dose (mg/kg) | Injected Volume (µl) | Route | Termination time points (hrs/days) | Group Size |
|---|---|---|---|---|---|---|
| I | siAha1 | 2 | 100 | IV | 1 | 5 |
| II | siAha1 | | | IV | 4 | 5 |
| III | siAha1 | | | IV | 7 | 5 |
| IV | siAha1 | | | IV | 16 | 5 |
| V | siAha1 | | | IV | 24 | 5 |
| VI | siAha1 | | | IV | 48 | 5 |
| VII | siAha1 | | | IV | 72 | 5 |
| VIII | siAha1 | | | IV | 5 days | 5 |
| IX | siAha1 | | | IV | 7 days | 5 |
| X | siAha1 | | | IV | 14 days | 5 |
| XI | N/A | N/A | N/A | N/A | 48/7 d/14 d | 14 |

Figure 13:
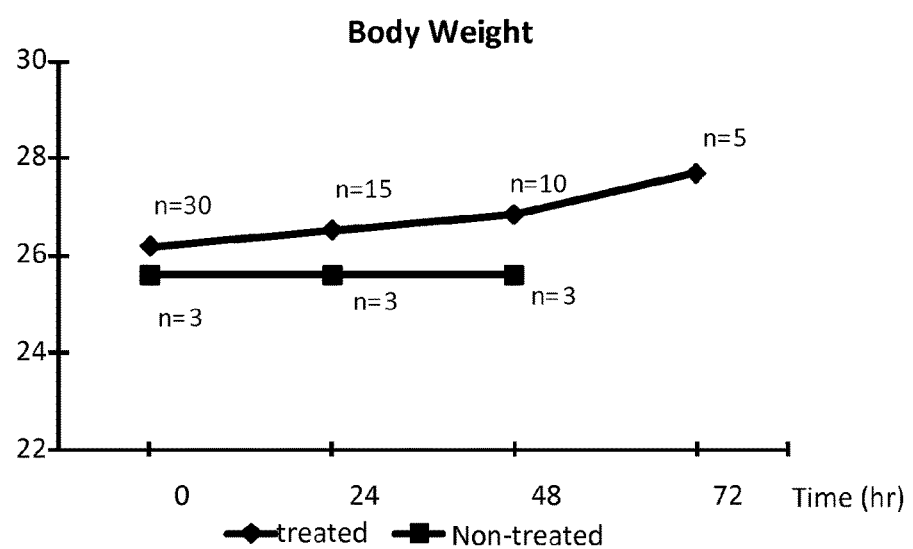
FIG. 13—Line graphs showing changes in body weight (g) over time (hours) of mice administered with the Gagomer-siRNA composition (treated) and of non-treated mice.

As shown in FIG. 13, which illustrates a line graphs of changes in body weight (g) over time (hours) of treated and non-treated animals, administration of the Gagomer-siRNA did not effect body weight of the tested animals. Body weight was measured throughout the entire experiment. Animals were weighted prior to terminal bleeding.

FIGS. 14A-D present bar graphs demonstrating the levels of various liver enzymes and other lipids in serum of tested mice (n=5 at each time point).

Figure 14A:
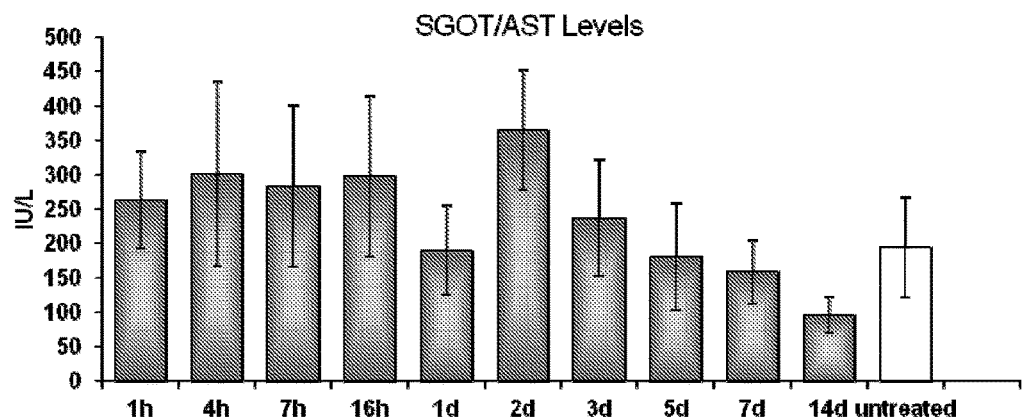
FIGS. 14A-D—Bar graphs of the levels of various liver enzymes and lipids in serum obtained from mice at different time points (hours/days) after administration of the Gagomer-siRNA composition (n=5 for each time point/group).

FIG. 14A shows bar graphs of the levels of SGOT/AST (IU/L) at different time points (hours/days) after administration of the Gagomer-siRNA composition, in serum obtained from tested mice.

Figure 14B:
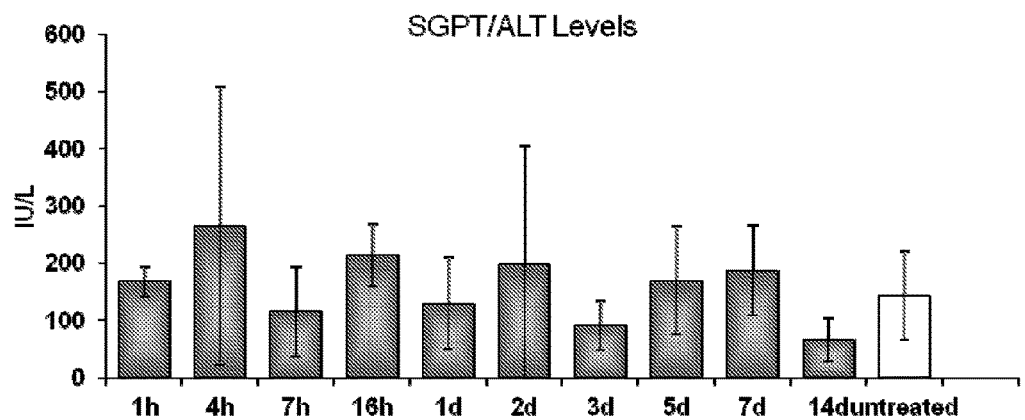

FIG. 14B shows bar graphs of the levels of SGPT/ALT (IU/L) at different time points (hours/days) after administration of the Gagomer-siRNA composition, in serum obtained from tested mice.

Figure 14C:
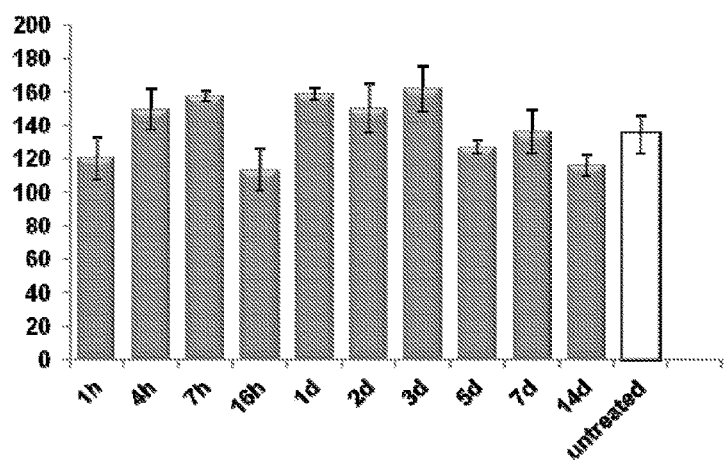

FIG. 14C shows bar graphs of the levels of Cholesterol (mg/dL) at different time points (hours/days) after administration of the Gagomer-siRNA composition, in serum obtained from tested mice.

Figure 14D:
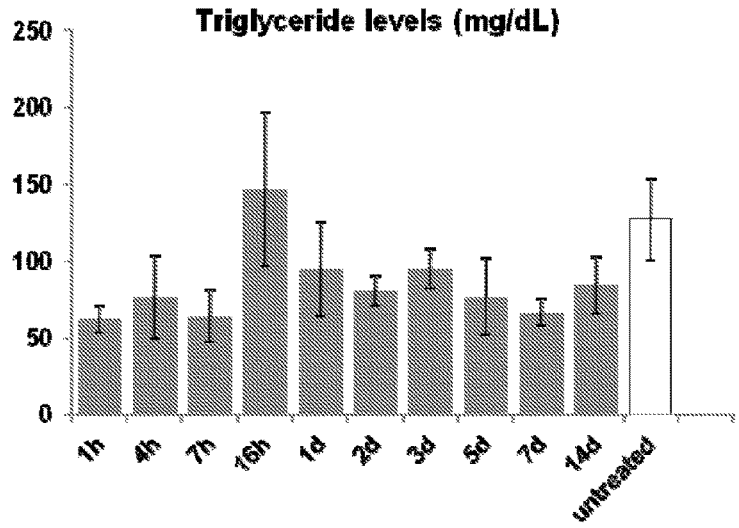

FIG. 14D shows bar graphs of the levels of triglycerides (mg/dL) at different time points (hours/days) after administration of the Gagomer-siRNA composition, in serum obtained from tested mice.

The results presented in FIGS. 14A-D demonstrate that administration of the Gagomer-siRNA composition to the tested animals did not significantly effect elevation of liver enzymes ALS and AST. Likewise, no significant effect of cholesterol, triglycerides or HDL levels is observed.

FIGS. 15A-D present bar graphs of the levels of various cytokines in blood of tested mice (n=5 at each time point).

Figure 15A:
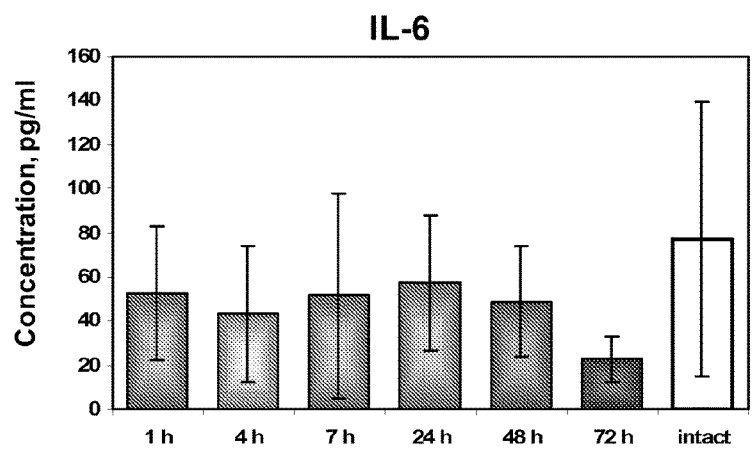
FIGS. 15A-D—Bar graphs of the concentration of various cytokines in blood obtained from mice at different time points (hours) after administration of the Gagomer-siRNA composition (n=5 for each time point/group).

FIG. 15A shows bar graphs of the concentration of IL-6 (pg/ml) at different time points (hours) after administration of the Gagomer-siRNA composition, in blood of tested mice.

Figure 15B:
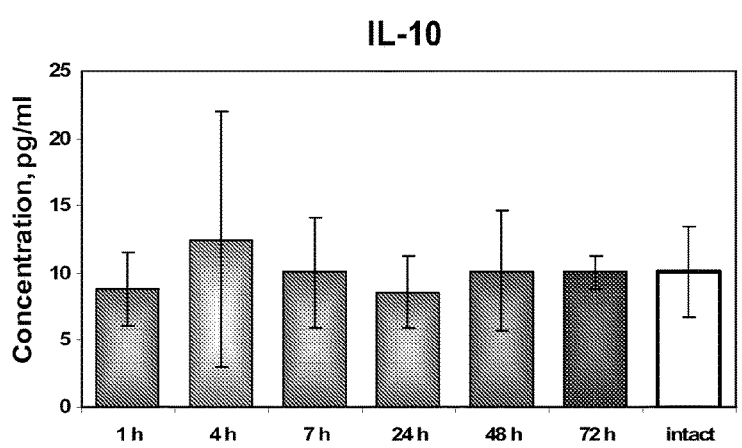

FIG. 15B shows bar graphs of the concentration of IL-10 (pg/ml) at different time points (hours) after administration of the Gagomer-siRNA composition, in blood of tested mice.

Figure 15C:
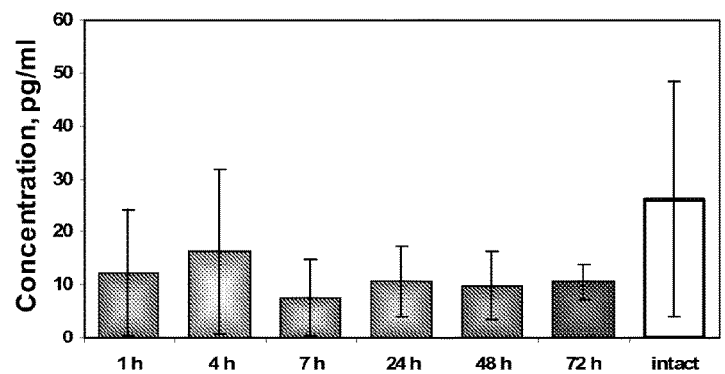

FIG. 15C shows a bar graphs of the concentration of IFNγ (pg/ml) at different time points (hours) after administration of the Gagomer-siRNA composition, in blood of tested mice.

Figure 15D:
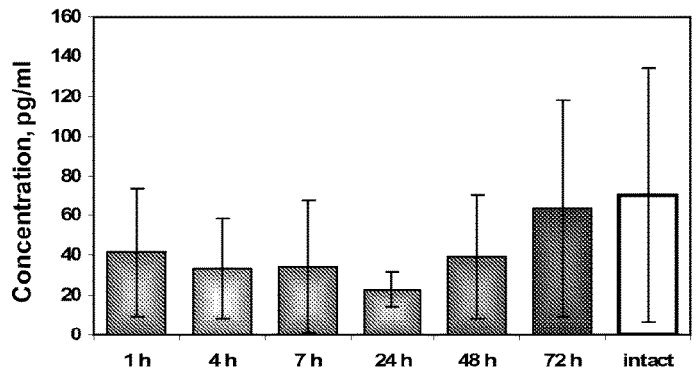
Figure 16A:
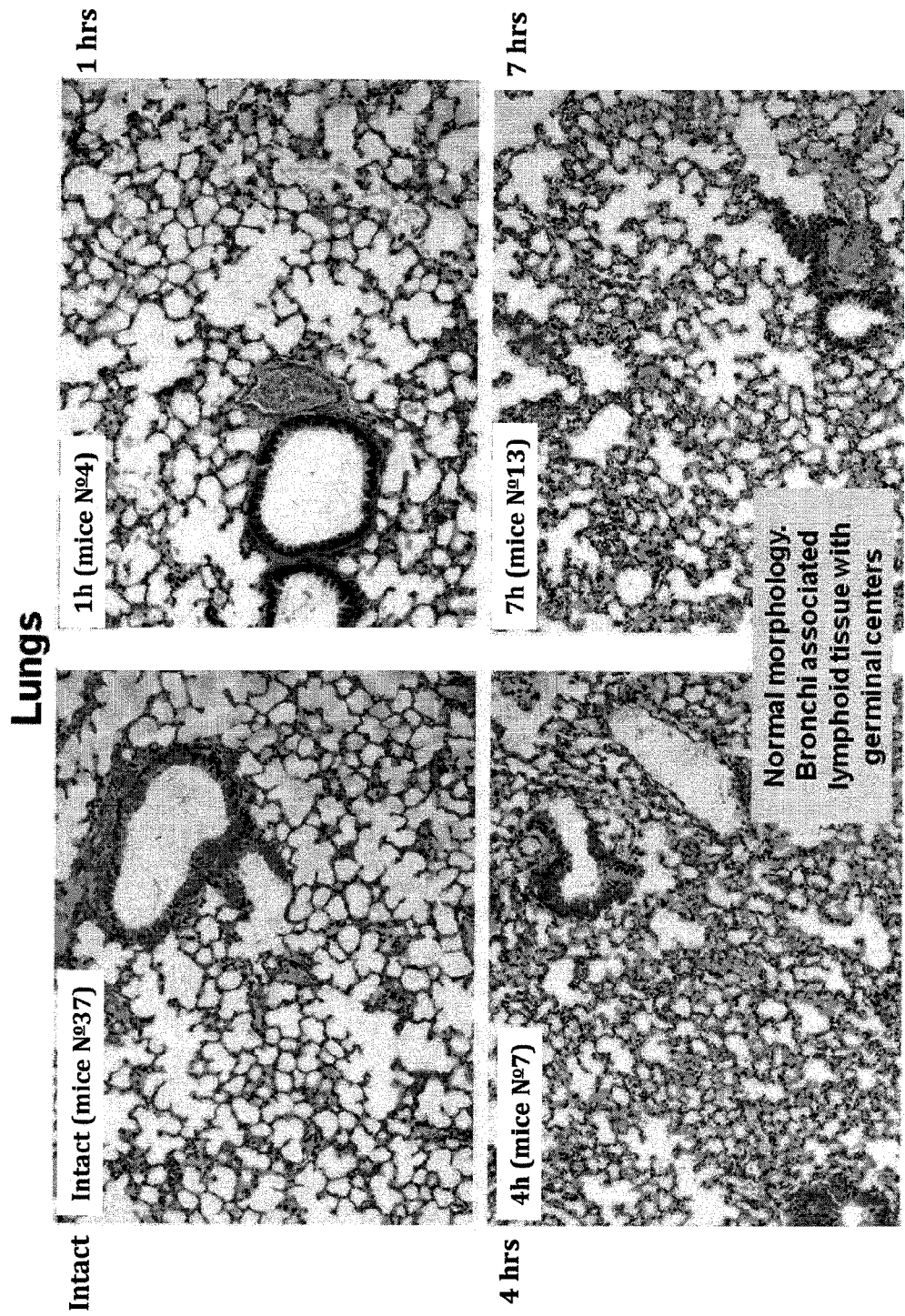
FIGS. 16A-D—Pictograms of histological sections of tissues obtained from tested mice up to seven hours after administration of Gagomer-siRNA composition.
Figure 16B:
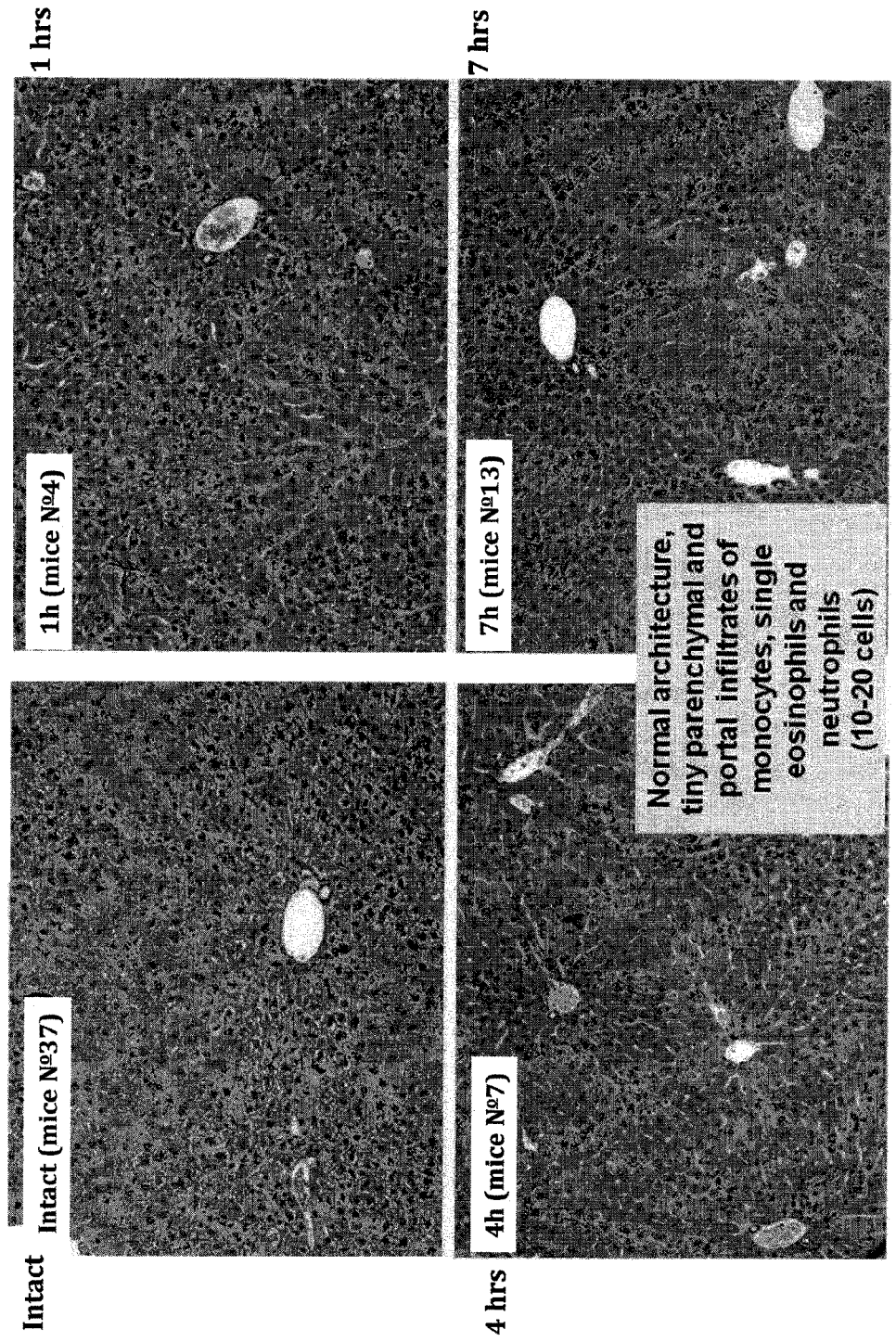
Figure 16C:
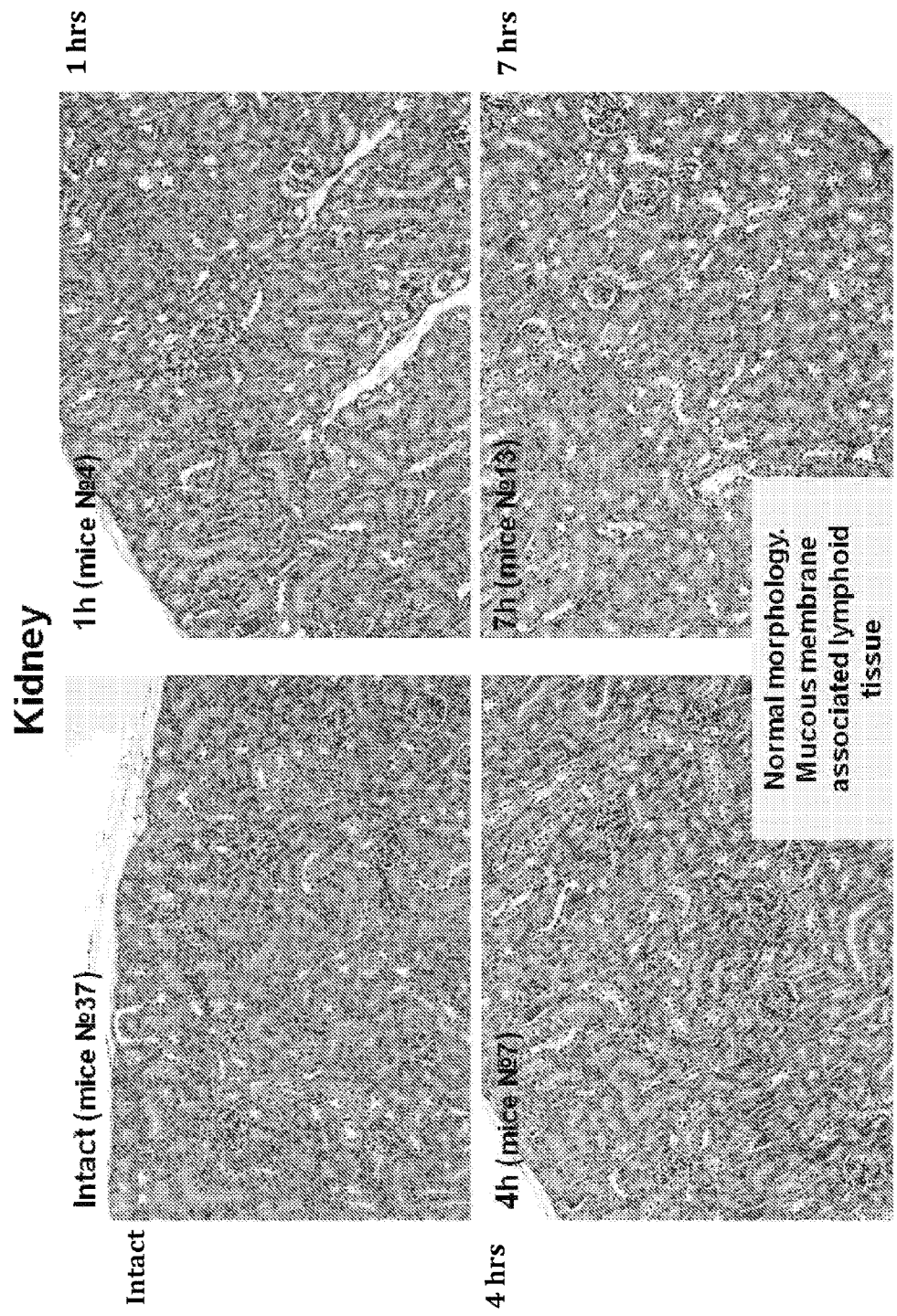
Figure 16D:
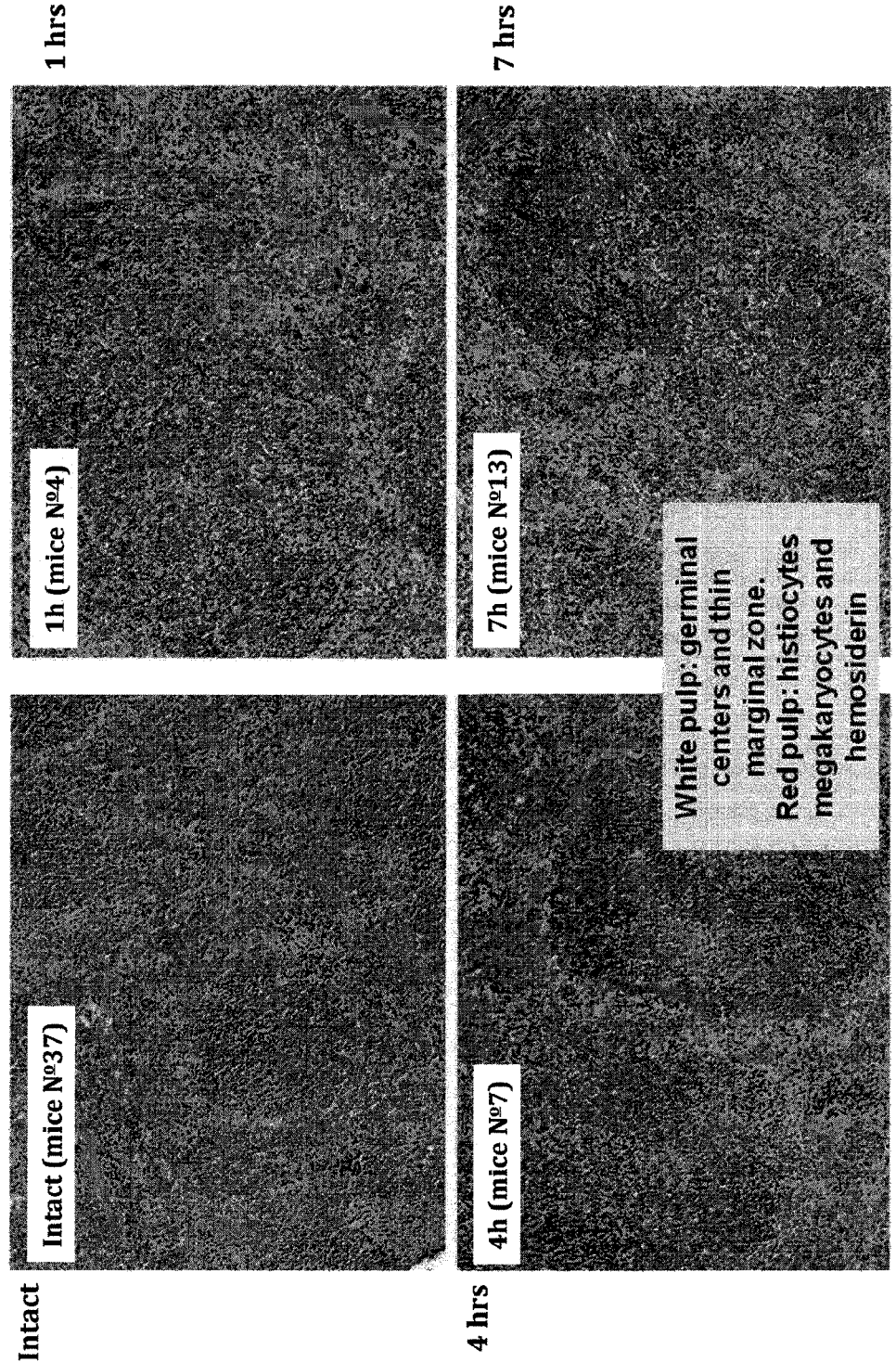

FIG. 15D shows a bar graphs of the concentration of TNFα (pg/ml) at different time points (hours) after administration of the Gagomer-siRNA composition, in blood of tested mice.

The results presented in FIGS. 15A-D demonstrate that administration of the Gagomer-siRNA composition to the tested animals did not induce an immune response of cytokines.

Analysis of various histological sections of tissues obtained from tested mice (seven hours after administration of Gagomer-siRNA composition) does not show any pathological or abnormal histological findings in lungs, liver, kidneys and spleen (FIGS. 16A-D, respectively).

Example 13—Systemic Delivery of Gagomer-siRNA Shows Tumor Specific Gene Knockdown Gagomer siRNA compositions were administered IV via tail vein (0.4 mg/kg), 5 days post B16-F10 inoculation and animals were sacrificed 24 hrs later. The Gagomer siRNA compositions were: 1. the Gagomer composition comprising siRNA against Aha1 ("siAha1", prepared as described in Example 12), and, 2. the Gagomer composition comprising siRNA against Luciferase ("siLuc", prepared as described above, siRNA against F-Luc, Roche, catalog #RD-01003K74). Total RNA was extracted from frozen samples (Liver, lung and Tumor tissue) using EZ-RNA (Total RNA Isolation Kit, Biological Industries, Cat. 20-400-100) according to the manufacture instructions and cDNA was synthesized using Thermo Scientific Verso™ cDNA Synthesis Kit (Thermo Scientific, Cat. No AB-1453/B) according to the manufacturer instructions in Eco™ Real-Time PCR System. Relative quantities of Aha 1 gene level expression in all tissue samples was measured using ABsolute™ Blue QPCR ROX Mix (2×) (Thermo Scientific, Cat. No. AB-4139/A) according to the manufacturer instructions in Eco™ Real-Time PCR System.

Figure 17A:
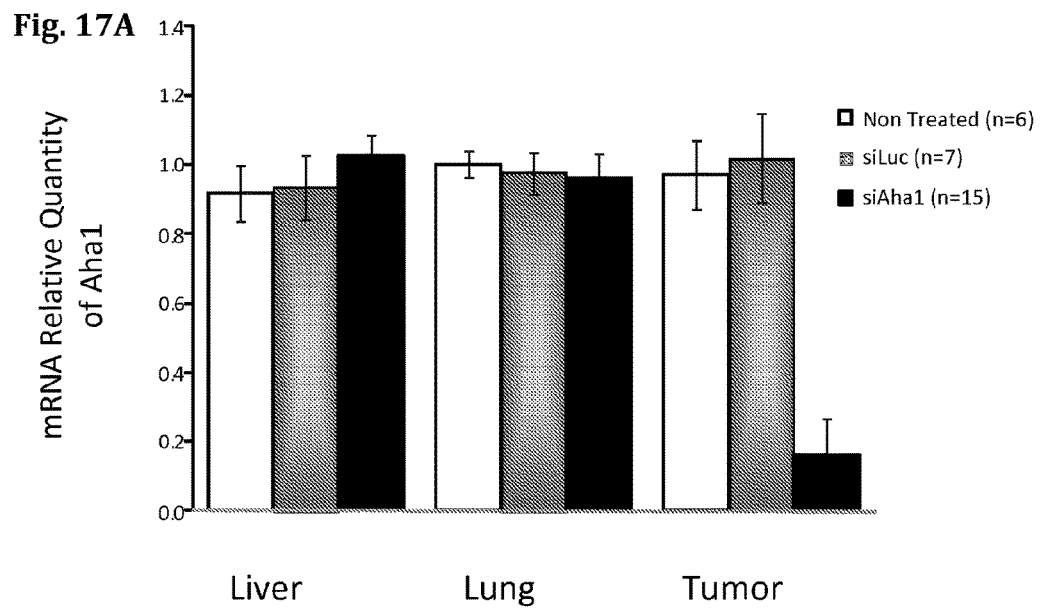
FIG. 17A-B—Bar graphs showing relative mRNA expression of Aha1 expression in various tissues obtained from mice, inoculated with B16-F10 cells and 5 days later were systemically administered with the indicated Gagomer-siRNA compositions. 24 hours after administration of the Gagomer-siRNA compositions, the mice were sacrificed and the indicated tissues were extracted and analyzed for expression of Aha1. The Gagomer compositions include: 1. A control Gagomer-siRNA composition comprising siRNA against Luciferase ("siLuc"), 2. A test Gagomer-siRNA composition comprising siRNA against Aha1 (siAha1). "Non treated" indicates mice that were not administered with a Gagomer-siRNA composition.

The results shown in the bar graphs presented in FIG. 17A demonstrate that the relative mRNA quantity (expression) of the Aha1 gene did not change in non tumor tissues, under any treatment (control siRNA-Gagomer composition or Aha1-siRNA-Gagomer composition), whereas, in the tumor tissue, the expression of the Aha1 gene was specifically reduced (up to 85% reduction) only in mice treated with siAha1-Gagomers, but not in control (non treated mice), or mice treated with the control siLuc-Gagomer composition.

Next, a dose-dependent experiment was performed, whereby the mice were administered with varying doses of the various siRNA-Gagomer compositions and scarified at various time points after administration. The results shown in the bar graphs presented in FIG. 17B demonstrate that there is a dose dependent effect of the specific Gagomer-siRNA (siAha) on the expression of the Aha1 gene in the tumors.

Altogether, the results presented herein demonstrate that the improved Gagomer-siRNA compositions can effectively function in-vivo. Furthermore, they are targeted to the tumor site and are able to specifically exert the gene silencing effect in a dose dependent manner.

Example 14—The Improved Gagomer-siRNA Composition can Specifically Target Metastatic Colonies in Metastases Lungs In-Vivo, after Systemic, Administration As demonstrated aboveherein in previous examples, it has been shown that using the subcutaneous tumor model, tumor specific targeting after single IV administration of fluorescently labeled siRNA formulated in the improved Gagomer composition. The fluorescence was identified in the blood stream and subsequently tumor cell-specific delivery into the subcutaneous tumors.

Figure 17B:
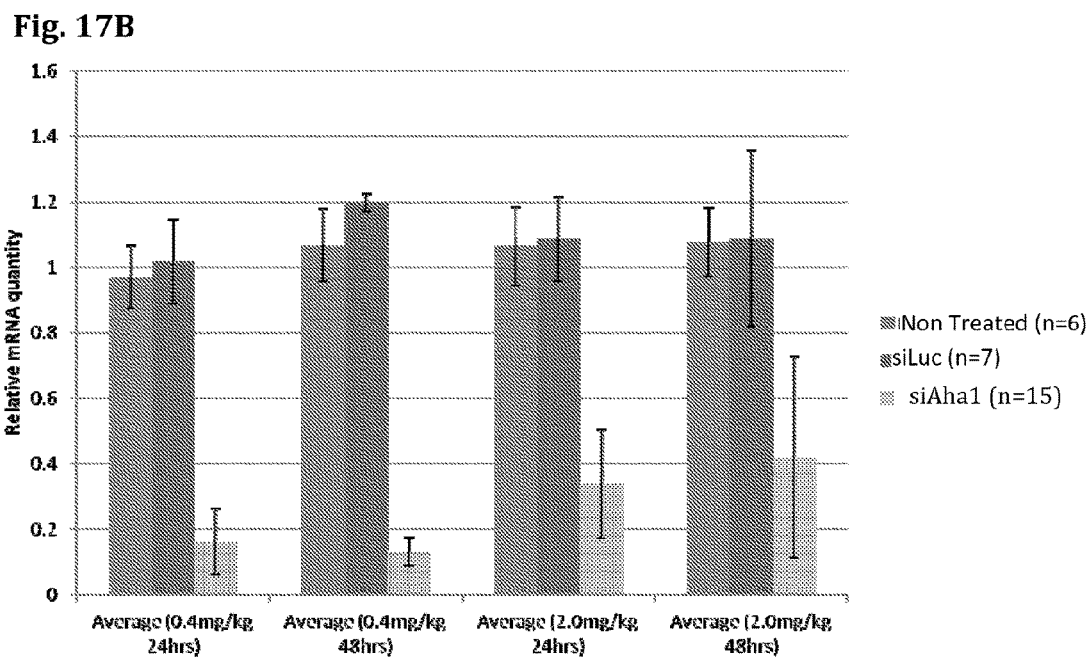
Figure 18A:
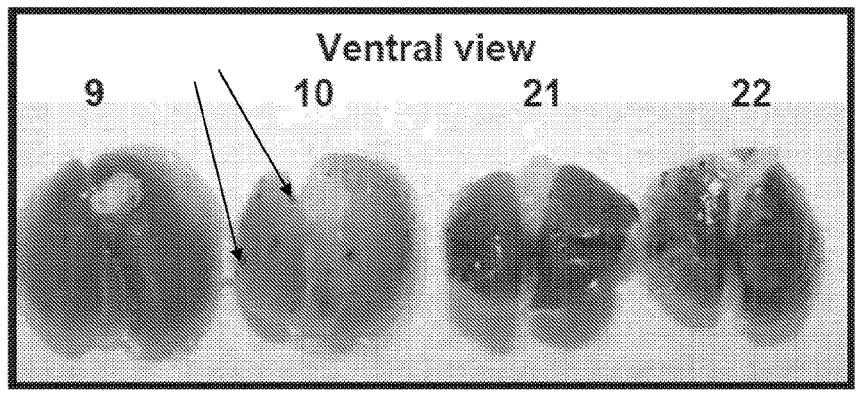
FIGS. 18A-C—Pictograms of lungs obtained from C57BL mice, administered with B16-F10 cells (IV), to induce lung metastatic. The lungs were retrieved ten days after IV administration of the B16-F10 cells.
Figure 18B:
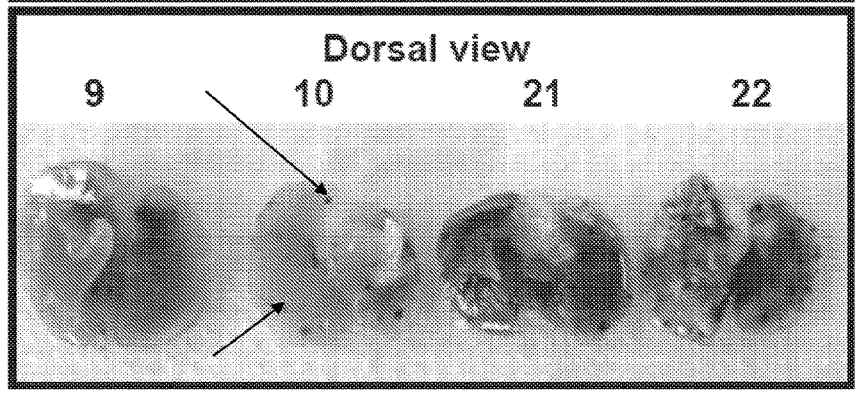
Figure 18C:
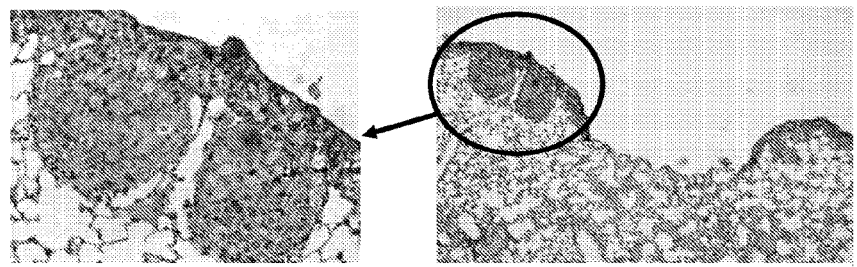

However, as opposed to metastatic growths, which is not generally associated with highly developed blood vessels and is different in morphology to solid tumors, an in-vivo metastatic model was established to demonstrate that the improved Gagomer composition can also specifically target metastatic colonies after systemic, intravenous (IV), administration. The in-vivo metastatic model used was metastatic lung carcinoma. This metastatic model was established by intra venous (IV) administration of $5\times10^5$ B16-F10 cells into C57BL mice. Lungs from the infused mice were harvested at 7, 10 and 14 days (n=5) and used for macroscopic and histological analysis. Establishment of metastasis in the lungs following IV administration of the B16-F10 cells was demonstrated. Animals sacrificed at day 10 already showed clear signs of metastatic colonization in the lung with growths showing subpleural aggregation with initialization of parenchymal invasion. The results are shown in FIGS. 17A-C, which show macroscopic and histological analysis of lungs obtained from mice 10 days after administration of the B16-F10 cells. As shown in FIGS. 17A-B, metastatic colonization can be easily identified (identified as black dots, and arrows indicating exemplary colonies). As shown in the histological preparation of FIG. 17C, signs of sub-pleural aggregation with accompanying parenchymal invasion can be identified in the lungs.

Using the established metastasis model, improved Gagomer-siRNA compositions (dually labeled with fluorescent labels), were systemically administered to the mice that had been previously inoculated with B16-F10 cells. The dual fluorescent labeling was performed on the encapsulated siRNA using the Cy5 label (red) and on the glycosaminoglycan moiety (Hyaluronic acid (HA) in this example), which was labeled with FITC. The mice administered (IV, 2 mg/kg) with the Gagomer-siRNA compositions were sacrificed at various time points after administration, and lung sections were examined under bright light microscope and fluorescent imaging. As shown in the results presented in FIGS. 19A-D, the fluorescent signal (attributed to the siRNA and the Gagomer itself) is preferentially accumulated in lung metastases, further demonstrating the gagomer composition as a specific targeting vehicle for nucleic acids and siRNA in particular. More particularly, the fluorescent signal can be identified even after 1 hour after administration, and increases with time (3 hours and 7 hours after administration). The co-localization of the Cy5 fluorescent label and the FITC label indicating that the Gagomer-siRNA composition in its entirety localizes to the tumor cells.

The kinetics of fluorescent labeling in the metastatic model is different than that observed in solid subcutaneous tumor (presented above). Whereas for the solid subcutaneous tumor, the fluorescence was at peak at shorter time points, for the metastasis tumor, the fluorescence peaks at later time points. This may be attributed to the differential vascularization between the two types of tumors (solid versus metastatic).

REFERENCES

Manjunath N. and Dykxhoorn Derek M. (2010). Advances in synthetic siRNA delivery. Discovery Medicine, 9(48): 418-430.

Weinstein S, and Peer D. (2010). RNAi nanomedicines: challenges and opportunities within the immune system. Nanotechnology 21, 21(23), 232001, 1-13.

Peer D (2010). Induction of therapeutic gene silencing in leukocyte-implicated diseases by targeted and stabilized nanoparticles: A mini-review. Journal of Controlled Release 148, 63-68.

Peer D, Park E J, Morishita Y, Carman C V, and Shimaoka M (2008). Systemic leukocyte-directed siRNA delivery revealing cyclin D1 as an anti-Inflammation target. Science. 319, 627-630.

Lee H, Mok H, Lee S, Oh Y K, Park T G (2007). Target-specific intracellular delivery of siRNA using degradable hyaluronic acid nanogels. J Control Release. 2007 Jun. 4; 119(2):245-52.

Choi K Y, Chung H, Min K H, Yoon H Y, Kim K, Park J H, Kwon I C, Jeong S Y (2010). Self-assembled hyaluronic acid nanoparticles for active tumor targeting. Biomaterials, January; 31(1):106-14.

Taetz S, Bochot A, Surace C, Arpicco S, Renoir J M, Schaefer U F, Marsaud V, Kerdine-Roemer S, Lehr C M, Fattal E. (2009). Hyaluronic acid-modified DOTAP/DOPE liposomes for the targeted delivery of anti-telomerase siRNA to CD44-expressing lung cancer cells. Oligonucleotides. 2009 June; 19(2): 103-16.

What is claimed is:

1. A composition comprising water insoluble lipidated glycosaminoglycan particles comprising
   (i) a plurality of lipids forming a particulate lipid composition, wherein the plurality of lipids comprises monocationic lipid N-[1-(2,3-Dioleoyloxy)]-N,N,N-trimethylammonium propane (DOTAP), 1,2-dilauroyl-Lphosphatidyl-ethanolamine (DLPE), and cholesterol, wherein the relative molar amount of DOTAP is greater than the relative molar amount of DLPE and the relative molar amount of cholesterol, and wherein the relative amount of DLPE in the composition is 11% to about 25%, and
   (ii) a nucleic acid encapsulated within the particles, wherein the weight ratio of the nucleic acid to lipids is less than 1:1, and wherein the composition is not a liposome.

2. The composition of claim 1, wherein the glycosaminoglycan is selected from hyaluronic acid, Chondroitin sulfate, Dermatan sulfate, Keratan sulfate, Heparin, Heparan sulfate, salts, and mixtures thereof.

3. The composition of claim 2, wherein the hyaluronic acid comprises high molecular weight hyaluronic acid.

4. The composition of claim 1, wherein the particulate lipid composition have a particle size of over about 200 nm.

5. The composition of claim 1, wherein the nucleic acid comprises DNA, RNA, modified forms thereof, and combinations thereof.

6. The composition of claim 5, wherein the RNA is selected from siRNA, miRNA, shRNA, antisense RNA and combinations thereof.

7. The composition of claim 1, wherein the weight ratio between the plurality of lipids and the nucleic acid is 10:1.

8. The composition of claim 1 further comprising a targeting moiety.

9. The composition of claim 1, wherein the particles are adapted to deliver the nucleic acid to a target site and wherein the target site is selected from the group consisting of a tumor, a cell, a tissue, an organ, and a microorganism.

10. A composition according to claim 1 in the form of freeze dried particles.

11. A pharmaceutical composition comprising the particles according to claim 1 in a dosage form suitable for administration via a route selected from oral, parenteral and topical.

12. The composition of claim 1, wherein the relative molar amount of DOTAP is about 30-80% and the relative molar amount of cholesterol is about 10-50%.

13. The composition of claim 1, wherein the relative molar amount of DOTAP is about 50% and the relative molar amount of cholesterol is about 35%.

14. The composition of claim 3, wherein the molecular weight of the hyaluronic acid is about $3.1 \times 10^5$ to about $1.5 \times 10^6$ daltons.

* * * * *